US012667468B2

(12) United States Patent
Gannoe et al.

(10) Patent No.: US 12,667,468 B2
(45) Date of Patent: Jun. 30, 2026

(54) SYSTEMS AND METHODS FOR LIMB ALIGNMENT

(71) Applicant: OrthAlign, Inc., Aliso Viejo, CA (US)

(72) Inventors: James Gannoe, Laguna Niguel, CA (US); Steven DeVincentis, Laguna Hills, CA (US)

(73) Assignee: OrthAlign, Inc., Irvine, CA (US)

( * ) Notice: Subject to any disclaimer, the term of this patent is extended or adjusted under 35 U.S.C. 154(b) by 500 days.

(21) Appl. No.: 17/822,554

(22) Filed: Aug. 26, 2022

(65) Prior Publication Data

US 2023/0059247 A1      Feb. 23, 2023

Related U.S. Application Data

(63) Continuation of application No. PCT/US2021/022973, filed on Mar. 18, 2021.
(Continued)

(51) Int. Cl.
| *A61F 2/46* | (2006.01) |
| *A61B 17/15* | (2006.01) |
(Continued)

(52) U.S. Cl.
CPC ............ *A61F 2/461* (2013.01); *A61B 17/155* (2013.01); *A61B 17/157* (2013.01); *A61B 2017/00725* (2013.01); *A61B 2017/564* (2013.01); *A61B 2034/2048* (2016.02); *A61F 2002/4658* (2013.01); *A61F 2002/4668* (2013.01)

(58) Field of Classification Search
CPC ................ A61B 17/155; A61B 17/157; A61B 2034/2048; A61B 2017/00725; A61B 2017/564; A61F 2/461; A61F 2002/4658; A61F 2002/4668; A61F 2034/2048
See application file for complete search history.

(56) References Cited

U.S. PATENT DOCUMENTS

| 3,174,080 A | 3/1965 | Eldon |
| 3,670,324 A | 6/1972 | Trevor, 3rd |
(Continued)

FOREIGN PATENT DOCUMENTS

| CA | 2241359 | 12/1999 |
| CA | 2 594 874 | 7/2006 |
(Continued)

OTHER PUBLICATIONS

Shah et al., "Is the pelvis stable during supine total hip arthroplasty?", Acta Orthop Belg., Mar. 1, 2017, vol. 83, No. 1, pp. 81-86.
(Continued)

*Primary Examiner* — Sameh R Boles
(74) *Attorney, Agent, or Firm* — Knobbe, Martens, Olson & Bear, LLP

(57) ABSTRACT

The present invention provides, in certain embodiments, a device for determining the tibial mechanical axis and the femoral mechanical axis. The present invention also provides a surgical orientation device, a reference device, and/or a module configured to track the mechanical axes during movement to facilitate limb alignment. The present invention further provides the surgical orientation device, the reference device, and/or the module configured to determine a gap measurement.

19 Claims, 18 Drawing Sheets

Related U.S. Application Data

(60) Provisional application No. 62/992,537, filed on Mar. 20, 2020.

(51) Int. Cl.

| | |
|---|---|
| A61B 17/00 | (2006.01) |
| A61B 17/56 | (2006.01) |
| A61B 34/20 | (2016.01) |

(56) References Cited

U.S. PATENT DOCUMENTS

| | | | |
|---|---|---|---|
| 4,349,018 | A | 9/1982 | Chambers |
| 4,421,112 | A | 12/1983 | Mains et al. |
| 4,436,099 | A | 3/1984 | Raftopoulos |
| 4,459,985 | A | 7/1984 | McKay et al. |
| 4,475,549 | A | 10/1984 | Oh |
| 4,501,266 | A | 2/1985 | McDaniel |
| 4,509,393 | A | 4/1985 | Castiglione |
| 4,518,855 | A | 5/1985 | Malak |
| 4,524,766 | A | 6/1985 | Petersen |
| 4,529,348 | A | 7/1985 | Johnson et al. |
| 4,567,885 | A | 2/1986 | Androphy |
| 4,567,886 | A | 2/1986 | Petersen |
| 4,621,630 | A | 11/1986 | Kenna |
| 4,646,729 | A | 3/1987 | Kenna |
| 4,716,894 | A | 1/1988 | Lazzeri et al. |
| 4,718,078 | A | 1/1988 | Bleidorn et al. |
| 4,738,253 | A | 4/1988 | Buechel et al. |
| 4,759,350 | A | 7/1988 | Dunn et al. |
| 4,823,807 | A | 4/1989 | Russell et al. |
| 4,938,762 | A | 7/1990 | Wehrli |
| 4,944,760 | A | 7/1990 | Kenna |
| 4,945,799 | A | 8/1990 | Knetzer |
| 4,952,213 | A | 8/1990 | Bowman et al. |
| 5,002,547 | A | 3/1991 | Poggie et al. |
| 5,053,037 | A | 10/1991 | Lackey |
| 5,065,612 | A | 11/1991 | Ooka et al. |
| 5,067,821 | A | 11/1991 | Young |
| 5,116,338 | A | 5/1992 | Poggie et al. |
| 5,122,146 | A | 6/1992 | Chapman et al. |
| 5,129,908 | A | 7/1992 | Petersen |
| 5,141,512 | A | 8/1992 | Farmer et al. |
| 5,171,244 | A | 12/1992 | Caspari et al. |
| 5,213,112 | A | 5/1993 | Niwa et al. |
| 5,249,581 | A | 10/1993 | Horbal et al. |
| 5,251,127 | A | 10/1993 | Raab |
| 5,279,309 | A | 1/1994 | Taylor et al. |
| 5,296,855 | A | 3/1994 | Matsuzaki et al. |
| 5,306,276 | A | 4/1994 | Johnson et al. |
| 5,320,625 | A | 6/1994 | Bertin |
| 5,324,293 | A | 6/1994 | Rehmann |
| 5,325,029 | A | 6/1994 | Janecke et al. |
| 5,329,933 | A | 7/1994 | Graf |
| 5,342,367 | A | 8/1994 | Ferrante et al. |
| 5,343,391 | A | 8/1994 | Mushabac |
| 5,358,526 | A | 10/1994 | Tornier |
| 5,376,093 | A | 12/1994 | Newman |
| 5,395,377 | A | 3/1995 | Petersen et al. |
| 5,417,694 | A | 5/1995 | Marik et al. |
| 5,423,827 | A | 6/1995 | Mumme |
| 5,431,653 | A | 7/1995 | Callaway |
| 5,462,548 | A | 10/1995 | Pappas et al. |
| 5,468,244 | A | 11/1995 | Attfield et al. |
| 5,474,088 | A | 12/1995 | Zaharkin et al. |
| 5,486,177 | A | 1/1996 | Mumme et al. |
| 5,514,143 | A | 5/1996 | Bonutti et al. |
| 5,529,070 | A | 6/1996 | Augustine et al. |
| 5,540,696 | A | 7/1996 | Booth, Jr. et al. |
| 5,540,697 | A | 7/1996 | Rehmann et al. |
| 5,553,198 | A | 9/1996 | Wang et al. |
| 5,576,727 | A | 11/1996 | Rosenberg et al. |
| 5,584,837 | A | 12/1996 | Peterson |
| 5,597,379 | A | 1/1997 | Haines et al. |
| 5,611,353 | A | 3/1997 | Dance et al. |
| 5,624,444 | A | 4/1997 | Wixson et al. |
| 5,628,750 | A | 5/1997 | Whitlock et al. |
| 5,645,077 | A | 7/1997 | Foxlin |
| 5,653,764 | A | 8/1997 | Murphy |
| 5,681,316 | A | 10/1997 | DeOrio et al. |
| 5,683,398 | A | 11/1997 | Carls et al. |
| 5,688,282 | A | 11/1997 | Baron et al. |
| 5,720,752 | A | 2/1998 | Elliot et al. |
| 5,724,264 | A | 3/1998 | Rosenberg et al. |
| 5,748,767 | A | 5/1998 | Raab |
| 5,769,861 | A | 6/1998 | Vilsmeier |
| 5,776,137 | A | 7/1998 | Katz |
| 5,788,700 | A | 8/1998 | Morawa et al. |
| 5,824,085 | A | 10/1998 | Sahay et al. |
| 5,840,047 | A | 11/1998 | Stedham |
| 5,880,714 | A | 3/1999 | Rosenberg et al. |
| 5,916,219 | A | 6/1999 | Matsuno et al. |
| 5,919,149 | A | 7/1999 | Allum |
| 5,935,086 | A | 8/1999 | Beacon et al. |
| 5,976,156 | A | 11/1999 | Taylor et al. |
| 6,027,507 | A | 2/2000 | Anderson et al. |
| 6,036,696 | A | 3/2000 | Lambrecht et al. |
| 6,056,756 | A | 5/2000 | Eng et al. |
| 6,063,124 | A | 5/2000 | Amstutz |
| 6,090,114 | A | 7/2000 | Matsuno et al. |
| 6,094,019 | A | 7/2000 | Saiki |
| 6,120,509 | A | 9/2000 | Wheeler |
| 6,122,538 | A | 9/2000 | Sliwa, Jr. et al. |
| 6,126,608 | A | 10/2000 | Kemme et al. |
| 6,162,191 | A | 12/2000 | Foxin |
| 6,167,292 | A | 12/2000 | Badano et al. |
| 6,171,310 | B1 | 1/2001 | Giordano |
| 6,195,615 | B1 | 2/2001 | Lysen |
| 6,197,032 | B1 | 3/2001 | Lawes et al. |
| 6,214,013 | B1 | 4/2001 | Lambrech et al. |
| 6,214,014 | B1 | 4/2001 | McGann |
| 6,216,029 | B1 | 4/2001 | Paltieli |
| 6,246,898 | B1 | 6/2001 | Vesely et al. |
| 6,258,095 | B1 | 7/2001 | Lombardo et al. |
| 6,261,247 | B1 | 7/2001 | Ishikawa et al. |
| 6,299,646 | B1 | 10/2001 | Chambat et al. |
| 6,332,089 | B1 | 12/2001 | Acker |
| 6,348,058 | B1 | 2/2002 | Melken et al. |
| 6,354,011 | B1 | 3/2002 | Albrecht |
| 6,361,506 | B1 | 3/2002 | Saenger et al. |
| 6,361,507 | B1 | 3/2002 | Foxlin |
| 6,361,508 | B1 | 3/2002 | Johnson et al. |
| 6,377,839 | B1 | 4/2002 | Kalfas et al. |
| 6,381,485 | B1 | 4/2002 | Hunter et al. |
| 6,383,149 | B1 | 5/2002 | DeMayo |
| 6,395,005 | B1 | 5/2002 | Lovell |
| 6,447,448 | B1 | 9/2002 | Ishikawa et al. |
| 6,468,280 | B1 | 10/2002 | Saenger et al. |
| 6,470,207 | B1 | 10/2002 | Simon et al. |
| 6,471,637 | B1 | 10/2002 | Green et al. |
| 6,473,635 | B1 | 10/2002 | Rasche |
| 6,477,400 | B1 | 11/2002 | Barrick |
| 6,477,421 | B1 | 11/2002 | Andersen et al. |
| 6,478,799 | B1 | 11/2002 | Williamson |
| 6,488,713 | B1 | 12/2002 | Hershnerger |
| 6,499,488 | B1 | 12/2002 | Hunter et al. |
| 6,514,259 | B2 | 2/2003 | Picard et al. |
| 6,527,443 | B1 | 3/2003 | Vilsmeier |
| 6,551,325 | B2 | 4/2003 | Neubauer et al. |
| 6,585,666 | B2 | 7/2003 | Suh et al. |
| 6,595,997 | B2 | 7/2003 | Axelson, Jr. et al. |
| 6,595,999 | B2 | 7/2003 | Marchione et al. |
| 6,607,487 | B2 | 8/2003 | Chang et al. |
| 6,640,128 | B2 | 10/2003 | Vilsmeier et al. |
| 6,648,896 | B2 | 11/2003 | Overes et al. |
| 6,679,916 | B1 | 1/2004 | Frankie et al. |
| 6,685,655 | B2 | 2/2004 | DeMayo |
| 6,685,711 | B2 | 2/2004 | Axelson et al. |
| 6,711,431 | B2 | 3/2004 | Sarin et al. |
| 6,712,824 | B2 | 3/2004 | Millard et al. |
| 6,715,213 | B2 | 4/2004 | Richter |
| 6,725,080 | B2 | 4/2004 | Melkent et al. |
| 6,725,173 | B2 | 4/2004 | An |
| 6,743,235 | B2 | 6/2004 | Rao |
| 6,770,078 | B2 | 8/2004 | Bonutti |

(56)        References Cited

U.S. PATENT DOCUMENTS

| | | | |
|---|---|---|---|
| 6,786,877 B2 | 9/2004 | Foxlin |
| 6,802,864 B2 | 10/2004 | Tornier |
| 6,817,470 B1 | 11/2004 | Goldberg |
| 6,820,025 B2 | 11/2004 | Bachmann et al. |
| 6,827,723 B2 | 12/2004 | Carson |
| 6,917,827 B2 | 7/2005 | Kienzle, III |
| 6,923,817 B2 | 8/2005 | Carson et al. |
| 6,928,742 B2 | 8/2005 | Broers et al. |
| 6,947,783 B2 | 9/2005 | Immerz |
| 6,986,181 B2 | 1/2006 | Murphy et al. |
| 6,997,882 B1 | 2/2006 | Parker et al. |
| 7,007,699 B2 | 3/2006 | Martinelli et al. |
| 7,021,140 B2 | 4/2006 | Perkins |
| 7,027,477 B2 | 4/2006 | Sutter et al. |
| 7,037,310 B2 | 5/2006 | Murphy |
| 7,048,741 B2 | 5/2006 | Swanson |
| 7,089,148 B1 | 8/2006 | Bachmann et al. |
| 7,094,241 B2 | 8/2006 | Hodorek et al. |
| 7,104,998 B2 | 9/2006 | Yoon et al. |
| 7,105,028 B2 | 9/2006 | Murphy |
| 7,194,295 B2 | 3/2007 | Vilsmeier |
| 7,209,776 B2 | 4/2007 | Leitner |
| 7,219,033 B2 | 5/2007 | Kolen |
| 7,273,500 B2 | 9/2007 | Williamson |
| 7,311,441 B2 | 12/2007 | Weaver et al. |
| 7,331,932 B2 | 2/2008 | Leitner |
| 7,344,541 B2 | 3/2008 | Haines et al. |
| 7,392,076 B2 | 6/2008 | Moctezuma de La Barrera |
| 7,396,357 B2 | 7/2008 | Tornier et al. |
| 7,444,178 B2 | 10/2008 | Goldbach |
| 7,468,075 B2 | 12/2008 | Lang et al. |
| 7,468,077 B2 | 12/2008 | Rochetin |
| 7,497,029 B2 | 3/2009 | Plassky et al. |
| 7,520,880 B2 | 4/2009 | Claypool et al. |
| 7,547,307 B2 | 6/2009 | Carson et al. |
| 7,559,931 B2 | 7/2009 | Stone |
| 7,578,821 B2 | 8/2009 | Fisher et al. |
| 7,594,933 B2 | 9/2009 | Kammerzell et al. |
| 7,611,520 B2 | 11/2009 | Broers et al. |
| 7,611,522 B2 | 11/2009 | Gorek |
| 7,621,920 B2 | 11/2009 | Claypool et al. |
| 7,623,902 B2 | 11/2009 | Pacheco |
| 7,726,564 B2 | 6/2010 | Goldbach |
| 7,776,098 B2 | 8/2010 | Murphy |
| 7,815,644 B2 | 10/2010 | Masini |
| 7,831,292 B2 | 11/2010 | Quaid et al. |
| 7,834,847 B2 | 11/2010 | Boillot et al. |
| 7,840,256 B2 | 11/2010 | Lakin et al. |
| 7,846,092 B2 | 12/2010 | Murphy |
| 7,857,821 B2 | 12/2010 | Couture et al. |
| 7,885,705 B2 | 2/2011 | Murphy |
| 7,970,174 B2 | 6/2011 | Goldbach |
| 8,057,479 B2 | 11/2011 | Stone |
| 8,057,482 B2 | 11/2011 | Stone |
| 8,078,254 B2 | 12/2011 | Murphy |
| 8,104,960 B2 | 1/2012 | Gill et al. |
| 8,118,815 B2 | 2/2012 | van der Walt |
| 8,241,296 B2 | 8/2012 | Wasielewski |
| 8,265,790 B2 | 9/2012 | Amiot et al. |
| 8,267,938 B2 | 9/2012 | Murphy |
| 8,277,455 B2 | 10/2012 | Couture et al. |
| 8,282,685 B2 | 10/2012 | Rochetin et al. |
| 8,355,773 B2 | 1/2013 | Leitner et al. |
| 8,412,308 B2 | 4/2013 | Goldbach |
| 8,421,854 B2 | 4/2013 | Zerkin |
| 8,446,473 B2 | 5/2013 | Goldbach |
| 8,512,346 B2 | 8/2013 | Couture |
| 8,551,108 B2 | 10/2013 | Pelletier et al. |
| 8,588,892 B2 | 11/2013 | Hladio et al. |
| 8,690,888 B2 | 4/2014 | Stein et al. |
| 8,718,820 B2 | 5/2014 | Amiot et al. |
| 8,734,432 B2 | 5/2014 | Tuma et al. |
| 8,764,758 B2 | 7/2014 | Echeverri |
| 8,867,198 B2 | 10/2014 | Steele |
| 8,888,786 B2 | 11/2014 | Stone |
| 8,911,447 B2 | 12/2014 | van der Walt et al. |
| 8,974,467 B2 | 3/2015 | Stone |
| 8,974,468 B2 | 3/2015 | Borja |
| 8,998,910 B2 | 4/2015 | Borja et al. |
| 9,044,218 B2 | 6/2015 | Young |
| 9,138,319 B2 | 9/2015 | Fanson et al. |
| 9,192,392 B2 | 11/2015 | van der Walt et al. |
| 9,262,802 B2 | 2/2016 | Aghazadeh |
| 9,271,756 B2 | 3/2016 | van der Walt et al. |
| 9,339,226 B2 | 5/2016 | van der Walt et al. |
| 9,375,178 B2 | 6/2016 | Aghazadeh |
| 9,456,769 B2 | 10/2016 | Stein et al. |
| 9,549,742 B2 | 1/2017 | Berend et al. |
| 9,572,586 B2 | 2/2017 | van der Walt et al. |
| 9,642,572 B2 | 5/2017 | Mahfouz et al. |
| 9,649,160 B2 | 5/2017 | van der Walt et al. |
| 9,775,725 B2 | 10/2017 | van der Walt et al. |
| 9,855,075 B2 | 1/2018 | van der Walt et al. |
| 9,930,946 B2 | 4/2018 | Zondervan |
| 9,931,059 B2 | 4/2018 | Borja |
| 10,206,714 B2 | 2/2019 | van der Walt et al. |
| 10,238,510 B2 | 3/2019 | van der Walt et al. |
| 10,321,852 B2 | 6/2019 | Borja |
| 10,363,149 B2 | 7/2019 | van der Walt et al. |
| 10,597,178 B2 | 3/2020 | Ryterski et al. |
| 10,603,115 B2 | 3/2020 | van der Walt et al. |
| 10,716,580 B2 | 7/2020 | Berend et al. |
| 10,863,995 B2 | 12/2020 | Nielsen et al. |
| 10,864,019 B2 | 12/2020 | van der Walt et al. |
| 10,869,771 B2 | 12/2020 | van der Walt et al. |
| 10,918,499 B2 | 2/2021 | Nielsen et al. |
| 11,020,245 B2 | 6/2021 | van der Walt et al. |
| 11,179,062 B2 | 11/2021 | Borja et al. |
| 11,179,167 B2 | 11/2021 | Stone |
| 11,191,334 B2 | 12/2021 | Aghazadeh et al. |
| 11,273,232 B2 | 3/2022 | Placik |
| 11,540,746 B2 | 1/2023 | Borja et al. |
| 11,547,451 B2 | 1/2023 | van der Walt et al. |
| 11,547,580 B2 | 1/2023 | Nielsen et al. |
| 11,633,293 B2 | 4/2023 | van der Walt et al. |
| 11,653,981 B2 | 5/2023 | van der Walt et al. |
| 11,684,392 B2 | 6/2023 | van der Walt et al. |
| 11,786,261 B2 | 10/2023 | Nielsen et al. |
| 11,871,965 B2 | 1/2024 | van der Walt et al. |
| 11,903,597 B2 | 2/2024 | Stone |
| 11,911,119 B2 | 2/2024 | van der Walt et al. |
| 12,127,801 B2 | 10/2024 | Walter et al. |
| 12,144,567 B2 | 11/2024 | van der Walt et al. |
| 12,232,863 B2 | 2/2025 | Borja et al. |
| 12,239,344 B2 | 3/2025 | van der Walt et al. |
| 12,318,313 B2 | 6/2025 | van der Walt et al. |
| 12,376,972 B2 | 8/2025 | van der Walt et al. |
| 12,433,694 B2 | 10/2025 | van der Walt et al. |
| 12,446,926 B2 | 10/2025 | van der Walt et al. |
| 2002/0077540 A1 | 6/2002 | Kienzie, III |
| 2002/0103610 A1 | 8/2002 | Bachmann et al. |
| 2002/0107522 A1 | 8/2002 | Picard et al. |
| 2002/0133175 A1 | 9/2002 | Carson |
| 2002/0198451 A1 | 12/2002 | Carson |
| 2003/0019294 A1 | 1/2003 | Richter |
| 2003/0069591 A1 | 4/2003 | Carson et al. |
| 2003/0093080 A1 | 5/2003 | Brown et al. |
| 2003/0105470 A1 | 6/2003 | White |
| 2003/0120282 A1 | 6/2003 | Scouten et al. |
| 2003/0163142 A1 | 8/2003 | Paltieli et al. |
| 2003/0181919 A1 | 9/2003 | Gorek |
| 2003/0184297 A1 | 10/2003 | Jakab |
| 2003/0199882 A1 | 10/2003 | Gorek |
| 2003/0204965 A1 | 11/2003 | Hennessey |
| 2003/0229356 A1 | 12/2003 | Dye |
| 2004/0006393 A1 | 1/2004 | Burkinshaw |
| 2004/0019382 A1 | 1/2004 | Amirouche et al. |
| 2004/0034313 A1 | 2/2004 | Leitner |
| 2004/0039396 A1 | 2/2004 | Couture et al. |
| 2004/0068260 A1 | 4/2004 | Cossette et al. |
| 2004/0073225 A1 | 4/2004 | Subba Rao |
| 2004/0087958 A1 | 5/2004 | Myers et al. |
| 2004/0087962 A1 | 5/2004 | Gorek |
| 2004/0097952 A1 | 5/2004 | Sarin et al. |

(56)  References Cited

U.S. PATENT DOCUMENTS

| | | |
|---|---|---|
| 2004/0102792 A1 | 5/2004 | Sarin et al. |
| 2004/0106916 A1 | 6/2004 | Quaid et al. |
| 2004/0122441 A1 | 6/2004 | Muratsu |
| 2004/0147926 A1 | 7/2004 | Iversen |
| 2004/0149036 A1 | 8/2004 | Foxlin et al. |
| 2004/0152955 A1 | 8/2004 | McGinley et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0181144 A1 | 9/2004 | Cinquin et al. |
| 2004/0201857 A1 | 10/2004 | Foxlin |
| 2004/0230197 A1 | 11/2004 | Tornier et al. |
| 2004/0243148 A1 | 12/2004 | Wasielewski |
| 2005/0021037 A1 | 1/2005 | McCombs et al. |
| 2005/0021044 A1 | 1/2005 | Stone et al. |
| 2005/0070864 A1 | 3/2005 | Fellion |
| 2005/0107799 A1 | 5/2005 | Graf et al. |
| 2005/0113846 A1 | 5/2005 | Carson |
| 2005/0149040 A1 | 7/2005 | Haines et al. |
| 2005/0149054 A1 | 7/2005 | Gorek |
| 2005/0197814 A1 | 9/2005 | Aram et al. |
| 2005/0209605 A1 | 9/2005 | Grimm et al. |
| 2005/0222574 A1 | 10/2005 | Giordano et al. |
| 2005/0234332 A1 | 10/2005 | Murphy |
| 2005/0251026 A1 | 11/2005 | Stone |
| 2005/0251148 A1 | 11/2005 | Friedrich |
| 2006/0009780 A1 | 1/2006 | Foley et al. |
| 2006/0015018 A1 | 1/2006 | Jutras et al. |
| 2006/0015120 A1 | 1/2006 | Richard et al. |
| 2006/0020177 A1 | 1/2006 | Seo et al. |
| 2006/0064105 A1 | 3/2006 | Raistrick et al. |
| 2006/0084977 A1 | 4/2006 | Lieberman |
| 2006/0089657 A1 | 4/2006 | Broers et al. |
| 2006/0094958 A1 | 5/2006 | Marquart et al. |
| 2006/0122491 A1 | 6/2006 | Murray et al. |
| 2006/0142656 A1 | 6/2006 | Malackowski et al. |
| 2006/0142657 A1 | 6/2006 | Quaid et al. |
| 2006/0149276 A1 | 7/2006 | Grimm |
| 2006/0161051 A1 | 7/2006 | Terrill-Grisoni et al. |
| 2006/0184177 A1 | 8/2006 | Echeverri |
| 2006/0217733 A1 | 9/2006 | Plassky et al. |
| 2006/0217734 A1 | 9/2006 | Sanford et al. |
| 2006/0241639 A1 | 10/2006 | Kuczynski et al. |
| 2006/0270949 A1 | 11/2006 | Mathie et al. |
| 2006/0282023 A1 | 12/2006 | Leitner |
| 2007/0016009 A1 | 1/2007 | Lakin et al. |
| 2007/0032748 A1 | 2/2007 | McNeil et al. |
| 2007/0043287 A1 | 2/2007 | Degraaf |
| 2007/0043375 A1 | 2/2007 | Anissian |
| 2007/0073296 A1 | 3/2007 | Panchbhavi |
| 2007/0100346 A1 | 5/2007 | Wyss et al. |
| 2007/0162142 A1 | 7/2007 | Stone |
| 2007/0179626 A1 | 8/2007 | de la Barrera et al. |
| 2007/0179628 A1 | 8/2007 | Rochetin |
| 2007/0219559 A1 | 9/2007 | Heavener et al. |
| 2007/0219561 A1 | 9/2007 | Lavallee et al. |
| 2007/0226986 A1 | 10/2007 | Park et al. |
| 2007/0244488 A1 | 10/2007 | Metzger et al. |
| 2007/0249967 A1 | 10/2007 | Buly et al. |
| 2007/0270718 A1 | 11/2007 | Rochetin et al. |
| 2007/0270973 A1 | 11/2007 | Johnson et al. |
| 2007/0287911 A1 | 12/2007 | Haid et al. |
| 2007/0293869 A1 | 12/2007 | Conte et al. |
| 2008/0039868 A1 | 2/2008 | Tuemmler et al. |
| 2008/0058945 A1 | 3/2008 | Hajaj et al. |
| 2008/0071195 A1 | 3/2008 | Cuellar et al. |
| 2008/0103509 A1 | 5/2008 | Goldbach |
| 2008/0108912 A1 | 5/2008 | Node-Langlois |
| 2008/0162074 A1 | 7/2008 | Schneider |
| 2008/0183179 A1 | 7/2008 | Siebel et al. |
| 2008/0195109 A1 | 8/2008 | Hunter et al. |
| 2008/0202200 A1 | 8/2008 | West |
| 2008/0211768 A1 | 9/2008 | Breen et al. |
| 2008/0243127 A1 | 10/2008 | Lang et al. |
| 2008/0249394 A1 | 10/2008 | Giori et al. |
| 2008/0262812 A1 | 10/2008 | Arata et al. |
| 2008/0275451 A1 | 11/2008 | McAllister et al. |
| 2008/0281328 A1 | 11/2008 | Lang et al. |
| 2008/0285805 A1 | 11/2008 | Luinge et al. |
| 2009/0000626 A1 | 1/2009 | Quaid et al. |
| 2009/0000627 A1 | 1/2009 | Quaid et al. |
| 2009/0012532 A1 | 1/2009 | Quaid et al. |
| 2009/0040224 A1 | 2/2009 | Igarashi et al. |
| 2009/0070038 A1 | 3/2009 | Geelen et al. |
| 2009/0076507 A1 | 3/2009 | Claypool et al. |
| 2009/0076519 A1 | 3/2009 | Iversen |
| 2009/0088753 A1 | 4/2009 | Aram et al. |
| 2009/0099665 A1 | 4/2009 | Taylor et al. |
| 2009/0138019 A1 | 5/2009 | Wasielewski |
| 2009/0171370 A1 | 7/2009 | Yoon et al. |
| 2009/0209884 A1 | 8/2009 | Van Vorhis et al. |
| 2009/0216247 A1 | 8/2009 | Collette |
| 2009/0216285 A1 | 8/2009 | Ek |
| 2009/0234360 A1 | 9/2009 | Alexander |
| 2009/0247863 A1 | 10/2009 | Proulx et al. |
| 2009/0248044 A1 | 10/2009 | Amiot et al. |
| 2009/0264737 A1 | 10/2009 | Haechler et al. |
| 2009/0270864 A1 | 10/2009 | Poncet |
| 2009/0270865 A1 | 10/2009 | Poncet et al. |
| 2009/0270868 A1 | 10/2009 | Park et al. |
| 2009/0270869 A1 | 10/2009 | Colquhoun et al. |
| 2009/0270874 A1 | 10/2009 | Santarella et al. |
| 2009/0270875 A1 | 10/2009 | Poncet |
| 2009/0270928 A1 | 10/2009 | Stone et al. |
| 2009/0276054 A1 | 11/2009 | Clifford et al. |
| 2009/0281545 A1 | 11/2009 | Stubbs |
| 2009/0289806 A1 | 11/2009 | Thornberry |
| 2009/0292227 A1 | 11/2009 | Scholten et al. |
| 2009/0299416 A1 | 12/2009 | Haenni et al. |
| 2009/0299483 A1 | 12/2009 | Amirouche et al. |
| 2009/0306679 A1 | 12/2009 | Murphy |
| 2009/0312973 A1 | 12/2009 | Hatlestad et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0324078 A1 | 12/2009 | Wu et al. |
| 2010/0016705 A1 | 1/2010 | Stone |
| 2010/0023018 A1 | 1/2010 | Theofilos |
| 2010/0063508 A1 | 3/2010 | Borja et al. |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0087829 A1 | 4/2010 | Metzger et al. |
| 2010/0100011 A1 | 4/2010 | Roche |
| 2010/0100154 A1 | 4/2010 | Roche |
| 2010/0113980 A1 | 5/2010 | Herr et al. |
| 2010/0121334 A1 | 5/2010 | Couture et al. |
| 2010/0137869 A1 | 6/2010 | Borja et al. |
| 2010/0137871 A1 | 6/2010 | Borja |
| 2010/0153081 A1 | 6/2010 | Bellettre et al. |
| 2010/0179605 A1 | 7/2010 | Branch et al. |
| 2010/0182914 A1 | 7/2010 | DelRegno et al. |
| 2010/0192662 A1 | 8/2010 | Yanni |
| 2010/0198067 A1 | 8/2010 | Mahfouz et al. |
| 2010/0198275 A1 | 8/2010 | Chana |
| 2010/0204551 A1 | 8/2010 | Roche |
| 2010/0204575 A1 | 8/2010 | Roche et al. |
| 2010/0204955 A1 | 8/2010 | Roche et al. |
| 2010/0211077 A1 | 8/2010 | Couture et al. |
| 2010/0239996 A1 | 9/2010 | Ertl |
| 2010/0241126 A1 | 9/2010 | Ghijselings |
| 2010/0249533 A1 | 9/2010 | Pierce et al. |
| 2010/0249534 A1 | 9/2010 | Pierce et al. |
| 2010/0249535 A1 | 9/2010 | Pierce et al. |
| 2010/0249659 A1 | 9/2010 | Sherman et al. |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0250276 A1 | 9/2010 | Pierce et al. |
| 2010/0250284 A1 | 9/2010 | Roche et al. |
| 2010/0250571 A1 | 9/2010 | Pierce et al. |

(56)          References Cited

U.S. PATENT DOCUMENTS

| | | |
|---|---|---|
| 2010/0256504 A1 | 10/2010 | Moreau-Gaudry et al. |
| 2010/0261998 A1 | 10/2010 | Stiehl |
| 2010/0268067 A1 | 10/2010 | Razzaque et al. |
| 2010/0298661 A1 | 11/2010 | McCombie et al. |
| 2010/0324457 A1 | 12/2010 | Bean et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331633 A1 | 12/2010 | Stein |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331683 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331735 A1 | 12/2010 | Stein |
| 2010/0331736 A1 | 12/2010 | Stein |
| 2010/0331737 A1 | 12/2010 | Stein et al. |
| 2010/0331738 A1 | 12/2010 | Stein et al. |
| 2010/0331894 A1 | 12/2010 | Stein |
| 2010/0332152 A1 | 12/2010 | Stein |
| 2011/0028865 A1 | 2/2011 | Luinge et al. |
| 2011/0032184 A1 | 2/2011 | Roche et al. |
| 2011/0093081 A1 | 4/2011 | Chana |
| 2011/0208093 A1 | 8/2011 | Gross et al. |
| 2011/0213275 A1 | 9/2011 | Boos et al. |
| 2011/0218458 A1 | 9/2011 | Valin et al. |
| 2011/0218543 A1 | 9/2011 | van der Walt |
| 2011/0218546 A1 | 9/2011 | De La Fuente Klein et al. |
| 2011/0275957 A1 | 11/2011 | Bhandari |
| 2012/0022406 A1 | 1/2012 | Hladio et al. |
| 2012/0029389 A1 | 2/2012 | Amiot et al. |
| 2012/0053488 A1 | 3/2012 | Boutin et al. |
| 2012/0053594 A1 | 3/2012 | Pelletier et al. |
| 2012/0093377 A1 | 4/2012 | Tsougarakis et al. |
| 2012/0110810 A1 | 5/2012 | Houser et al. |
| 2012/0130279 A1 | 5/2012 | Stone |
| 2012/0157887 A1 | 6/2012 | Fanson et al. |
| 2012/0172712 A1 | 7/2012 | Bar-Tal |
| 2012/0172884 A1 | 7/2012 | Zheng et al. |
| 2012/0203140 A1 | 8/2012 | Malchau et al. |
| 2012/0209117 A1 | 8/2012 | Mozes et al. |
| 2012/0239555 A1 | 9/2012 | Seethaler et al. |
| 2012/0283599 A1 | 11/2012 | Borja |
| 2012/0316567 A1 | 12/2012 | Gross et al. |
| 2013/0046310 A1 | 2/2013 | Ranawat et al. |
| 2013/0053859 A1 | 2/2013 | Penenberg |
| 2013/0064478 A1 | 3/2013 | Sold et al. |
| 2013/0066323 A1 | 3/2013 | Nycz et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079790 A1 | 3/2013 | Stein et al. |
| 2013/0079791 A1 | 3/2013 | Stein et al. |
| 2013/0079793 A1 | 3/2013 | Stein et al. |
| 2013/0190887 A1 | 7/2013 | Fanson et al. |
| 2013/0274633 A1 | 10/2013 | Hladio et al. |
| 2014/0005531 A1 | 1/2014 | Taylor |
| 2014/0005673 A1 | 1/2014 | Pelletier et al. |
| 2014/0031672 A1 | 1/2014 | McCaulley et al. |
| 2014/0052149 A1 | 2/2014 | van der Walt et al. |
| 2014/0114179 A1 | 4/2014 | Muller et al. |
| 2014/0134586 A1 | 5/2014 | Stein et al. |
| 2014/0135658 A1 | 5/2014 | Hladio et al. |
| 2014/0135744 A1 | 5/2014 | Stein et al. |
| 2014/0135773 A1 | 5/2014 | Stein et al. |
| 2014/0136143 A1 | 5/2014 | Stein et al. |
| 2014/0165796 A1 | 6/2014 | Gauthier et al. |
| 2014/0182062 A1 | 7/2014 | Aghazadeh |
| 2014/0224685 A1 | 8/2014 | Carnevali |
| 2014/0268516 A1 | 9/2014 | Fathollahi et al. |
| 2014/0270583 A1 | 9/2014 | Anderson |
| 2014/0275940 A1 | 9/2014 | Hladio et al. |
| 2014/0276000 A1 | 9/2014 | Mullaney et al. |
| 2014/0276864 A1 | 9/2014 | Aghazadeh |
| 2014/0303631 A1 | 10/2014 | Thornberry |
| 2014/0330281 A1 | 11/2014 | Aghazadeh |
| 2014/0364858 A1 | 12/2014 | Li et al. |
| 2015/0018718 A1 | 1/2015 | Aghazadeh |
| 2015/0100058 A1 | 4/2015 | van der Walt et al. |
| 2015/0127009 A1 | 5/2015 | Berend et al. |
| 2015/0142372 A1 | 5/2015 | Singh |
| 2015/0143781 A1 | 5/2015 | Agnihotri |
| 2015/0150569 A1 | 6/2015 | van der Walt et al. |
| 2015/0164657 A1 | 6/2015 | Miles et al. |
| 2015/0238204 A1 | 8/2015 | Stone |
| 2015/0245914 A1 | 9/2015 | Langton |
| 2015/0272478 A1 | 10/2015 | Borja |
| 2015/0313723 A1 | 11/2015 | Jansen |
| 2015/0342516 A1 | 12/2015 | Nguyen et al. |
| 2016/0038242 A1 | 2/2016 | Lo Iacono et al. |
| 2016/0166321 A1 | 6/2016 | Amsler |
| 2016/0175055 A1 | 6/2016 | Hook et al. |
| 2016/0206378 A1 | 7/2016 | Flett et al. |
| 2016/0213383 A1 | 7/2016 | van der Walt et al. |
| 2016/0220315 A1 | 8/2016 | Falardeau |
| 2016/0220318 A1 | 8/2016 | Falardeau et al. |
| 2016/0220385 A1 | 8/2016 | Falardeau et al. |
| 2016/0242934 A1 | 8/2016 | van der Walt et al. |
| 2016/0278943 A1 | 9/2016 | van der Walt et al. |
| 2016/0346044 A1 | 12/2016 | Brown et al. |
| 2017/0035166 A1 | 2/2017 | Zondervan |
| 2017/0119475 A1 | 5/2017 | McCabe et al. |
| 2017/0238946 A1 | 8/2017 | van der Walt et al. |
| 2017/0296203 A1 | 10/2017 | Stone |
| 2017/0325892 A1 | 11/2017 | Aghazadeh |
| 2017/0367766 A1 | 12/2017 | Mahfouz |
| 2018/0028322 A1 | 2/2018 | Sharkey et al. |
| 2018/0064496 A1 | 3/2018 | Hladio et al. |
| 2018/0177509 A1 | 6/2018 | Trabish et al. |
| 2018/0193171 A1 | 7/2018 | van der Walt et al. |
| 2018/0206860 A1 | 7/2018 | van der Walt et al. |
| 2018/0235762 A1 | 8/2018 | Radermacher et al. |
| 2018/0296232 A1* | 10/2018 | Nielsen ................. A61B 17/155 |
| 2018/0296365 A1 | 10/2018 | Nielsen et al. |
| 2019/0328549 A1 | 10/2019 | van der Walt et al. |
| 2019/0350728 A1 | 11/2019 | van der Walt et al. |
| 2019/0357809 A1 | 11/2019 | Borja et al. |
| 2020/0352654 A1 | 11/2020 | van der Walt et al. |
| 2020/0390501 A1 | 12/2020 | Brown et al. |
| 2021/0153880 A1 | 5/2021 | Nielsen et al. |
| 2021/0153908 A1 | 5/2021 | van der Walt et al. |
| 2021/0186711 A1 | 6/2021 | van der Walt et al. |
| 2021/0220152 A1 | 7/2021 | Nielsen et al. |
| 2021/0315716 A1 | 10/2021 | van der Walt et al. |
| 2022/0071509 A1 | 3/2022 | Borja et al. |
| 2022/0240953 A1 | 8/2022 | Stone |
| 2022/0313455 A1 | 10/2022 | van der Walt et al. |
| 2022/0378516 A1 | 12/2022 | Sierra et al. |
| 2023/0135541 A1 | 5/2023 | Borja et al. |
| 2023/0149185 A1 | 5/2023 | Nielsen et al. |
| 2023/0157727 A1 | 5/2023 | van der Walt et al. |
| 2023/0248447 A1 | 8/2023 | van der Walt et al. |
| 2023/0277335 A1 | 9/2023 | van der Walt et al. |
| 2023/0301685 A1 | 9/2023 | van der Walt et al. |
| 2023/0414292 A1 | 12/2023 | Roger et al. |
| 2024/0099731 A1 | 3/2024 | Nielsen et al. |
| 2024/0099744 A1 | 3/2024 | van der Walt et al. |
| 2024/0197406 A1 | 6/2024 | van der Walt et al. |
| 2024/0299099 A1 | 9/2024 | Walter et al. |
| 2024/0315749 A1 | 9/2024 | Walter et al. |
| 2025/0017745 A1 | 1/2025 | van der Walt et al. |
| 2025/0082413 A1 | 3/2025 | van der Walt et al. |

(56)                References Cited

U.S. PATENT DOCUMENTS

| | | | |
|---|---|---|---|
| 2025/0152039 A1 | 5/2025 | Borja |
| 2025/0152204 A1 | 5/2025 | van der Walt et al. |
| 2025/0345187 A1 | 11/2025 | van der Walt et al. |
| 2025/0352361 A1 | 11/2025 | van der Walt et al. |

FOREIGN PATENT DOCUMENTS

| | | |
|---|---|---|
| CA | 2 537 711 | 8/2007 |
| CN | 109846528 | 6/2019 |
| DE | 4 225 112 | 12/1993 |
| DE | 29704393 | 8/1997 |
| DE | 198 30 359 | 1/2000 |
| DE | 20116368 | 12/2001 |
| EP | 0 557 591 | 9/1993 |
| EP | 0 651 968 | 5/1995 |
| EP | 1 635 705 | 3/2006 |
| EP | 1 817 547 | 4/2012 |
| EP | 2 491 873 | 8/2012 |
| EP | 2 957 249 | 12/2015 |
| EP | 3 395 281 | 10/2018 |
| EP | 4 287 980 | 12/2023 |
| GB | 2 197 790 | 6/1988 |
| GB | 2 511 885 | 9/2014 |
| JP | 07-184929 | 7/1995 |
| JP | H08-240611 | 9/1996 |
| JP | 2004-237064 | 8/2004 |
| JP | 2004-529679 | 9/2004 |
| JP | 2006-314775 | 11/2006 |
| JP | 2006-528496 | 12/2006 |
| JP | 2007-503289 | 2/2007 |
| JP | 2007-534351 | 11/2007 |
| JP | 2008-521574 | 6/2008 |
| JP | 2008-537496 | 9/2008 |
| JP | 2009-511136 | 3/2009 |
| JP | 2011-502626 | 1/2011 |
| JP | 2013-000230 | 1/2013 |
| JP | 2014-524815 | 9/2014 |
| JP | 2015-524733 | 8/2015 |
| JP | 2015-226613 | 12/2015 |
| JP | 6980248 | 11/2021 |
| JP | 7180159 | 11/2022 |
| WO | WO 99/60939 | 12/1999 |
| WO | WO 2001/030247 | 5/2001 |
| WO | WO 02/000131 | 1/2002 |
| WO | WO 02/17798 | 3/2002 |
| WO | WO 2004/080323 | 9/2004 |
| WO | WO 2004/112610 | 12/2004 |
| WO | WO 2005/006993 | 1/2005 |
| WO | WO 2006/119387 | 11/2006 |
| WO | WO 2007/136784 | 11/2007 |
| WO | WO 2008/073999 | 6/2008 |
| WO | WO 2008/129414 | 10/2008 |
| WO | WO 2009/117833 | 10/2009 |
| WO | WO 2010/011978 | 1/2010 |
| WO | WO 2010/030809 | 3/2010 |
| WO | WO 2010/063117 | 6/2010 |
| WO | WO 2011/044273 | 4/2011 |
| WO | WO 2012/006172 | 1/2012 |
| WO | WO 2012/027815 | 3/2012 |
| WO | WO 2012/027816 | 3/2012 |
| WO | WO 2012/082164 | 6/2012 |
| WO | WO 2012/109361 | 8/2012 |
| WO | WO 2012/113054 | 8/2012 |
| WO | WO 2013/012561 | 1/2013 |
| WO | WO 2013/013094 | 1/2013 |
| WO | WO 2013/049534 | 4/2013 |
| WO | WO 2013/169674 | 11/2013 |
| WO | WO 2013/173700 | 11/2013 |
| WO | WO 2013/188960 | 12/2013 |
| WO | WO 2014/028227 | 2/2014 |
| WO | WO 2014/063181 | 5/2014 |
| WO | WO 2014/197988 | 12/2014 |
| WO | WO 2015/054745 | 4/2015 |
| WO | WO 2016/070288 | 5/2016 |
| WO | WO 2016/134168 | 8/2016 |
| WO | WO 2016/147153 | 9/2016 |
| WO | WO 2016/154489 | 9/2016 |
| WO | WO 2017/093769 | 6/2017 |
| WO | WO 2018/085900 | 5/2018 |
| WO | WO 2018/119360 | 6/2018 |
| WO | WO 2018/169980 | 9/2018 |
| WO | WO 2018/169995 | 9/2018 |
| WO | WO 2019/036752 | 2/2019 |
| WO | WO 2021/119001 | 6/2021 |
| WO | WO 2021/188798 | 9/2021 |
| WO | WO 2022/165561 | 8/2022 |
| WO | WO 2024/108260 | 5/2024 |

OTHER PUBLICATIONS 510 (k) Summary for Total Knee Surgetics Navigation System, in 5 pages.
510 (k) Summary of Safety and Effectiveness for BrainLAB knee, in 5 pages.
Anderson MD., Kevin, et al., "Computer Assisted Navigation in Total Knee Arthroplasty", The Journal of Arthroplasty, 2005, vol. 20, No. 7, Suppl. 3, in 7 pages.
Ang, et al., An Active Hand-Held Instrument for Enhanced Micro-surgical Accuracy, Medical Image Computing and Computer-Assisted Intervention, 2000, vol. 1935, pp. 878-887.
Arnold-Moore, et al., Architecture of a Content Management Server for XML DocumentApplications, RMIT Multimedia Database Systems, Royal Melbourne Institute of Technology, Victoria Australia, in 12 pages.
ArthroCAD, Enhancing orthopedic outcomes through optimal alignment, 2012, Pages in 2 pages.
Bae et al., "Computer Assisted Navigation in Knee Arthroplasty", Clinics in Orthopedic Surgery, 2011, vol. 3, pp. 259-267.
Bargren, MD., et al.,, Alignment in Total Knee Arthroplasty, Correlated Biomechanical and Clinical Observations, Clinical Orthopaedics and Related Research, Mar. 1, 1983, Issue 173, pp. 178-183, Philadelphia.
Bathis, H. et al., "Alignment in total knee arthroplasty", The Journal of Bone & Joint Surgery (Br), 2004, 86-B, pp. 682-687, British Editorial.
Bhandari, Design and Prototype of a Computer Assisted Surgical Navigation System for Total Knee Replacement Surgery, May 12, 2009, Pages in 294 pages.
Biomet Orthopedics, Inc, Vision Acetabular Surgical Techniques, website brochure, pp. 16 pages.
Biomet Orthopedics, Inc., Universal Ringlock® Acetabular Series, vol. website brochure, pp. 13 pages.
Brainlab, "Position Determination and Calibration in optical tracking systems", Florenus the technology merchants, in 2 pages.
Brainlab, "Tracking and imaging in Navigation", Florenus, in 2 pages.
Brennan, et al., Quantification of Inertial Sensor-Based 3D Joint Angle Measurement Accuracy Using and Instrumented Gimbal, Gait & Posture, May 23, 2011, vol. 34, pp. 320-323.
Chauhan, et al., Computer-Assisted Knee Arthroplasty Versus a Conventional Jig-Based Technique, The Journal of Bone & Joint Surgery, 2004, vol. 86-B, pp. 372-377.
Cutti, et al., Motion Analysis of the Upper-Limb Based on Inertial Sensors: Part 1—Protocol Description, Journal of Biomechanics, Jan. 1, 2007, vol. 40, pp. S250.
Decking, MD., et al., Leg Axis After Computer-Navigated Total Knee Arthroplasty, The Journal of Arthroplasty, 2005, vol. 20, Issue 3, pp. 282-288.
Depuy, Johnson & Johnson, Co.,, Summit Cemented Hip System, website brochure, pp. 21 pages.
De Momi, et al., "In-vitro experimental assessment of a new robust algorithm for hip joint centre estimation", Journal of Biomechanics, Feb. 26, 2009, vol. 42, pp. 989-995.
Digioia III, MD., et al., "Comparison of a Mechanical Acetabular Alignment Guide with Computer Placement of the Socket", The Journal of Arthroplasty, Apr. 2002, vol. 17, No. 3, in 6 pages.

(56) References Cited

OTHER PUBLICATIONS

Eric Foxlin, Chapter 7. Motion Tracking Requirements and Technologies, Handbook of Virtual Environment Technology, 2002, vol. Kay Stanney, Ed., Issue Lawrence Erlbaum Ass.

Favre, et al., 3D Evaluation of the Knee Joint Using Ambulatory System: Application to ACL-Deficient Knees, Journal of Biomechanics, Jan. 1, 2007, vol. 40, pp. S251.

Favre, et al., A New Ambulatory System for Comparative Evaluation of the Three-Dimensional Knee Kinematics, Applied to Anterior Cruciate Ligament Injuries, Knee Surgery, Sports Traumatology, Arthroscopy, Jan. 19, 2006, vol. 14, pp. 592-604.

Favre, et al., Ambulatory Measurement of 3D Knee Joint Angle, Journal of Biomechanics, Jan. 28, 2008, vol. 41, Issue 1029-1035.

Fixed Reference Surgical Technique, SIGMA High Performance Instruments, DePuy Orthopaedics, Inc., 2008, Warsaw, IN, in 52 pages.

Ganapathi et al., "Limb Length and Femoral Offset Reconstruction During THA Using CT-Free Computer Navigation", The Journal of Bone and Joint Surgery, 2009, vol. 91-B, Supplement III, p. 399.

Goniometer, AllHeart.com, 2004, website: http://allheart.com/allheart, (1 page).

Haaker et al., "Computer-Assisted Navigation Increases Precision of Component Placement in Total Knee Arthroplasty", Clinical Orthopaedics and Related Research, Apr. 2005, vol. 433, pp. 152-159.

Hofstetter, Ph.D., et al., "Computer-Assisted Fluoroscopy-Based Reduction of Femoral Fractures and Antetorsion Correction", Computer Aided Surgery, 2000, vol. 5, pp. 311-325, Wiley-Liss, Inc.

Hsieh, Pang-Hsin, et al., "Image-guided periacetabular osteotomy: computer-assisted navigation compared with the conventional technique: A randomized study of 36 patients followed for 2 years", Acta Orthopaedica, Aug. 1, 2006, 77:4, pp. 591-597.

iASSIST Knee, Surgical Technique, Zimmer, Inc., 2012.

International Search Report and Written Opinion issued in PCT Application No. PCT/US2021/022973, dated Aug. 12, 2021, in 13 pages.

Jenny, et al., Computer-Assisted Implantation of Total Knee Prosthesis: A Case-Control Comparative Study with Classical Instrumentation, Computer Aided Surgery, 2001, vol. 6, pp. 217-220.

Konyves et al., "The importance of leg length discrepancy after total hip arthroplasty", The Journal of Bone & Joint Surgery (Br), Feb. 2005, vol. 87-B, No. 2, pp. 155-157.

Leenders, MD., et al., "Reduction in Variability of Acetabular Cup Abduction Using Computer Assisted Surgery: A Prospective and Randomized Study", Computer Aided Surgery, 2002, vol. 7, pp. 99-106.

Leung, et al., Intraobserver Errors in Obtaining Visually Selected Anatomic Landmarks During Registration Process in Nonimage-based Navigation-assisted Total Knee Arthroplasty, The Journal of Arthroplasty, 2005, vol. 20, Issue 5, pp. 591-601.

Liebergall, Meir, et al., "Computerized Navigation for the Internal Fixation of Femoral Neck Fractures", The Journal of Bone & Joint Surgery Am, 2006, vol. 88, pp. 1748-1754.

Longo, et al., MIKA Surgical Technique, DJO Surgical, 2008, Austin Texas in 14 pages.

Luinge, Inertial Sensing of Human Movement, Twente University Press, Feb. 15, 1973, Pages in 88 pages.

Mackenzie, et al., A Two-Ball Mouse Affords Three Degrees of Freedom, Extended Abstracts of the CHI '97 Conference on Human Factors in Compounding Systems (as printed from the internet on Jun. 13, 2012 URL: http://www.yorku.ca/mack/CHI97a.htm), 1997, pp. 303-304.

Medical Research Ltd, Clinical Goniometer, http://www.mie-uk.com/Gonio, 1997, pp. 1 page.

Minimally Invasive TKA Genesis II Anterior Cut First, Surgical Technique, Smith & Nephew, Nov. 2003, Memphis TN, in 16 pages.

Noble et al., "Computer Simulation: How Can it Help the Surgeon Optimize Implant Position?", Clinical Orthopaedics and Related Research, Dec. 2003, vol. 417, pp. 242-252.

Parratte, Sebastien, et al., "Validation and Usefulness of a Computer-Assisted Cup-Positioning System in Total Hip Arthroplasty. A Prospective, Randomized, Controlled Study", The Journal of Bone & Joint Surgery Am, 2007, vol. 89, pp. 494-499.

Perseus Intelligent Cutting Guide, Orthokey, Product Guide, in 8 pages.

Perseus Intelligent Cutting Guide, Smart Instruments for Knee Arthroplasty, Orthokey, in 2 pages.

Ritter, M.D., et al., Postoperative Alignment of Total Knee Replacement, Its Effect on Survival, Clinical Orthopaedics and Related Research, Feb. 1, 1994, Issue 299, pp. 153-156, Philadelphia.

Rocon, et al., Application of Inertial Sensors and Rehabilitation Robotics, Rehabilitation Robotics 2007, Jun. 1, 2007, pp. 145-150.

Sacks-Davis et al., Atlas: A nested Relational Database System for Text Applications, IEEE Transactions on Knowledge and Data Engineering, v.7, n.3, Jun. 1995, pp. 454-470.

Schep, et al., "Computer assisted orthopaedic and trauma surgery State of the art and future perspectives", Injury Int. J. Care Injured 34, (website: www.elsevier.com/locate/injury), 2003 pp. 299-306.

Scott, M.S., et al., P.F.C. Sigma Knee System, Primary Surgical Technique Part 1 of 2, DePuy International Ltd., 2003, England, (up to p. 44), in 48 pages.

Scott, M.S., et al., P.F.C. Sigma Knee System, Primary Surgical Technique Part 2 of 2, DePuy International Ltd., 2003, England, Part A (up to p. 74), in 31 pages. (This reference was split in two due to size exceeding over 25MB).

Scott, M.S., et al., P.F.C. Sigma Knee System, Primary Surgical Technique Part 2 of 2, DePuy International Ltd., 2003, England, Part B (up to p. 104), in 31 pages. (This reference was split in two due to size exceeding over 25MB).

Sikorski et al., "Computer-Assisted Orthopaedic Surgery: Do We Need CAOS?", The Journal of Bone & Joint Surgery (Br), Apr. 2003, vol. 85-B, No. 3, pp. 319-323.

Slomczykowski, et al., "Novel Computer-Assisted Fluoroscopy System for Intraoperative Guidance:Feasibility Study for Distal Locking of Femoral Nails", Journal of Orthopaedic Trauma, 2001, vol. 15, No. 2, pp. 122-131, Lippincott Williams & Wilkins, Inc., Philadelphia.

Stulberg, et al., Computer-Assisted Total Knee Replacement Arthroplasty, Operative Techniques in Orthopaedics, Jan. 2000, vol. 10, Issue 1, pp. 25-39.

Supplementary European Search Report issued in European Patent Application No. 13829614.0, dated Sep. 22, 2016, in 8 pages.

The Academy of Orthopaedic Surgeons, Academy News, http://www.aaos.org/wordhtml/2001news/b6-01.htm, Mar. 1, 2001, pp. 1 page.

Tilt Sensors: High Accuracy, Digital Series, Crossbow Technology, Inc., pp. 32-35.

Upadhyay et al., "Medical Malpractice in Hip and Knee Arthroplasty", The Journal of Arthroplasty, 2007, vol. 22, No. 6, Suppl. 2, pp. 2-7.

Visser, et al., 3D Analysis of Upper Body Movements in Bilateral Amputee Gait Using Inertial Sensors, Journal of Biomechanics, Jan. 1, 2007, vol. 40, Issue S509.

Wentzensen et al., "Image-based hip navigation", International Orthopaedics (SICOT), 2003, vol. 27 (Suppl. 1), pp. S43-S46.

Wolfstadt et al., "An intelligent instrument for improved leg length and hip offset accuracy in total hip arthroplasty", Abstract Only.

Wylde et al., "Prevalence and functional impact of patient-perceived leg length discrepancy after hip replacement", International Orthopaedics, 2009, vol. 33, pp. 905-909.

Wylde et al., "Patient-perceived leg length discrepancy after total hip replacement: prevalence and impact on functional outcome", International Orthopaedics, 2008, vol. 24, No. 2, pp. 210-216.

Zheng et al., "Technical Principles of Computer Assisted Orthopaedic Surgery", Suomen Ortopedia ja Traumatologia, Feb. 2008, vol. 31, pp. 135-147.

Zhou, et al., Use of Multiple Wearable Inertial Sensors in Upper Limb Motion Tracking, Medical Engineering & Physics, Jan. 1, 2008, vol. 30, pp. 123-133.

Zimmer NexGen Flexion Balancing Instruments, Surgical Technique, 2007, www.zimmer.com, in 44 pages.

(56) References Cited

OTHER PUBLICATIONS

Zorman, David, et al., "Computer-assisted total knee arthroplasty: comparative results in a preliminary series of 72 cases", ActaOrthop. Belg., 2005, 71, pp. 696-702.

\* cited by examiner

Femoral Axis Registration

Tibial Axis Registration

SYSTEMS AND METHODS FOR LIMB ALIGNMENT

INCORPORATION BY REFERENCE TO ANY PRIORITY APPLICATIONS

This application is a continuation of International Application No. PCT/US2021/022973, filed Mar. 18, 2021, which claims the benefit under 35 U.S.C. § 119(e) to U.S. Provisional Application No. 62/992,537, filed Mar. 20, 2020, which are hereby incorporated by reference in their entirety. Any and all applications for which a foreign or domestic priority claim is identified in the Application Data Sheet as filed with the present application is hereby incorporated by reference in its entirety under 37 CFR 1.57.

BACKGROUND OF THE INVENTION

Field of the Invention

The present application is directed to systems and methods for joint assessment and replacement, in particular to systems and methods for knee and other limb joint assessment and replacement that utilize one or more inertial devices to measure limb alignment.

Description of the Related Art

Joint replacement procedures, including knee joint replacement procedures, are commonly used to replace a patient's joint with a prosthetic joint component or components. Such procedures often use a system or systems of surgical tools and devices, including but not limited to cutting guides (e.g. cutting blocks) and surgical guides, to make surgical cuts along a portion or portions of the patient's bone(s).

Current systems and methods may use expensive, complex, bulky, and/or massive computer navigation systems which require a computer or computers, as well as three dimensional imaging, to track a spatial location and/or movement of a surgical instrument or landmark in the human body. These systems are used generally to assist a user to determine where in space a tool or landmark is located, and often require extensive training, cost, and room.

Where such complex and costly systems are not used, simple methods are used, such as "eyeballing" the alignment of rods with anatomical features, including leg bones. These simple methods are not sufficiently accurate to reliably align and place prosthetic implant components and the bones to which such components are attached.

SUMMARY

Accordingly, there is a lack of devices, systems and methods that can be used to assess joint characteristics such as relative alignment of bones of the joint and soft tissue condition in connection with selecting and accurately positioning components of prosthetic joints without overly complicating the procedures, crowding the medical personnel, and/or burdening the physician or health-care facility with the great cost of complex navigation systems.

In some embodiments, a system for limb alignment is provided. The system can include a first orientation device configured to be coupled with a tibia, the first orientation device comprising at least one inertial sensor. The system can include a second orientation device configured to be coupled with a femur, the second orientation device comprising at least one inertial sensor. In some embodiments, the first orientation device or the second orientation device comprise a processor configured to receive inertial sensor data, wherein the processor is configured to calculate an angle between a femoral mechanical axis and a tibial mechanical axis.

In some embodiments, the system can include a tibial preparation system comprising a probe member. In some embodiments, the system can include a tibial preparation system comprising a midline reference probe assembly. In some embodiments, the system can include a tibial preparation system comprising a first device interface configured to couple to the first orientation device and a second device interface configured to couple to the second orientation device. In some embodiments, the system can include a femoral preparation system comprising a device interface configured to couple to the second orientation device. In some embodiments, the system can include a femoral preparation system comprising a cutting guide bracket configured to slide relative to a tibial preparation system. In some embodiments, the system can include a femoral preparation system comprising a swivel post configured to swivel relative to a tibial preparation system. In some embodiments, the system can include a femoral preparation system comprising an extension configured to be positioned relative to a threaded pin coupled to a portion of the distal femur. In some embodiments, the system can include a femoral preparation system comprising a connector configured to be mounted to a lateral portion of the femur. In some embodiments, the system can include a femoral preparation system comprising a connector comprising a device interface configured to couple to the second orientation device. In some embodiments, wherein the processor is configured to determine the femoral mechanical axis and the tibial mechanical axis based at least in part on the location of anatomical landmarks. In some embodiments, wherein the processor is configured to determine the femoral mechanical axis and the tibial mechanical axis based at least in part on movement of the femur. In some embodiments, wherein the processor is configured to determine varus/valgus angle of the femoral mechanical axis and the tibial mechanical axis. In some embodiments, wherein the processor is configured to determine flexion/extension angle of the femoral mechanical axis and the tibial mechanical axis. In some embodiments, wherein the processor is configured to determine a gap measurement.

In some embodiments, a method for determining limb alignment is provided. The method can include coupling a first orientation device configured with a tibia, the first orientation device comprising at least one inertial sensor. The method can include coupling a second orientation device configured with a femur, the second orientation device comprising at least one inertial sensor. The method can include calculating a femoral mechanical axis and a tibial mechanical axis. The method can include measuring changes in the femoral mechanical axis and the tibial mechanical axis.

In some embodiments, the method can include performing a resection and positioning an implant. In some embodiments, measuring changes in the femoral mechanical axis and the tibial mechanical axis further comprises positioning the leg in extension. In some embodiments, the method can include calibrating the first orientation device and the second orientation device by mounting the first orientation device and the second orientation device on a tibial preparation system. In some embodiments, the method can include applying a force and measuring a gap distance.

In some embodiments, a system for limb alignment is provided. The system can include a first sensor configured to be coupled with a tibia, the first sensor comprising at least one inertial sensor. The system can include a second sensor configured to be coupled with a femur, the second sensor comprising at least one inertial sensor. The system can include a processor configured to receive outputs from one or more of the first sensor and the second sensor, wherein the processor is configured to calculate position and/or or orientation of the femoral mechanical axis and the tibial mechanical axis during movement.

In some embodiments, the system can include a surgical orientation device comprising the processor. In some embodiments, the surgical orientation device comprises a display. In some embodiments, the processor is configured to determine varus/valgus angles. In some embodiments, the processor is configured to determine varus angles at different flexion angles. In some embodiments, the processor is configured to determine axial rotation. In some embodiments, the processor is configured to determine flexion angles. In some embodiments, the processor is configured to determine an extension angle. In some embodiments, the processor is configured to provide a recommendation for a trial implant. In some embodiments, the processor is configured to determine the gap between the tibial and femoral plateau. In some embodiments, the processor is configured to determine the angle between the tibial and femoral plateau.

In some embodiments, a method for determining limb alignment is provided. The method can include coupling a first reference sensor with a first bone of a limb, the first reference sensor comprising at least one inertial sensor. The method can include coupling a second reference sensor with a second bone of a limb, a joint being formed between the first bone and the second bone, the second reference sensor comprising at least one inertial sensor. The method can include moving the limb to position the first bone in a plurality of positions differing in flexion, axial rotation, and/or varus-valgus relative to the second bone. The method can include outputting values indicative of limb alignment at or based on one or more of the positions.

In some embodiments, the limb is a leg and the first bone is a tibia and the second bone is a femur. In some embodiments, the method can include positioning a trial implant or implant on a resected surface of the tibia. In some embodiments, the method can include calibrating the first reference sensor and the second reference sensor. In some embodiments, outputting values comprise outputting varus/valgus angles. In some embodiments, outputting values comprise outputting varus angles at different flexion angles. In some embodiments, outputting values comprise outputting axial rotation. In some embodiments, outputting values comprise outputting flexion angles. In some embodiments, outputting values comprise outputting a gap measurement between tibial and femoral plateaus. In some embodiments, outputting values comprise outputting an angle between tibial and femoral plateau.

In some embodiments, a system for limb alignment is provided. The system can include a first orientation device configured to be coupled with a tibia, the first orientation device comprising at least one inertial sensor. The system can include a second orientation device configured to be coupled with a femur, the second orientation device comprising at least one inertial sensor. In some embodiments, the first orientation device and the second orientation device are configured to calculate a relative orientation between a femoral mechanical axis and a tibial mechanical axis when the leg is in extension.

In some embodiments, the first orientation device and the second orientation device are configured to calculate the relative orientation between the femoral mechanical axis and the tibial mechanical axis when the leg is in extension before resection. In some embodiments, the first orientation device and the second orientation device are configured to calculate the relative orientation between the femoral mechanical axis and the tibial mechanical axis when the leg is in extension after resection. In some embodiments, the first orientation device and the second orientation device are configured to calculate the relative orientation between the femoral mechanical axis and the tibial mechanical axis when the leg is in extension and an implant is positioned between the tibia and the femur. In some embodiments, the first orientation device and the second orientation device are configured to calculate the relative orientation between the femoral mechanical axis and the tibial mechanical axis when the leg is in extension and a force is applied. In some embodiments, a cutting block is positioned relative to the femoral mechanical axis. In some embodiments, a cutting block is positioned relative to the tibial mechanical axis. In some embodiments, the second orientation device is configured to be coupled with the femur at a fixed known point. In some embodiments, the second orientation device is configured to be coupled with the femur as the leg is moved from flexion to extension. In some embodiments, the femoral mechanical axis and the tibial mechanical axis are two vectors in a three dimensional coordinate system. In some embodiments, the first orientation device and the second orientation device are configured to determine an angulation in the joint. In some embodiments, the first orientation device and the second orientation device are configured to determine a mechanical axis of the leg. In some embodiments, the first orientation device and the second orientation device are configured to determine an angle in the sagittal plane. In some embodiments, the first orientation device and the second orientation device are configured to determine an angle in the coronal plane. In some embodiments, the first orientation device is configured to calculate the tibial mechanical axis. In some embodiments, the first orientation device is configured to determine at least two points on the tibial mechanical axis. In some embodiments, the second orientation device is configured to calculate the femoral mechanical axis. In some embodiments, the second orientation device is configured to determine at least two points on the femoral mechanical axis. In some embodiments, the first orientation device and the second orientation device are configured to couple with the tibia for calibration. In some embodiments, the system can include a device interface configured to couple to a lateral portion of the femur. In some embodiments, the first orientation device and the second orientation device are configured to determine a varus/valgus angle of the femoral mechanical axis and the tibial mechanical axis. In some embodiments, the first orientation device and the second orientation device are configured to determine a flexion/extension angle of the femoral mechanical axis and the tibial mechanical axis. In some embodiments, the first orientation device and the second orientation device are configured to determine a gap measurement.

In some embodiments, a system for limb alignment is provided. The system can include a first orientation device configured to be coupled with a tibia, the first orientation device comprising at least one inertial sensor. The system can include a second orientation device configured to be coupled with a femur, the second orientation device comprising at least one inertial sensor. In some embodiments, the first orientation device and the second orientation device are configured to calculate a change in position, orientation, or movement between a femoral mechanical axis and a tibial mechanical axis.

In some embodiments, the first orientation device and the second orientation device provide cut verification. In some embodiments, the first orientation device and the second orientation device are configured to calculate an angle relative to the coronal plane when an implant is positioned between the tibia and the femur. In some embodiments, the first orientation device and the second orientation device are configured to calculate an angle relative to the sagittal plane when an implant is positioned between the tibia and the femur. In some embodiments, the first orientation device and the second orientation device are configured to calculate a varus/valgus angle when an implant is positioned between the tibia and the femur. In some embodiments, the first orientation device and the second orientation device are configured to calculate a flexion/extension angle when an implant is positioned between the tibia and the femur. In some embodiments, the first orientation device and the second orientation device are configured to calculate soft tissue balancing when an implant is positioned between the tibia and the femur. In some embodiments, the first orientation device and the second orientation device are configured to calculate a gap measurement when an implant is positioned between the tibia and the femur. In some embodiments, the first orientation device and the second orientation device are configured to verify an angle measurement relative to a pre-operative measurement. In some embodiments, the first orientation device and the second orientation device are configured to verify an angle measurement relative to a pre-operative measurement from an imaging technique. In some embodiments, the first orientation device and the second orientation device are configured to verify the correction of a deformity when an implant is positioned between the tibia and the femur.

In some embodiments, a system for limb alignment is provided. The system can include a first orientation device configured to be coupled with a tibia, the first orientation device comprising at least one inertial sensor. The system can include a second orientation device configured to be coupled with a femur, the second orientation device comprising at least one inertial sensor. In some embodiments, the first orientation device and the second orientation device are configured to calculate a rotation of a tibial mechanical axis about a femoral mechanical axis.

In some embodiments, the first orientation device and the second orientation device are configured to calculate the rotation of the tibial mechanical axis about the femoral mechanical axis in the sagittal plane. In some embodiments, the first orientation device and the second orientation device are configured to calculate the rotation of the tibial mechanical axis about the femoral mechanical axis in the coronal plane. In some embodiments, the first orientation device and the second orientation device are configured to calculate the rotation of the tibial mechanical axis as a varus/valgus angle between the tibial mechanical axis and the the femoral mechanical axis. In some embodiments, the first orientation device and the second orientation device are configured to calculate the rotation of the tibial mechanical axis as a flexion/extension angle between the tibial mechanical axis and the the femoral mechanical axis. In some embodiments, the first orientation device and the second orientation device are configured to calculate the rotation of the tibial mechanical axis about the femoral mechanical axis after resection. In some embodiments, the first orientation device and the second orientation device are configured to calculate the rotation of the tibial mechanical axis about the femoral mechanical axis with an implant positioned between the tibia and the femur. In some embodiments, the first orientation device and the second orientation device are configured to calculate the rotation of the tibial mechanical axis about the femoral mechanical axis to compare with an angle determined pre-operatively. In some embodiments, the first orientation device and the second orientation device are configured to calculate the rotation of the tibial mechanical axis about the femoral mechanical axis to measure a gap. In some embodiments, the first orientation device and the second orientation device are configured to calculate the rotation of the tibial mechanical axis about the femoral mechanical axis to measure soft tissue balancing. In some embodiments, the second orientation device is configured to be coupled with the tibia for calibration.

In some embodiments, a method for determining limb alignment is provided. The method can include coupling a first orientation device with a tibia, the first orientation device comprising at least one inertial sensor. The method can include coupling a second orientation device with a femur, the second orientation device comprising at least one inertial sensor. The method can include calculating a tibial mechanical axis. The method can include calculating a femoral mechanical axis. The method can include moving the tibia to extension to calculate a rotation of the tibial mechanical axis about the femoral mechanical axis.

In some embodiments, the method can include calculating the tibial mechanical axis before calculating a femoral mechanical axis. In some embodiments, the method can include calibrating the first orientation device and the second orientation device before moving the tibia to extension. In some embodiments, the method can include calculating the rotation of the tibial mechanical axis about the femoral mechanical axis when a varus force is applied. In some embodiments, the method can include calculating the rotation of the tibial mechanical axis about the femoral mechanical axis when a valgus force is applied. In some embodiments, the method can include calculating the rotation of the tibial mechanical axis about the femoral mechanical axis during soft tissue release. In some embodiments, the method can include calculating the rotation of the tibial mechanical axis about the femoral mechanical axis with an implant positioned between the tibia and the femur. In some embodiments, the method can include calculating the rotation of the tibial mechanical axis about the femoral mechanical axis about one or more planes.

In some embodiments, a femoral preparation system is provided. The femoral preparation system can include a connector configured to positioned on laterally a femur. The connector can include a coupler. The connector can include at least one opening configured to receive a fixation device. The femoral preparation system can include an orientation device configured to be removably coupled with the connector, the first orientation device comprising at least one inertial sensor.

In some embodiments, the femoral preparation system can include a device interface configured to couple with the coupler and the orientation device. In some embodiments, the femoral preparation system can include a cutting guide bracket configured to couple to a tibial preparation system coupled to a tibia. In some embodiments, the femoral preparation system can include a swivel post configured to position an extension relative to a fixation device positioned at an approximate center of an intercondylar notch. In some embodiments, the femoral preparation system can include a mounting bracket configured to couple to the extension and the coupler of the connector. In some embodiments, the at least one opening comprises a pair of angled and offset openings.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments.

DETAILED DESCRIPTION

Figure 1:
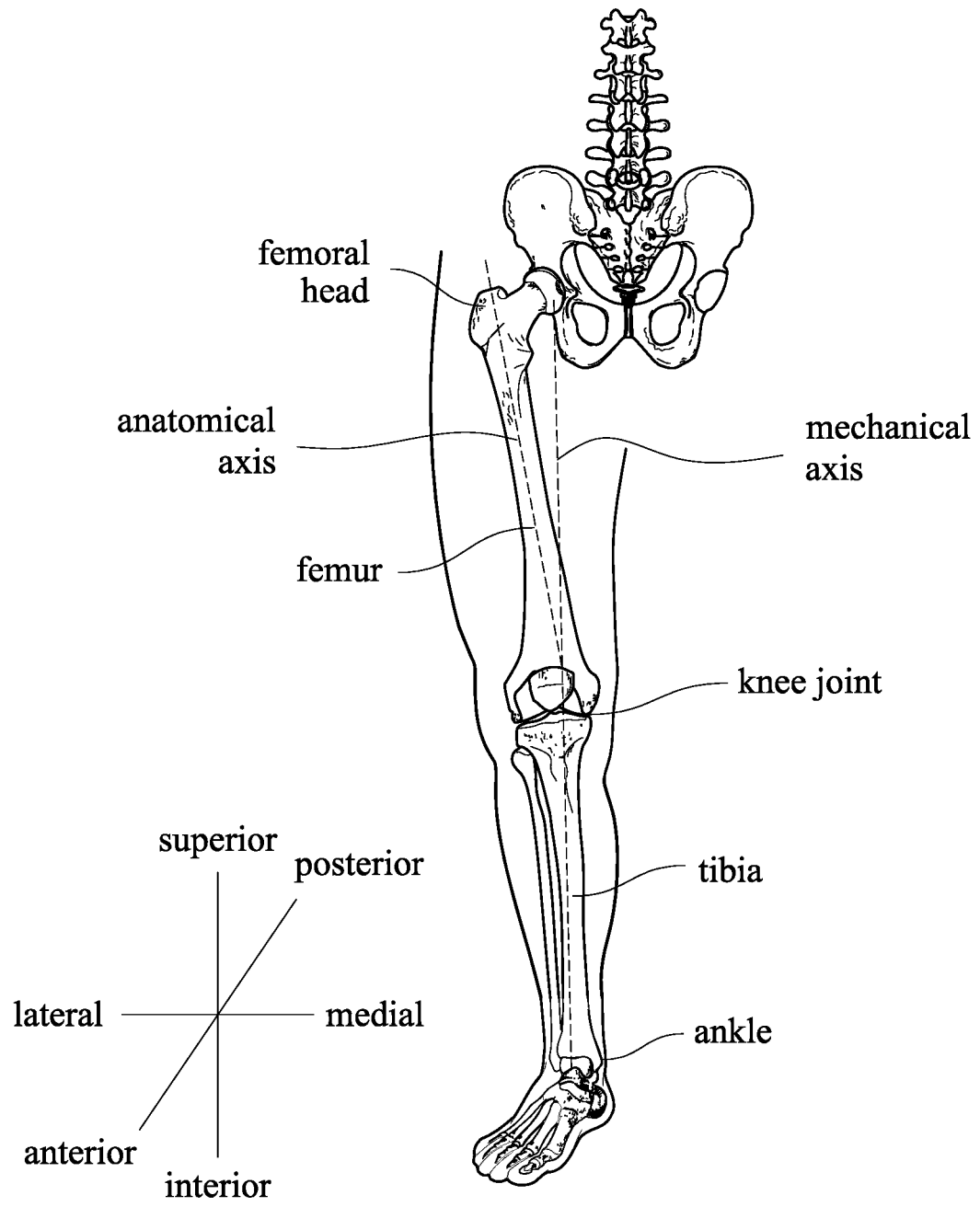
FIG. 1 illustrates an example limb including a tibia and a femur.

FIG. 1 illustrates a femur and a tibia, with the distal portion of the femur and proximal portion of the tibia forming the knee joint. To provide the reader with the proper orientation of the instruments and to assist in more fully understanding the construction of the instruments, an anatomic coordinate system is included on FIG. 1. The anatomic coordinate system indicates the general directions—anterior, posterior, medial, and lateral, as well as superior and inferior. Other relevant terms include proximal, distal, varus and valgus. For a given bone, the terms proximal and distal may refer to the direction that is close or father from the center of the body, respectively. For a given joint, varus may indicate an oblique angle of the joint where the distal portion is closer to the midline of the body (e.g., bow-legged). For a given joint, valgus may indicate an oblique angle of the joint where the distal portion is father from the midline of the body (e.g., knock-kneed). These terms relate to the orientation of the knee bones, such as the femur and tibia and will be used in the descriptions of the various instruments consistent with their known medical usage. Additionally, the terms varus/valgus and posterior/anterior are used herein to describe directional movement. A force may be applied to a bone to move it towards an anatomic direction or orientation. Varus/valgus is a broad term as used herein, and includes, without limitation, rotational movement in a medial and/or lateral direction relative to the knee joint shown in FIG. 1 (e.g. right and left in the page). Varus/valgus includes movement or force to temporarily create a varus/valgus state. Clinically, these forces or movements reveal information about the static and kinematic characteristics of the joint. Posterior/anterior is a broad term as used herein, and includes, without limitation, rotational movement in a posterior and/or anterior direction (e.g. into and out of the page) relative to the knee joint shown in FIG. 1.

Prior to replacing femoral and tibial structures of the knee joint with prosthetic components, surgical cuts commonly called resections are generally made with a saw or other cutting tool or tools along a portion or portions of both the proximal tibia and distal femur. These cuts are made to prepare the tibia and femur for the prosthetic components. After the cuts are made, the prosthetic components can be attached and/or secured to the tibia and femur.

The desired orientation and/or position of these cuts, and of the prosthetic components, can be determined pre-operatively and based, for example, on one or more mechanical axes running through an individual patient's leg. Once the desired locations of these cuts are determined pre-operatively, the surgeon can use the systems and methods described herein to accurately align cutting tools. While the systems and methods are described in the context of a knee joint replacement procedure, the systems and/or their components and methods can similarly be used in other types of medical procedures, including but not limited to shoulder and hip replacement procedures.

Figure 2:
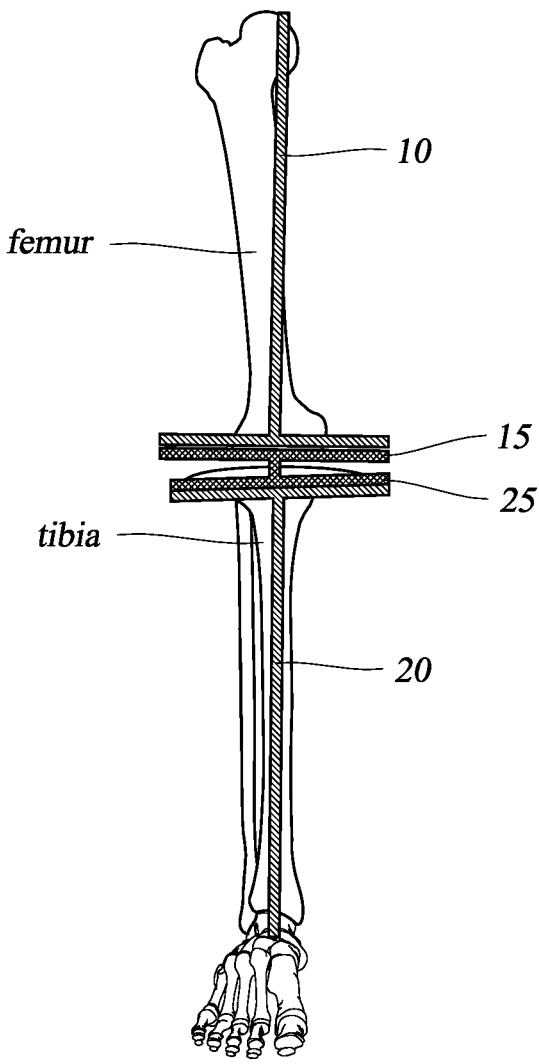
FIG. 2 illustrates mechanical axes of the tibia and the femur.

The systems and methods described herein can also be used for limb alignment and/or joint gap measurements. FIG. 2 illustrates the mechanical axis extending through the femur. The systems and methods described herein can determine an axis 10 extending from a center of rotation of the femur in a socket of a hip to a central portion of a distal portion of the femur. A resection of the femur 15 can be a plane perpendicular to the femoral mechanical axis 10. FIG. 2 illustrates the mechanical axis extending through the tibia. The systems and methods described herein can determine an axis 20 extending from an anatomical proximal point on the tibia to a midpoint between the malleolus on a patient's ankle. A plateau of the tibia 25 can be a plane perpendicular to the tibial mechanical axis 20. The systems and methods described herein can determine the angle between plateaus 15, 25. The plateaus 15, 25 can be estimate of the post-cut planar surface of the tibia and/or femur. The plateaus 15, 25 can be a plane established through some anatomical reference location.

The systems and methods described herein can determine overall limb alignment. For knee surgery, the systems and methods can determine overall alignment between the femur and the tibia, e.g., between the axes 10, 20 which can be determined by systems and methods disclosed herein. The systems and methods described herein can be used in total knee arthroplasty. The systems and methods described herein can be used in unicompartmental knee arthroplasty. The systems and methods described herein can fill an unmet clinical need for limb alignment for the knee and other joints.

In some embodiments, the systems and methods provide dynamic limb alignment angles. In some embodiments, the systems and methods provide dynamic limb alignment angles through a range of motion. In some embodiments, the systems and methods provide dynamic limb alignment angles during flexion/extension. In some embodiments, the systems and methods provide dynamic limb alignment angles when the user applies varus/valgus force. In some embodiments, the systems and methods provide dynamic limb alignment angles before and after tibial resection. In some embodiments, the systems and methods provide dynamic limb alignment angles before and after femoral resection. In some embodiments, the systems and methods provide dynamic limb alignment angles before and after any resection. In some embodiments, the systems and methods provide static limb alignment angles.

In some methods, the method can include one or more steps of a surgical workflow. The method can include an incision to gain access to the joint. The method can include an initial assessment. The method can estimate, prescribe, perform or otherwise include a proximal tibial resection. The method can include a spacer block assessment for gap balancing. In some methods, spacer block assessment can only occur after resections have been made on both tibia and femur. The method can estimate, prescribe, perform or otherwise include a distal femoral resection. The method can include positioning of a trial implant or an implant. The method can include cementing the implant. The method can include closing up the incision. One or more of these methods steps can be facilitated by the use of the systems and methods described herein.

In some methods, the method can include one or more steps involving limb alignment measurements. The method can include registering the femoral mechanical axis. The method can include registering the tibial mechanical axis. The method can include limb alignment measurements during the initial assessment. The method can include limb alignment measurements during the femoral cut. The method can include limb alignment measurements during the spacer block assessment. The method can include limb alignment measurements during the positioning of the trial implant or implant. The method can include limb alignment measurements that are saved in a patient record before, during, or after closing up the incision and/or completing the procedure, the patient record being accessible for later review and use.

The systems and methods can provide many advantages. The systems and methods can provide reproducible tibial plateau varus/valgus assessment, prescription, or other form of navigation for cut verification. The systems and methods can provide reproducible tibial plateau posterior slope assessment, prescription, or other form of navigation. The systems and methods can provide a minimally disruptive fixation method of the instrumentation or jigs described herein. The systems and methods can be easily integrated into current surgical workflows The systems and methods can provide reproducible measurements of depth resection of the tibial plateau from the lowest part of the articulating surface. The systems and methods can provide tibial plateau cut navigation.

The systems and methods can provide many advantages. The systems and methods can provide measurement of overall limb alignment of the tibial and femoral mechanical axis. The systems and methods can include instrumentation to make a minimal resection recut. The systems and methods can minimize soft tissue disruption with or by instrumentation.

The systems and methods can provide many advantages. The systems and methods can facilitate control of tibial rotation. The systems and methods can provide an easy and reproducible measurement of the impact of tibial component rotation on limb alignment. In some methods, tibial rotation includes dynamic behavior of the tibia. In some methods, tibial rotation includes static unloaded rotation in extension. In some methods, the impact of tibial component rotation in flexion and extension is measured and displayed. In some methods, dynamic rotation is measured and displayed. The systems and methods can provide an easy and reproducible measurement of the impact of tibial component rotation on limb alignment the space between the femoral condyles and the tibial plateau during varus/valgus stresses. The systems and methods can facilitate gap balancing. The systems and methods can facilitate assessment, measurement and adjustment of ligament tension. The systems and methods can provide a meaningful physiological assessments, e.g., measurements to determine overall limb alignment.

Figure 3:
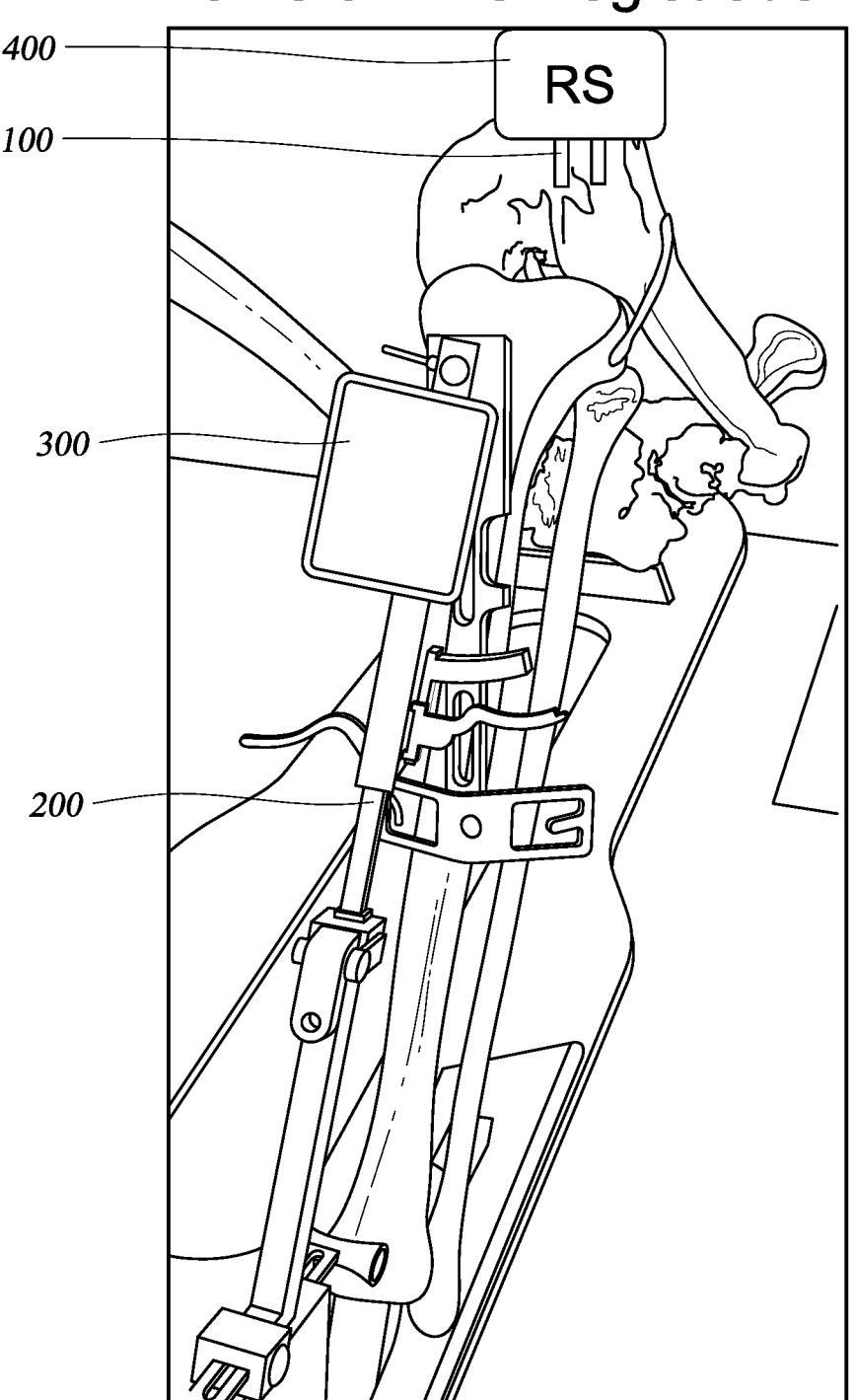
FIG. 3 illustrates a portion of a system for femoral mechanical axis registration.
Figure 4:
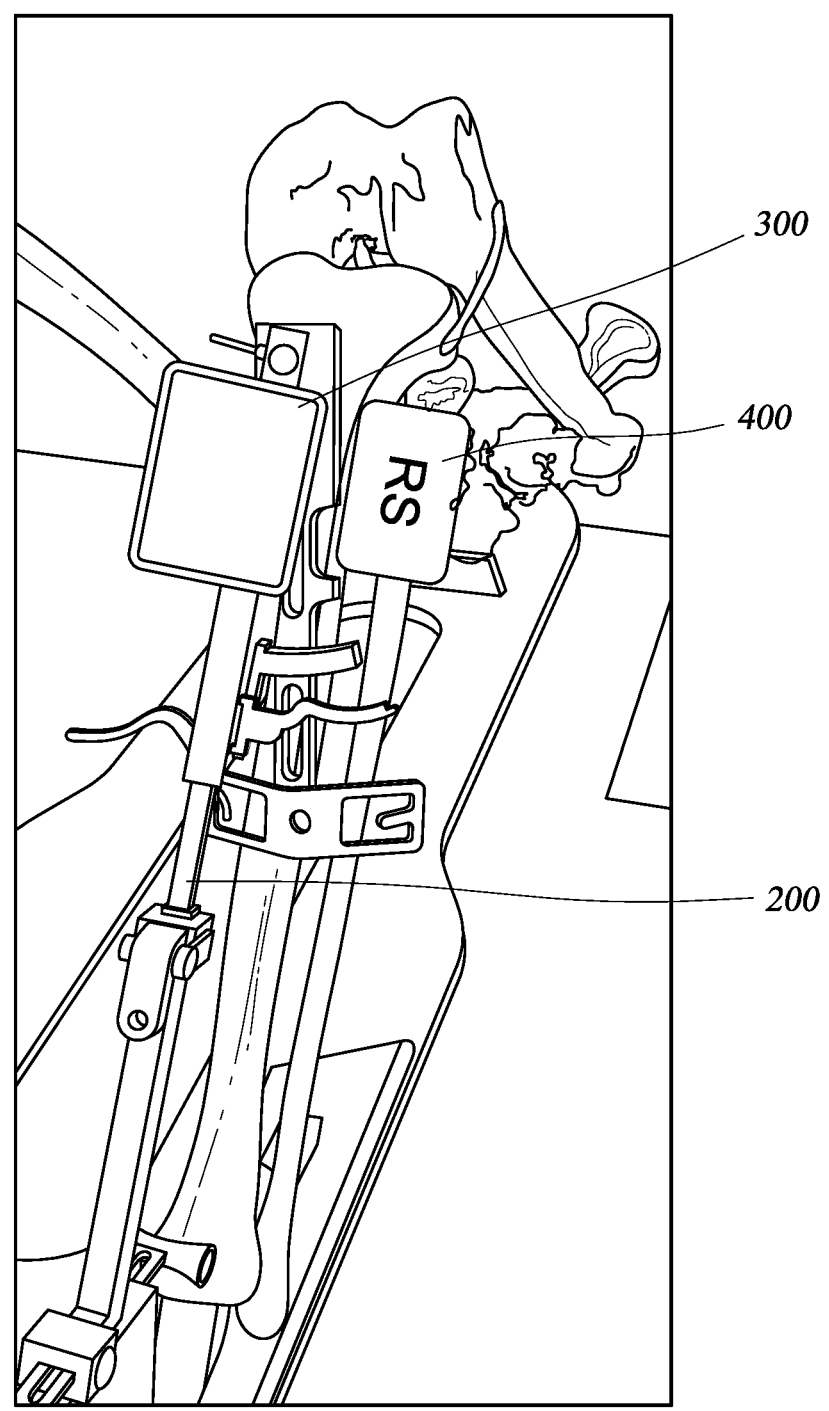
FIG. 4 illustrates a portion of a system for tibial mechanical axis registration.
Figure 5:
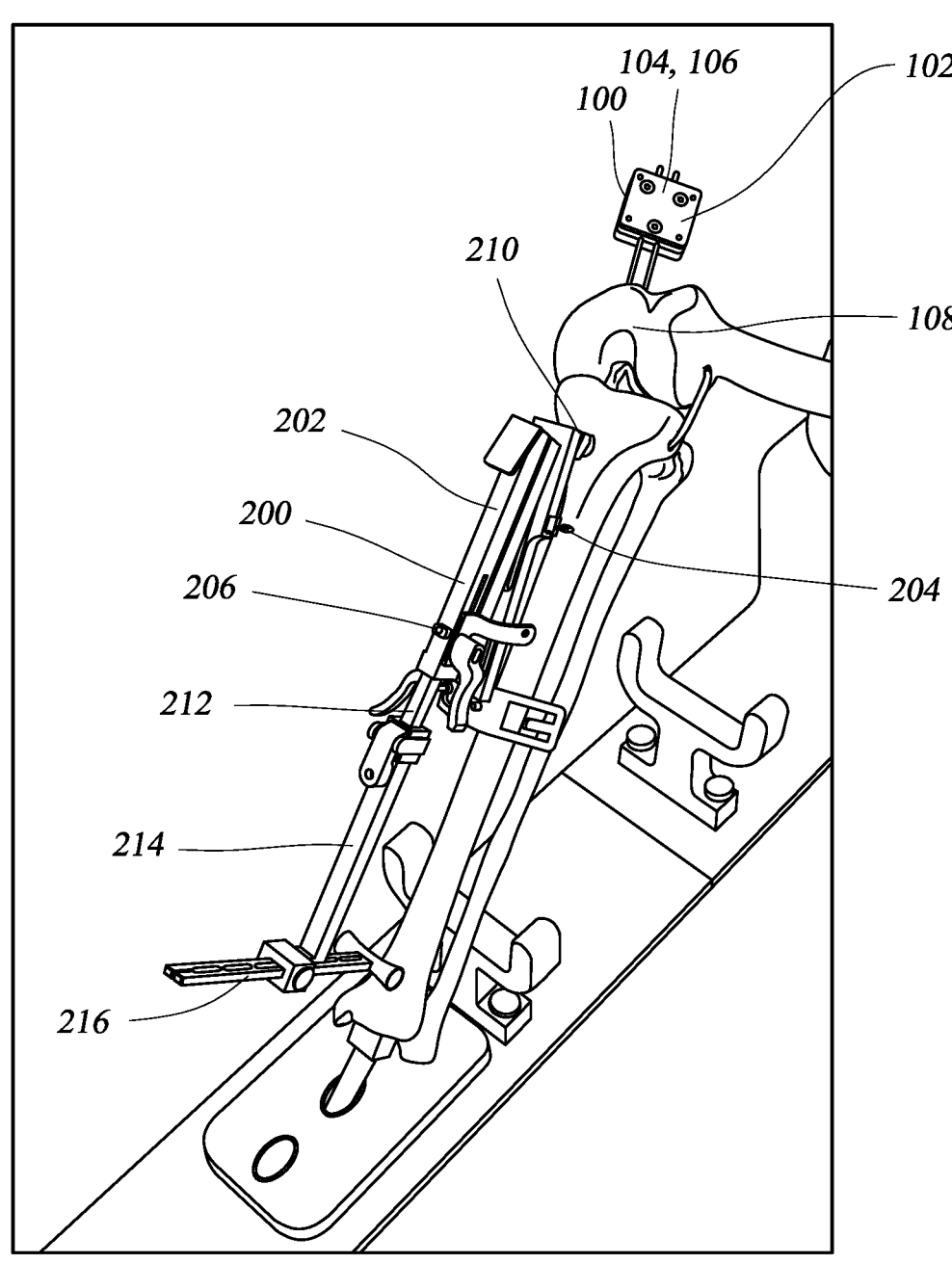
FIG. 5 illustrates a femoral preparation system coupled with a distal femur and a tibia preparation system coupled with a proximal tibia.
Figure 6:
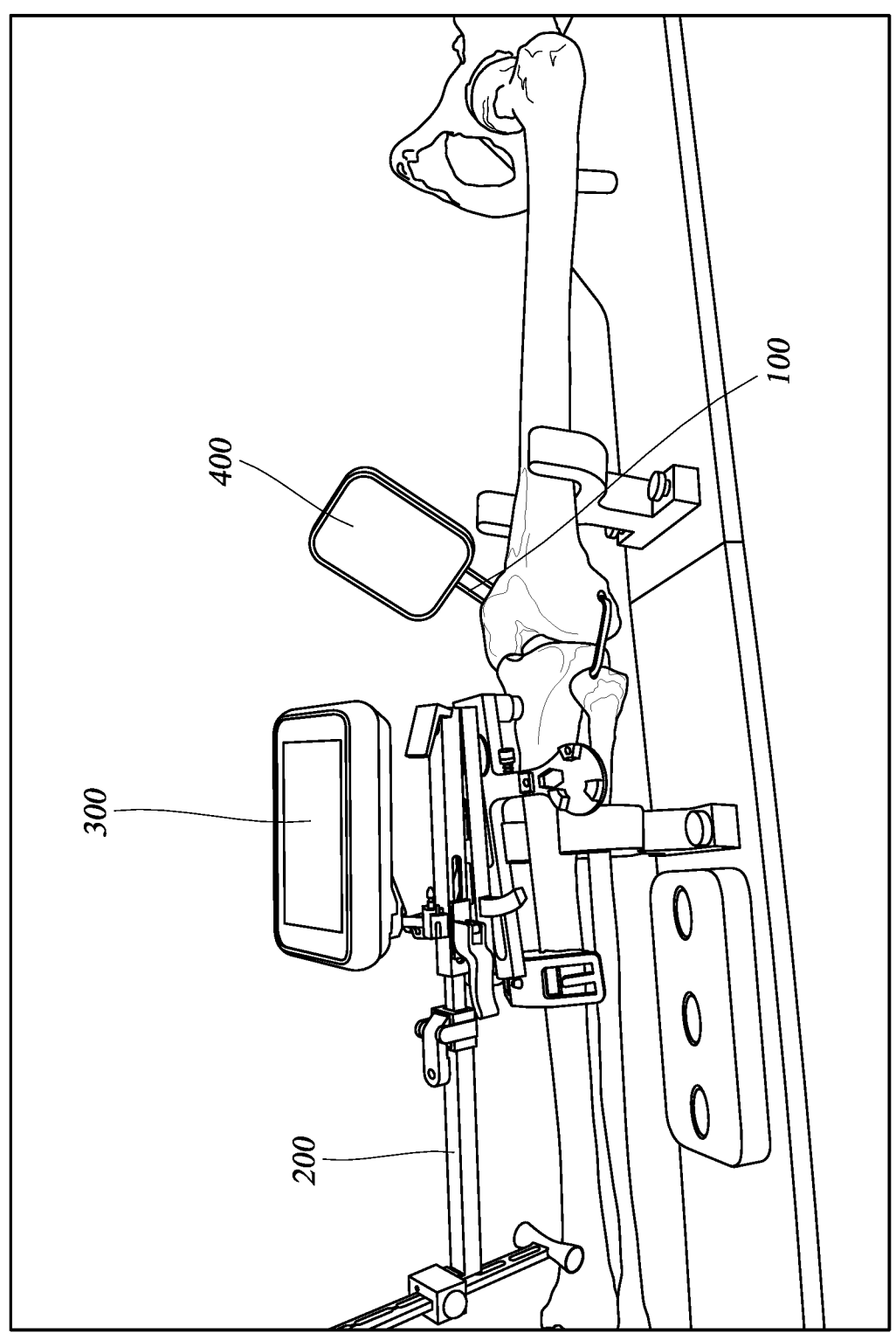
FIGS. 6-7 illustrates an assembled view for femoral mechanical axis registration.
Figure 7:
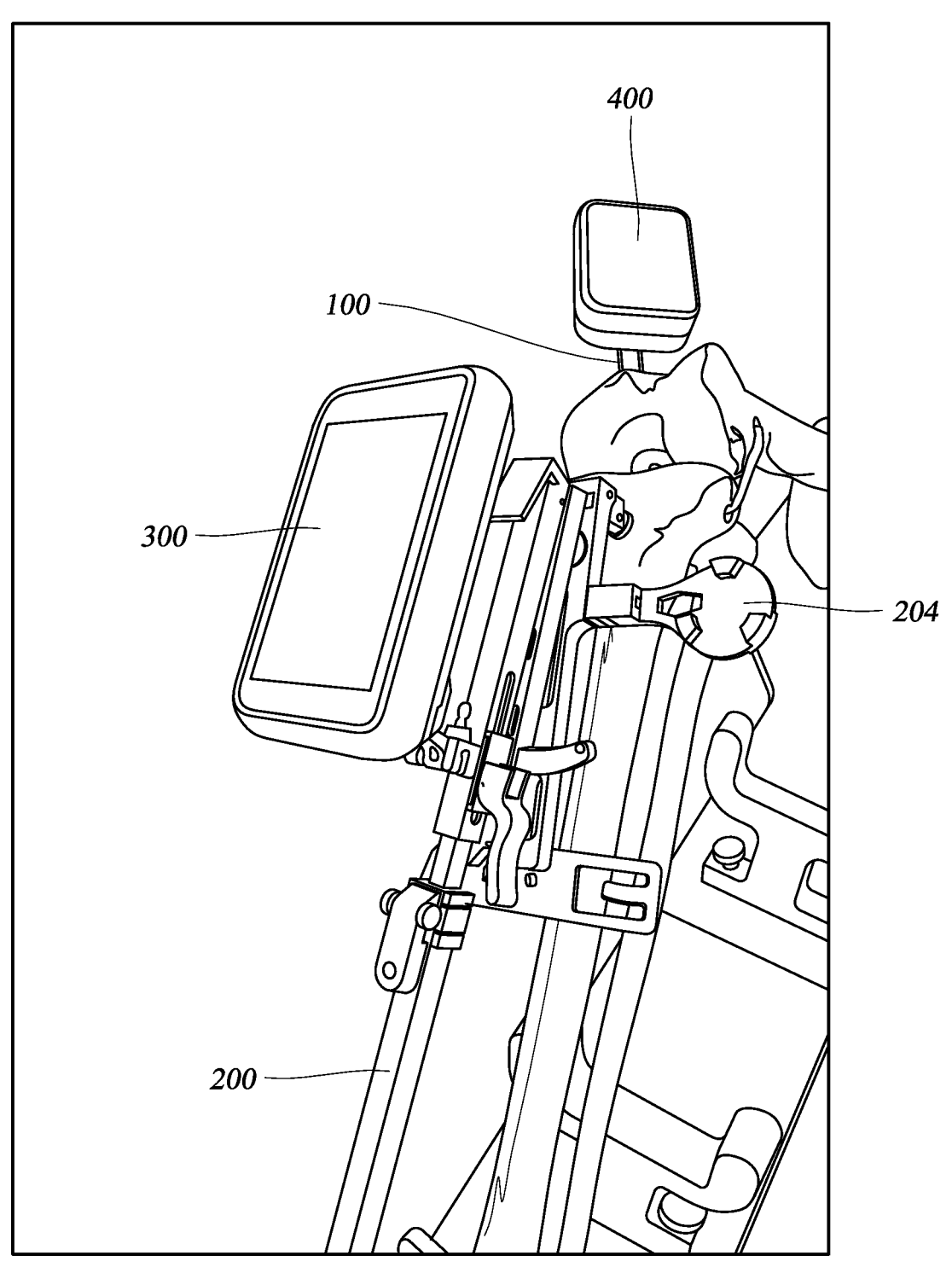
Figure 8:
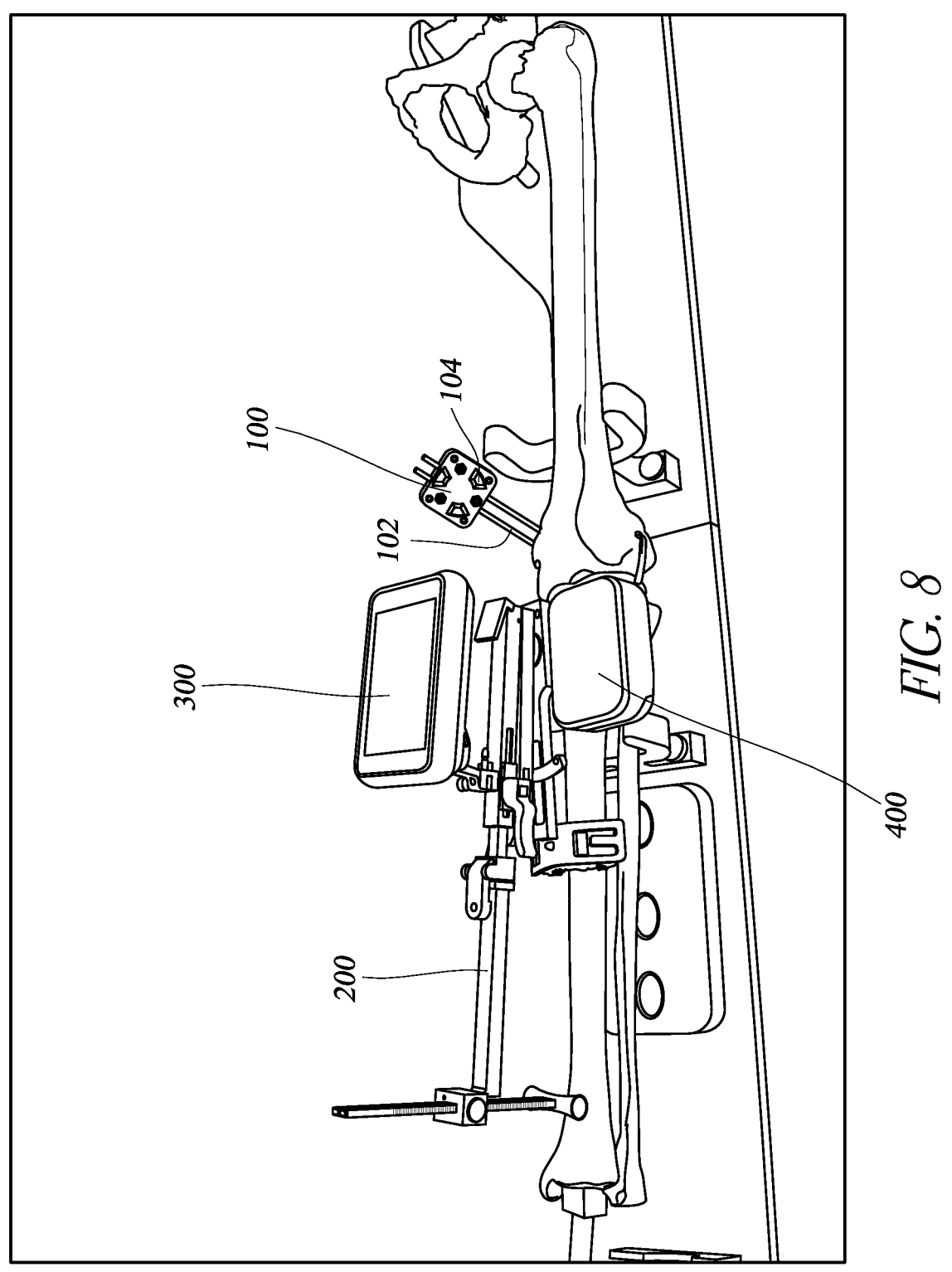
FIGS. 8-9 illustrates an assembled view for calibration.
Figure 9:
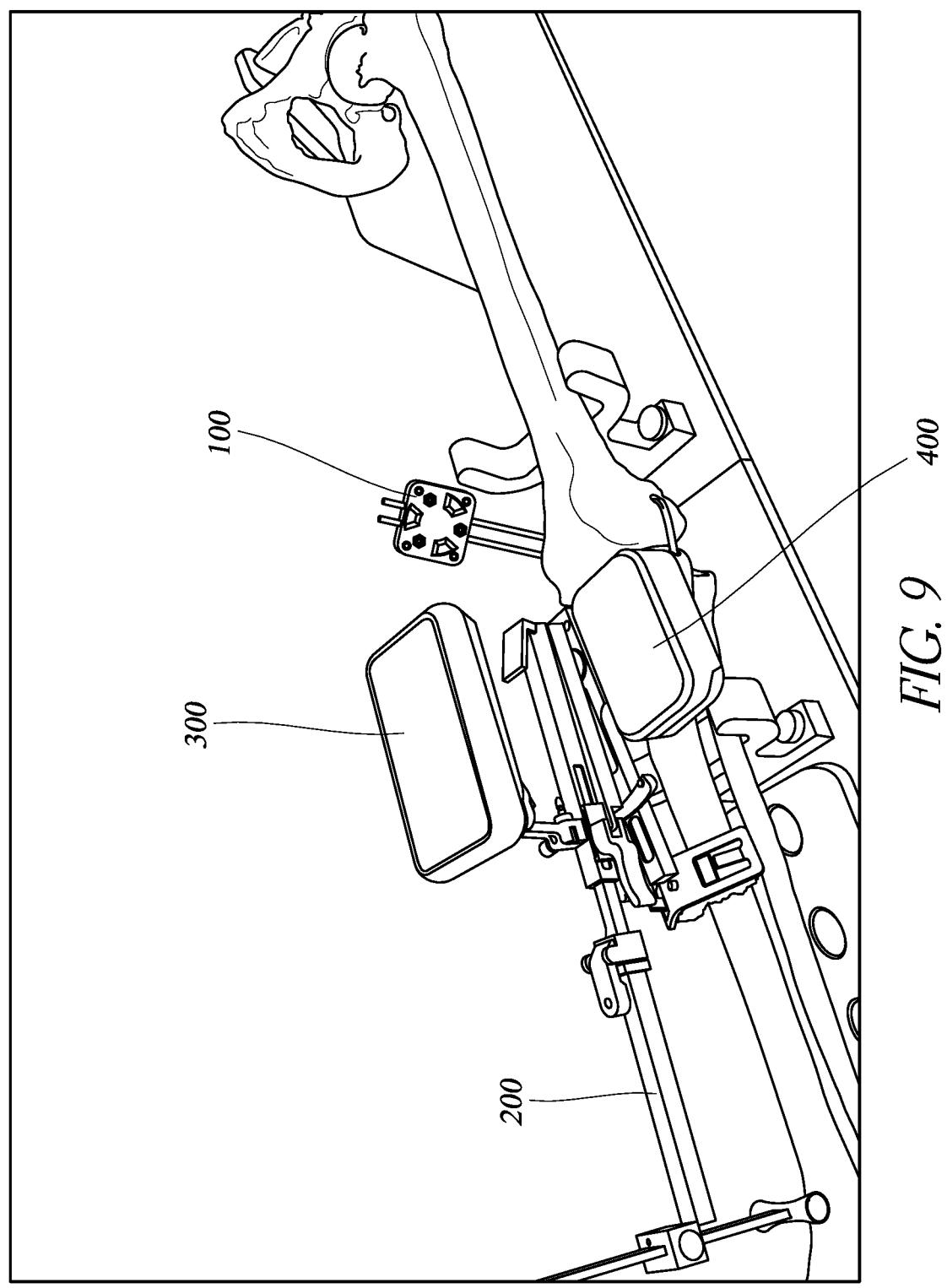

In some embodiments, the systems and methods can include femoral mechanical axis registration. FIG. 3 illustrates the system positioned for femoral mechanical axis registration. In some embodiments, the systems and methods can include tibial mechanical axis registration. FIG. 4 illustrates the system for tibial mechanical axis registration. FIG. 5 illustrates a femoral preparation system 100 and a tibial preparation system 200. The femoral preparation system 100 comprises a jig configured to be coupled to the femur. The tibial preparation system 200 comprises a jig configured to be coupled to the tibia. FIG. 6 illustrates the system positioned for femoral mechanical axis registration with the leg in extension. FIG. 7 illustrates the system positioned for femoral mechanical axis registration with the leg in flexion. FIGS. 8 and 9 illustrate the system positioned for calibration.

The systems and methods can include the femoral preparation system 100. In some methods, the femoral preparation system 100 can be utilized up to and including resection. In some methods, the femoral preparation system 100 is utilized for assessments and measurements before and/or after resection. In some methods, the femoral preparation system 100 can be utilized up to, but not including resection. In some methods, the femoral preparation system 100 is utilized for assessments and measurements, without resection. The systems and methods can include the tibial preparation system 200. In some methods, the tibial preparation system 200 can be utilized up to and including resection. In some methods, the tibial preparation system 200 is utilized for assessments and measurements before and/or after resection. In some methods, the tibial preparation system 200 can be utilized up to, but not including resection. In some methods, the tibial preparation system 200 is utilized for assessments and measurements, without resection. The systems and methods can include a surgical orientation device 300. The systems and methods can include a reference sensor 400.

During femoral axis registration shown in FIG. 3, the femoral preparation system 100 can be coupled to the femur. The reference sensor 400 can be coupled to the femoral preparation system 100. The tibial preparation system 200 can be coupled to the tibia. The surgical orientation device 300 can be coupled to the tibial preparation system 200. The femoral preparation system 100 can determine and/or can be mounted to a distal point of the femur corresponding to a location of a distal portion of a femur mechanical axis. In some methods, a pin is inserted in the center of the knee joint on femur. In some methods, the knee is placed in flexion. In some embodiments, the femoral preparation system 100 can be located at the intersection of Whiteside's line and the epicondylar axis. In some methods, the anatomy of the femur is probed to determine a location corresponding to the distal point of the femur mechanical axis. The femoral preparation system 200 can determine a proximal point disposed on the femur mechanical axis. In some methods, an outrigger jig (not shown) is coupled to the pin placed at the center of the knee. The outrigger jig is utilized to guide placement of pins 102, 104 on side of the knee. The pins 102, 104 are coupled to a jig portion to mount the reference sensor 400 for femur axis registration. The reference sensor 400 is mounted outside of joint to allow limb to be placed in extension. In some methods, the femur is moved through a range of motion to determine the proximal point of the femur mechanical axis. In some methods, the surgical orientation device 300 and the reference sensor 400 can determine a mechanical axis of the femur. In some methods, the reference sensor 400 is used to track movement of the femur as well as a cutting block. In some methods, the surgical orientation device 300 will not be attached to the femur during or after axis registrations. In some methods, the surgical orientation device 300 may still be attached to aid in placement of the cutting block. The mechanical axis of the femur can be a line intersecting the distal point and the proximal point. In some embodiments, the mechanical axis of the femur can be a line intersecting the distal point to which the femoral preparation system 100 is mounted. In some embodiments, the mechanical axis of the femur can be a line intersecting the proximal point established the reference sensor 400 during movement of the femur.

During tibial axis registration shown in FIG. 4, the tibial preparation system 200 can be coupled to the tibia. The surgical orientation device 300 can be coupled to the tibial preparation system 200. The reference sensor 400 can be coupled to the tibial preparation system 200. In some embodiments, the femoral preparation system 100 is removed, or at least a portion of the femoral preparation system 100 is removed. The tibial preparation system 200 can determine the proximal point of tibial mechanical axis. In some methods, the anatomy of the tibia is probed to determine the proximal point of the tibial mechanical axis. The tibial preparation system 200 can determine a distal point of the tibial mechanical axis. In some methods, the anatomy of the tibia is probed as an input to the determination of the distal point of the tibial mechanical axis. In some methods, two portions of anatomy of the tibia are probed to enable the surgical orientation device 300 to determine a distal point corresponding to the tibial mechanical axis. The surgical orientation device 300 and the reference sensor 400 can determine a mechanical axis of the tibia. The mechanical axis of the tibia can include the distal and proximal point of the tibia.

FIG. 5 illustrates additional features of the femoral preparation system 100 and the tibial preparation system 200. The femoral preparation system 100 can be used to calculate the femoral mechanical axis extending through the femur. In some embodiments, the femoral preparation system 100 can be used to modify a natural femur with a distal femoral resection, enabling a prosthetic component to be securely mounted upon the distal end of the femur. The femoral preparation system 100 can support a cutting block or guide to facilitate one or more resections. As described herein, the femoral preparation system 100 can be designed for total knee arthroplasty or unicompartmental knee arthroplasty. In some embodiments, the femoral preparation system 100 is used to assess femur characteristics, such as the orientation of the mechanical axis of the femur in relation to the tibia or a contralateral femur in a controlled manner to assess whether the joint should be modified in a manner adjusting orientation of the femur or another bone. Thus, the femoral preparation system 100 can be used for characterization without resection or other steps in preparation for a femoral joint component.

The femoral preparation system 100 can comprise a femoral jig assembly 102. The femoral jig assembly 102 can include a reference sensor device interface 104 by which the reference sensor 400 can be coupled to the femoral jig assembly 102. In some embodiments, the femoral jig assembly 102 can include a surgical orientation device interface 106 by which the surgical orientation device 300 can be coupled to the femoral jig assembly 102.

The surgical orientation device interface 106 can advantageously enable the surgical orientation device 300 to be quickly coupled and decoupled with the femoral jig assembly 102 during a surgical procedure. This enables the surgical orientation device 300 to be used in a modular fashion, with a variety of orthopedic fixtures at one or more stages of a procedure.

The reference sensor device interface 104 can advantageously enable the reference sensor 400 to be quickly coupled and decoupled with the femoral jig assembly 102 during a surgical procedure. This enables the reference sensor 400 to be used in a modular fashion, with a variety of orthopedic fixtures at one or more stages of a procedure.

In some techniques for locating a distal point of the mechanical axis of the femur, a distal end portion of the femur is exposed using any conventional surgical technique. The tibia and the femur can then be placed in approximately 90 degrees of flexion as shown in FIG. 3. It is possible to place the leg in other degrees of flexion.

A small hole for receiving a portion of a fixation pin 108 of the femoral jig assembly 102 can then be drilled using any conventional surgical technique at an appropriate anatomical location. In some methods, the femoral jig assembly 102 can be coupled to the distal end portion of the femur. In some methods, the anatomical location can be along the Whiteside's line. In some methods, the anatomical location can be along the epicondylar axis. In some methods, the anatomical location can be the intersection of Whiteside's line and the epicondylar axis. The method can include coupling one or more components of the femoral jig assembly 102 to the femur using one or more fixation pins 108.

In some methods, the femoral jig assembly 102 can be offset from to the distal end portion of the femur. In some methods, the anatomical location can be offset from Whiteside's line. In some methods, the anatomical location can be offset from the epicondylar axis. In some methods, the anatomical location can be offset from the intersection of Whiteside's line and the epicondylar axis. In some methods, this offset is an input to determine a point along the femoral mechanical axis. In some methods, the anatomical location can be any suitable anatomical landmark or combination of landmarks within or adjacent or offset from to the distal end portion of the femur. Once the femoral jig assembly 102 is attached to the femur, the method can include noting the indicia of distance provided by reference markings and the location of the fixation pin 108 in relation to the reference markings in order to establish the offset. In the method thus far, a distal point corresponding to the mechanical axis of the femur can be approximated by using a portion of the femoral jig assembly 102 to locate the center of the femur.

Once the surgical orientation device 300 and/or the reference sensor 400 are coupled to the femoral jig assembly 102, the method can further include placing the leg in extension. The surgical orientation device 300 and/or the reference sensor 400 can be used to determine the relative coordinates of a center pivot point on the femur. By determining the coordinates of the pivot point of the femoral head, the surgical orientation device 300 and/or the reference sensor 400 can calculate the location and/or orientation of the mechanical axis that extends through the femur.

In order to determine the coordinates of the pivot point of the femoral head and thus the pivot point of the mechanical axis, the leg can be moved (e.g. swung). FIGS. 6 and 7 show the femur in various positions for femoral mechanical axis registration. The femur can be moved in any method to determine the proximal point. In some methods, the reference sensor 400 can determine a mechanical axis of the femur. For example, the leg can be moved in several different directions and/or planes, with the surgical orientation device 300 and/or the reference sensor 400 coupled to the femoral jig assembly 102. Readings such as angular rate and acceleration ("surgical orientation device 300 and/or the reference sensor 400 data") of the femur can be obtained by the surgical orientation device 300 and/or the reference sensor 400 until the location and/or orientation of the mechanical axis of the leg and the femur ("femoral mechanical axis") is found. In one embodiment, where one or more multi-axis (e.g., three-axis) accelerometers and gyroscopes are used, the surgical orientation device 300 and/or the reference sensor 400 data for each movement of the femur can be numerically integrated over time to obtain a trajectory of position and velocity points.

The acceleration and angular rate sensed by the surgical orientation device 300 and/or the reference sensor 400 during the leg movement can be processed while the leg is moved about its pivot point. The surgical orientation device 300 and/or the reference sensor 400 can provide an output vector representing the center of the rotation with respect to the inertial sensor axes of the surgical orientation device 300 and/or the reference sensor 400. The leg can be moved about its pivot point while inertial data is being processed by the microprocessor. An algorithm implemented on the microprocessor can process the inertial data in real time and determine if the leg is static or dynamically moving. Data from one or both states can be used by the algorithm to determine the pivot point.

The method of calculating the location and/or orientation of the femoral mechanical axis described herein, and for calculating in general the location and/or orientation of any axis based on a pivot point, can provide accurate determination of pivot point location and radius of curvature without the burdensome and sometimes near impossible restraints of external measurements encountered in medical procedures. For example, the method can permit calculation of pivot points in blind situations where the end joint is typically hidden or unobservable, such as for the case of the head of a femur.

FIG. 5 also illustrates the tibial preparation system 200. The tibial preparation system 200 can be used to calculate the tibial mechanical axis extending through the tibia. In some embodiments, the tibial preparation system 200 can be used to modify a natural tibia with a proximal tibial resection, enabling a prosthetic component to be securely mounted upon the proximal end of the tibia. The tibial preparation system 200 can support a cutting block or guide to facilitate one or more resections. As described herein, the tibial preparation system 200 can be designed for total knee arthroplasty or unicompartmental knee arthroplasty.

The tibial preparation system 200 can comprise a tibial jig assembly 202. The tibial jig assembly 202 can include a reference sensor device interface 204 by which the reference sensor 400 can be coupled to the tibial jig assembly 202. The tibial jig assembly 202 can include a surgical orientation device interface 206 by which the surgical orientation device 300 can be coupled to the tibial jig assembly 202.

The surgical orientation device interface 206 can advantageously enable the surgical orientation device 300 to be quickly coupled and decoupled with the tibial jig assembly 202 during a surgical procedure. This enables the surgical orientation device 300 to be used in a modular fashion, such as moving between the femoral jig assembly 102 and the tibial jig assembly 202.

The reference sensor device interface 204 can advantageously enable the reference sensor 400 to be quickly coupled and decoupled with the tibial jig assembly 202 during a surgical procedure. This enables the reference sensor 400 to be used in a modular fashion, such as moving between the femoral jig assembly 102 and the tibial jig assembly 202.

The reference sensor 400 can preferably be coupled with the tibial jig assembly 202 such that during a knee replacement procedure, the reference sensor 400 follows the movement of the tibia, and generally does not move independently with respect to the tibia. The configuration of the reference sensor device interface 204 can enable low profile mounting of the reference sensor 400 beneath other components of the tibial jig assembly 202, such that the reference sensor 400 can be located between at least one moving component of the tibial jig assembly 202 and the tibia of the patient.

In some techniques for locating a proximal point of the mechanical axis of the tibia, a proximal end portion of the tibia is exposed using any conventional surgical technique. The tibia and the femur can then be placed in approximately 90 degrees of flexion as shown in FIG. 5. It is possible to place the leg in other degrees of flexion. A small hole for receiving a portion of a fixation pin of the tibial jig assembly 202 can then be drilled using any conventional surgical technique at an appropriate anatomical location.

The tibial jig assembly 202 can include a midline reference probe assembly 210. The midline reference probe assembly (not shown) can be positioned at an appropriate anatomical location at the proximal tibia. In some methods, the anatomical location can be a point just posterior to the insertion of the anterior cruciate ligament ("ACL"). In some methods, the anatomical location can be a location near the insertion of the anterior cruciate ligament. In some methods, the anatomical location can be a soft point on the top of the tibia commonly referred to as the A/P point of the mechanical axis. This point is generally located along a tibial spine on top of the tibia, and marks the location of a point along the mechanical axis of the tibia. In some methods, the anatomical location can be any suitable anatomical landmark. In some methods, the midline reference probe assembly 210 can be resting over the anatomical location.

In some methods, the tibial jig assembly 202 can be offset from to the proximal end portion of the tibia. Once the tibial jig assembly 202 is coupled to the tibia and the midline reference probe assembly is positioned, the method can include noting the indicia of distance provided by reference markings and the location of the midline reference probe assembly in relation to the reference markings in order to establish the offset. The offset can be entered into the surgical orientation device 300. The offset can facilitate the determination of the proximal point of the tibia. In the method thus far, a proximal point corresponding to the mechanical axis of the tibia can be approximated by using a portion of the tibial jig assembly 202 to locate the center of the tibia.

In some methods, the tibial jig assembly 202 can include a probe assembly 212 comprising an elongate member 214 and a probe member 216. The probe member 216 can be configured to contact an anatomical landmark, such as for example a malleolus on a patient's ankle. The surgical orientation device 300 can be coupled to the probe assembly 212 such that movement of the probe assembly 212 causes corresponding movement of the surgical orientation device 300. The surgical orientation device 300 can thereby track the orientation of the probe assembly 212 as the probe assembly 212 contacts distal points.

The method can further comprise acquiring landmarks to determine the location of the mechanical axis passing through the tibia. For example, landmarks can be acquired by engaging the probe member 216 of probe assembly 212 with a medial malleolus in a first reference position. For example, landmarks can be acquired by engaging the probe member 216 of probe assembly 212 with the lateral malleolus in the second reference position. Acquisition of the malleolus can be accomplished by swinging the probe assembly 212 and/or a portion or portions of the tibial jig assembly 202 such that the probe member 216 contacts the sides of the ankle. Thereafter, the surgical orientation device 300 can determine the location of the tibial mechanical axis. In some embodiments, the surgical orientation device 300 can locate the sagittal and coronal planes extending through the tibial mechanical axis. In some embodiments, the surgical orientation device 300 can calculate the location of the mechanical axis by assuming that the tibial mechanical axis extends from the point of contact of the midline probe assembly 210 with the proximal tibia through a point that is halfway between the two malleolus points contacted by the probe member 216.

During each landmark acquisition, the user can palpate the ankle. Once the location of the malleolus is contacted by the probe member 216, the user can press an user input on the surgical orientation device 300 to cause the surgical orientation device 300 to determine the orientation of the surgical orientation device 300 in the reference position. For example, the surgical orientation device 300 can register and/or calculate the current orientation of the surgical orientation device 300 based on data collected from the sensor(s) inside the surgical orientation device 300 at the first and second reference positions. The orientation of the surgical orientation device 300 in the first and second reference positions can be used to identify the orientation of a coronal plane extending through the tibia that contains the mechanical axis of the tibia. The orientation of the surgical orientation device 300 in the first and second reference positions can be used to identifying the location and/or orientation of a sagittal plane containing the mechanical axis of the tibia.

In some methods, the mechanical axis of the tibia is determined. The tibia and femur can be in flexion as shown in FIG. 4. The surgical orientation device 300 can be positioned on the tibial preparation system 200. The reference sensor 400 can be positioned on the tibial preparation system 200. During landmark registration, the surgical orientation device 300 determines the mechanical axis of the tibia in flexion. The reference sensor 400 can track the position of the tibia. The surgical orientation device 300 stores the tibia mechanical axis. In some embodiments, the surgical orientation device 300 determines the mechanical axis that extends from the point of contact of the midline probe assembly 210 and a point that is halfway between the two malleolus points contacted by the probe member 216.

In some methods, the mechanical axis of the femur is determined. The tibia and femur can be in flexion as shown in FIG. 3. The surgical orientation device 300 can be positioned on the tibial preparation system 200. The reference sensor 400 can be positioned on the femoral preparation system 100. During landmark registration, the reference sensor 400 can determine the mechanical axis of the femur in flexion. The surgical orientation device 300 stores the femoral mechanical axis. In some embodiments, the surgical orientation device 300 determines the mechanical axis that extends from the point of contact of the approximate center of the intercondylar notch and a rotational center. In some methods, the mechanical axis of the tibia is determined before the mechanical axis of the femur. In other methods, the mechanical axis of the femur is determined before the mechanical axis of the tibia.

In some methods, the leg is transitioned to extension for limb alignment measurements. The leg is shown in extension in FIG. 6. The surgical orientation device 300 can be positioned on the tibial preparation system 200. The reference sensor 400 can be positioned on the femoral preparation system 100. In some methods, one of the surgical orientation device 300 and the reference sensor 400 is positioned on the femoral preparation system 100 and the other of the surgical orientation device 300 and the reference sensor 400 is positioned on the tibial preparation system 200.

The surgical orientation device 300 and the reference sensor 400 determined the mechanical axis of the tibia and femur before the leg is transitioned to extension. The surgical orientation device 300 stored the mechanical axes. The mechanical axis of the tibia and femur can be stored as vectors. In some embodiments, the surgical orientation device 300 and the reference sensor 400 are configured to sense changes in orientation of the mechanical axis of the tibia relative to a fixed reference frame when the leg is in extension. In some embodiments, the surgical orientation device 300 and the reference sensor 400 are configured to sense changes in orientation of the mechanical axis of the femur relative to a fixed reference frame when the leg is in extension. In some embodiments, the surgical orientation device 300 and the reference sensor 400 are configured to sense changes in orientation of the mechanical axes. In some embodiments, the surgical orientation device 300 and the reference sensor 400 sense changes in orientation of the mechanical axes of the tibia and femur when the leg is in extension. In some embodiments, the surgical orientation device 300 and the reference sensor 400 sense changes in orientation of the mechanical axes of the tibia and femur when the leg is in extension relative to the orientation of the mechanical axes of the tibia and femur when the leg is in flexion. The leg is shown in flexion in FIG. 7.

The changes in orientation of the mechanical axes of the tibia and femur can determine a varus/valgus angle between the mechanical axes of the tibia and femur. The changes in orientation of the mechanical axes of the tibia and femur can determine a flexion/contracture angle between the mechanical axes of the tibia and femur. The changes in orientation of the mechanical axes of the tibia and femur can be measured in the coronal plane. The changes in orientation of the mechanical axes of the tibia and femur can be measure in the sagittal plane.

The relative positioning of the surgical orientation device 300 and the reference sensor 400 can determine the angulation between the mechanical axis. Varus/valgus includes rotational movement in a medial and/or lateral direction. The surgical orientation device 300 and the reference sensor 400 can be used for limb alignment measurements. The surgical orientation device 300 and the reference sensor 400 can determine the mechanical axis extending from a center of rotation of the femur in a socket of a hip to a landmark on the distal portion of the femur. A plateau of the femur can be a plane perpendicular to the femoral mechanical axis. The surgical orientation device 300 and the reference sensor 400 can determine the mechanical axis extending from a landmark on the proximal portion of the tibia to a midpoint between the malleolus on a patient's ankle. A plateau of the tibia can be a plane perpendicular to the tibial mechanical axis. The surgical orientation device 300 and the reference sensor 400 can determine the angle between plateaus. The surgical orientation device 300 and the reference sensor 400 can determine a varus/valgus angle between plateaus. The surgical orientation device 300 and the reference sensor 400 can determine a flexion/contracture angle between plateaus. The surgical orientation device 300 and the reference sensor 400 can determine an angle relative to one or more planes. The surgical orientation device 300 and the reference sensor 400 can determine an angle relative to one or more anatomical planes. The surgical orientation device 300 and the reference sensor 400 can determine an angle based on a position in a three dimension coordinate system.

In some methods, the mechanical axes are determined prior to resection. In some methods, the alignment of the tibial and femoral mechanical axes is determined prior to resection. In some methods, the leg is transitioned to extension for limb alignment measurements before resection. The change in orientation of the tibial and femoral mechanical axes between flexion and extension can be stored. The orientation of the tibial and femoral mechanical axes can be compared to pre-operative measurements taken from imaging techniques, such as x-rays. The leg can be moved from extension to flexion for resection. The leg in flexion is shown in FIG. 7. The surgeon can proceed to resection. The femoral preparation system 100 can be coupled to a cutting guide. The tibial preparation system 200 can be coupled to a cutting guide. The surgical orientation device 300 can be coupled to a cutting guide. The reference sensor 400 can be coupled to a cutting guide. In some embodiments, the resection is for total knee replacement. In some embodiments, the resection is for partial knee replacement. Additional details of cutting guides are disclosed in U.S. patent application Ser. No. 12/509,388 filed Jul. 24, 2009, U.S. application Ser. No. 13/011,815 filed Jan. 21, 2011, U.S. application Ser. No. 13/115,065, filed May 24, 2011, U.S. application Ser. No. 14/399,046 filed Nov. 5, 2014, and U.S. application Ser. No. 14/401,274 filed Nov. 14, 2014, which are all incorporated by reference herein in their entireties for all purposes.

In some methods, the alignment of the tibial and femoral mechanical axes is not determined prior to resection. The surgeon can proceed to resection after the mechanical axes are determined. The surgeon can proceed to resection after the mechanical axes are stored by the surgical orientation device 300. The leg can remain in flexion. The leg can be positioned in flexion for mechanical axis registration and resection.

In some methods, the alignment of the tibial and femoral mechanical axes is determined after resection. In some methods, the alignment of the tibial and femoral mechanical axes is determined before and after resection. In some methods, the alignment of the tibial and femoral mechanical axes is determined only after resection. In some methods, the leg is transitioned to extension for limb alignment measurements after resection. The change in orientation of the tibial and femoral mechanical axes in extension relative to the tibial and femoral mechanical axes in flexion can be determined. The change in orientation of the tibial and femoral mechanical axes can be compared to pre-operative measurements taken from imaging techniques, such as x-rays. The leg can be moved from extension to flexion for further resection.

FIGS. 8 and 9 illustrates calibration of the surgical orientation device 300 and the reference sensor 400. In some methods, the leg is in extension for calibration. In some methods, the leg is in flexion for calibration. In some methods, calibration is optional. In some methods, the surgical orientation device 300 and the reference sensor 400 are calibrated after determination of the tibial and femoral mechanical axes. In some methods, the surgical orientation device 300 and the reference sensor 400 are calibrated before limb alignment measurements. The surgical orientation device 300 can be positioned on the tibial preparation system 200 for calibration. The reference sensor device 400 can be positioned on the tibial preparation system 200 for calibration. The surgical orientation device 300 and the reference sensor 400 can be a known orientation relative to each other when mounted on the tibial preparation system 200. The surgical orientation device 300 and the reference sensor 400 can be zeroed. The surgical orientation device 300 and the reference sensor 400 can reduce errors caused by drift. The surgical orientation device 300 and the reference sensor 400 can be calibrated before the reference sensor 400 is positioned on the femoral preparation system 100 for limb alignment calculations. The reference sensor 400 can be moved back to the femoral preparation system 100 after calibration. The femoral preparation system 100 and the tibial preparation system 200 can include reference sensor device interfaces 104, 204 by which the reference sensor 400 can be coupled to the jig assemblies 102, 202. FIGS. 7 and 8 illustrate an embodiment of the reference sensor device interfaces 104, 204.

Figures 10A, 10B:
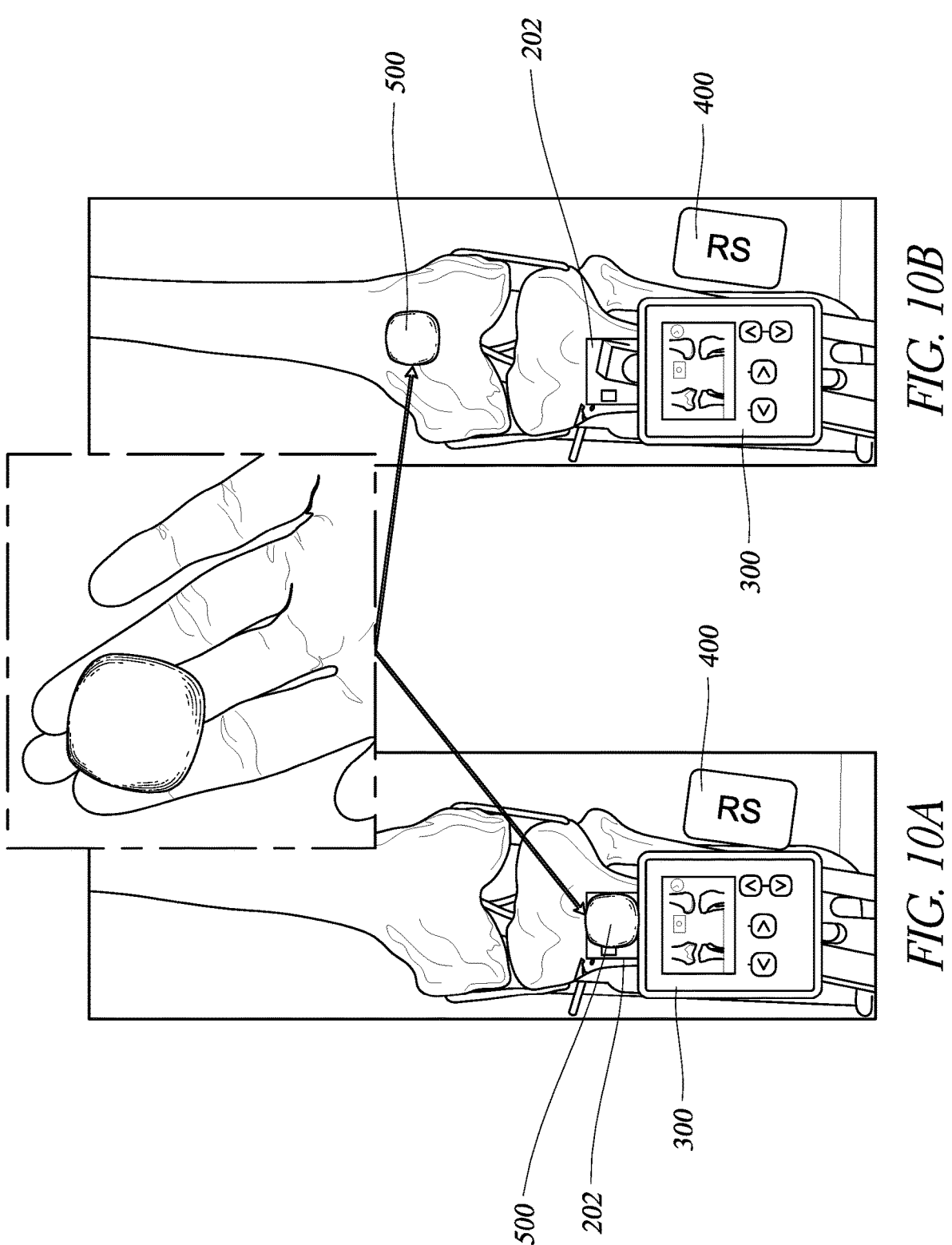
FIGS. 10A-10B illustrate utilization of a module.

FIG. 10A illustrates registration of a module 500. The surgical orientation device 300 can be coupled to the tibial jig assembly 202. The reference sensor 400 can be coupled to the tibial jig assembly 202. In some embodiments, the reference sensor 400 remains stationary relative to the tibia. In some embodiments, the module 500 is provided. The module 500 can include any of the features of the surgical orientation device 300 and the reference sensor 400 described herein. The module 500 can include any sensor described herein. In some embodiments, the reference sensor 400 and the module 500 have the same configuration. In some embodiments, the reference sensor 400 and the module 500 have a different configuration. In some methods, the reference sensor 400 and the module 500 are both utilized. In some methods, the reference sensor 400 is utilized and the module 500 is not utilized. In some embodiments, the reference sensor 400 can be utilized in any method in place of the module 500. In some embodiments, the module 500 can be utilized in any method in place of the reference sensor 400.

The tibial jig assembly 202 can be partially or fully assembled for calibration of the module 500. The surgical orientation device 300 can be coupled to a movable portion of the tibial jig assembly 202. The reference sensor 400 can be coupled a fixed or stationary portion of the tibial jig assembly 202. The surgical orientation device 300 and the reference sensor 400 can be coupled to the tibial jig assembly 202 in the same manner as these devices were coupled when locating the tibial mechanical axis. The tibial jig assembly 202 can include a module interface 250 by which the module 500 can be coupled to the tibial jig assembly 202.

The module 500 can be coupled with the tibial jig assembly 202. In some embodiments, the module 500 couples with a movable portion of the tibial jig assembly 202. In some embodiments, the module 500 couples to the same movable portion of the tibial jig assembly 202 as the surgical orientation device 300. The angle between the surgical orientation device 300 and the module 500 can be fixed during calibration. The module 500 can be calibrated relative to the surgical orientation device 300.

In some embodiments, the module 500 couples with a fixed portion of the tibial jig assembly 202. In some embodiments, the module 500 couples to the same fixed portion of the tibial jig assembly 202 as the reference sensor 400. The angle between the reference sensor 400 and the module 500 can be fixed during calibration. The module 500 can be calibrated relative to the reference sensor 400.

In some methods, the leg is transitioned to extension as shown in FIG. 7A. The module 500 is registered or calibrated relative to the reference sensor 400 and/or the surgical orientation device 300. In some methods, the module 500 is kept stationary on the tibial jig assembly 202 during registration. In some methods, the module 500 can be fixed relative to the tibia. In some methods, the module 500 is coupled to the movable portion of the tibial jig assembly 202 during registration. The module 500 can move relative to the reference sensor 400 during registration. In some methods, the leg is held stationary during registration. In some methods, the tibia is held stationary during registration. In some methods, the sensor of the module 500 is activated during registration. In some methods, gyro integration is initiated during registration.

As shown in FIG. 10B, the module 500 can be moved to the femur during limb alignment and gap measurements. In some methods, the module 500 is moved from a location on the tibial jig assembly 202 to a location on the femoral jig assembly 102. FIG. 7B illustrates a position of the surgical orientation device 300, the reference sensor 400, module 500 during limb alignment and gap measurements. In some embodiments, the surgical orientation device 300 can be coupled to a movable portion of the tibial jig assembly 202. In some embodiments, the surgical orientation device 300 can be coupled to a fixed portion of the tibial jig assembly 202. In some embodiments, the reference sensor 400 can be coupled to a fixed portion of the tibial jig assembly 202. In some embodiments, the reference sensor 400 can be coupled to a fixed portion of the movable jig assembly 202. In some embodiments, the surgical orientation device 300 tracks the position of the tibia during limb alignment and gap measurements. In some embodiments, the orientation device 300 received information from the reference sensor 400 during limb alignment and gap measurements. In some embodiments, the orientation device 300 received information from the module 500 during limb alignment and gap measurements.

In some methods, the module 500 can couple with the femoral jig assembly 102 during limb alignment and gap measurements. In some embodiments, the module 500 couples with a fixed portion of the femoral jig assembly 102. In some embodiments, the module 500 couples with a movable portion of the femoral jig assembly 102. In some methods, the module 500 track the position of the femur during limb alignment and gap measurements.

In some embodiments, the reference sensor 400 can be moved to the femur during limb alignment and gap measurements. In some methods, the reference sensor 400 is moved from a location on the tibial jig assembly 202 to a location on the femoral jig assembly 102. The surgical orientation device 300 can be coupled to the tibial jig assembly 202. The module 500 can be coupled to the tibial jig assembly 202. In some embodiments, the surgical orientation device 300 tracks the position of the tibia during limb alignment and gap measurements. In some embodiments, the orientation device 300 received information from the reference sensor 400 during limb alignment and gap measurements. In some embodiments, the orientation device 300 received information from the module 500 during limb alignment and gap measurements.

In some methods, the reference sensor 400 can couple with the femoral jig assembly 102 during limb alignment and gap measurements. In some embodiments, the reference sensor 400 couples with a fixed portion of the femoral jig assembly 102. In some methods, the reference sensor 400 track the position of the femur during limb alignment and gap measurements.

The surgical orientation device 300, the reference sensor 400, and/or the module 500 can track the position of the tibia and femur during limb alignment and gap measurement. In some embodiments, the surgical orientation device 300 tracks the tibia. In some embodiments, the reference sensor 400 tracks the femur. In some embodiments, the module 500 tracks the femur. Other configurations are contemplated. In some embodiments, the reference sensor 400 can track the position and orientation of the tibia. In some embodiments, the module 500 can track the position and orientation of the tibia. The user can get real-time position and/or orientation signals from the reference sensor 400 and the module 500. The user can get real-time limb alignment measurements. In some embodiments, the tracking of the tibia and the femur is limited in time. In some embodiments, the tracking of the tibia and the femur is limited in time before re-calibration is needed. Re-calibration can include any of the steps described herein for registering or calibrating the module 500.

In some methods, the surgical orientation device 300, the reference sensor 400, and/or the module 500 take static measurements based on the position of the tibia and the femur. In some methods, the surgical orientation device 300, the reference sensor 400 and/or the module 500 take dynamic measurements based on the position of the tibia and the femur during a range of motion. In some embodiments, a valgus stress can be applied to the tibia and returned to a neutral position. Any degree of stress can be applied before the tibia is returned to a neutral position. The leg can be abducted. The load can be applied until the clinician feels resistance. Other ranges and degrees of movement are also possible. In some embodiments, the leg can be swung in one generally looping motion from a home position back to the home position, the looping motion causing both an abduction and raising of the leg. In some embodiments, the tibia and the femur can be placed in approximately 90 degrees of flexion. In some embodiments, the tibia and the femur can be placed in full extension. It is possible to place the leg in other degrees of flexion. Other movements of the leg are contemplated.

In some embodiments, the reference sensor 400 can track the tibia and the module 500 can track the femur, as shown in FIG. 10B. Other configurations are contemplated. In other embodiments, the reference sensor 400 can be coupled to the femoral jig assembly 102 during limb alignment and gap measurements. The module 500 can be coupled to tibial jig assembly 202. In some embodiments, one of the reference sensor 400 and the module 500 couples to the tibia and the other of the reference sensor 400 and the module 500 couples to the femur.

In other embodiments involving the surgical orientation device 300 and the reference sensor 400, the surgical orientation device 300 can be moved to a fixed portion of the tibial jig assembly 202 or the portion of the tibial jig assembly 202 to which the surgical orientation device 300 is mounted can be fixed by activating a clamp or other locking device. The reference sensor 400 can be coupled a fixed portion of the tibial jig assembly 202. The surgical orientation device 300 and the reference sensor 400 can be registered relative to each other. The surgical orientation device 300 can be moved to a fixed portion of the femoral jig assembly 102 during limb alignment and gap measurements.

In some embodiments, one of the surgical orientation device 300 and the reference sensor 400 couples to the tibia and the other of the surgical orientation device 300 and the reference sensor 400 couples to the femur during limb alignment and gap measurements. In some methods, only the surgical orientation device 300 and the reference sensor 400 are utilized during limb alignment and gap measurements.

Figure 11:
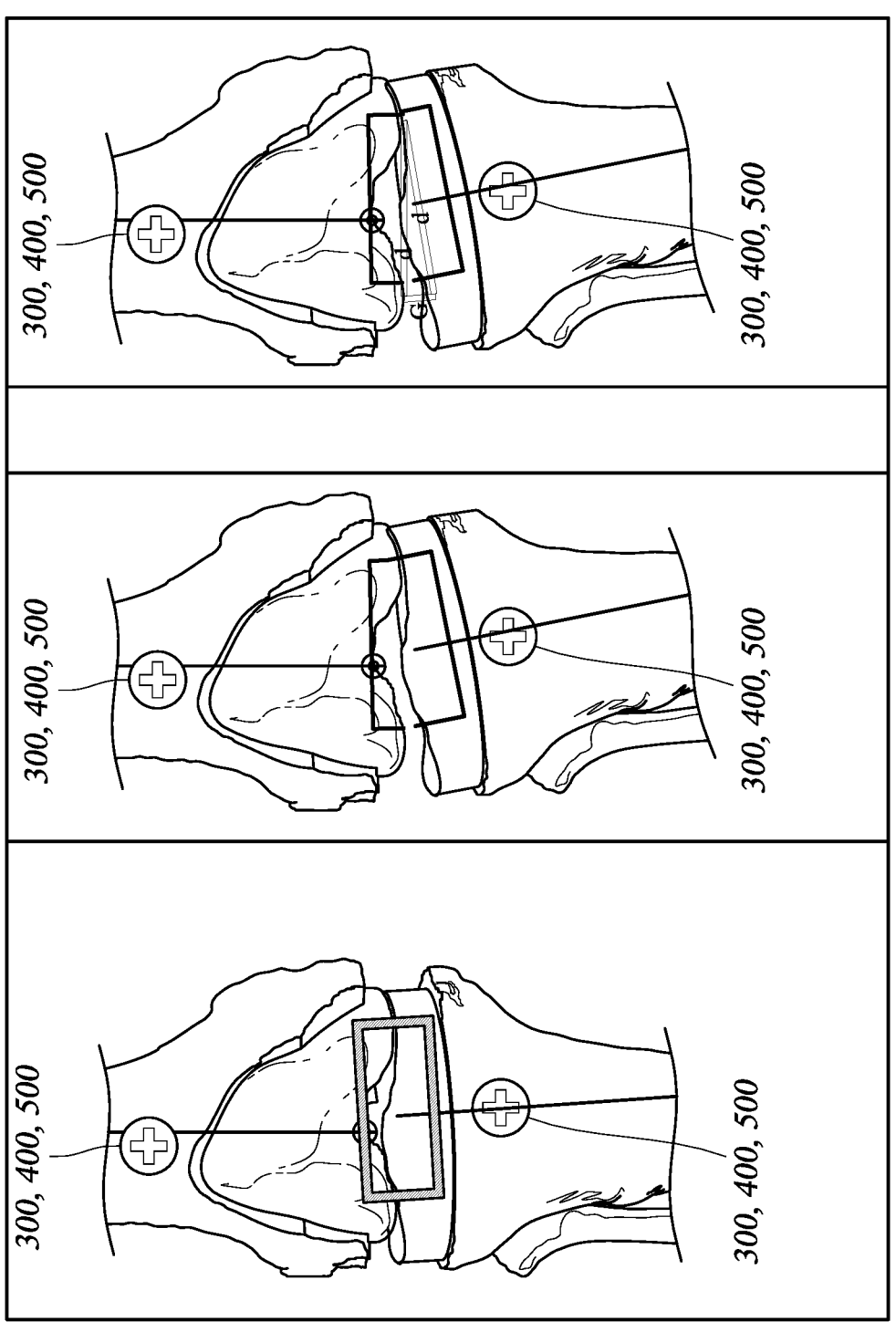
FIG. 11 illustrates gap assessment.
Figure 12:
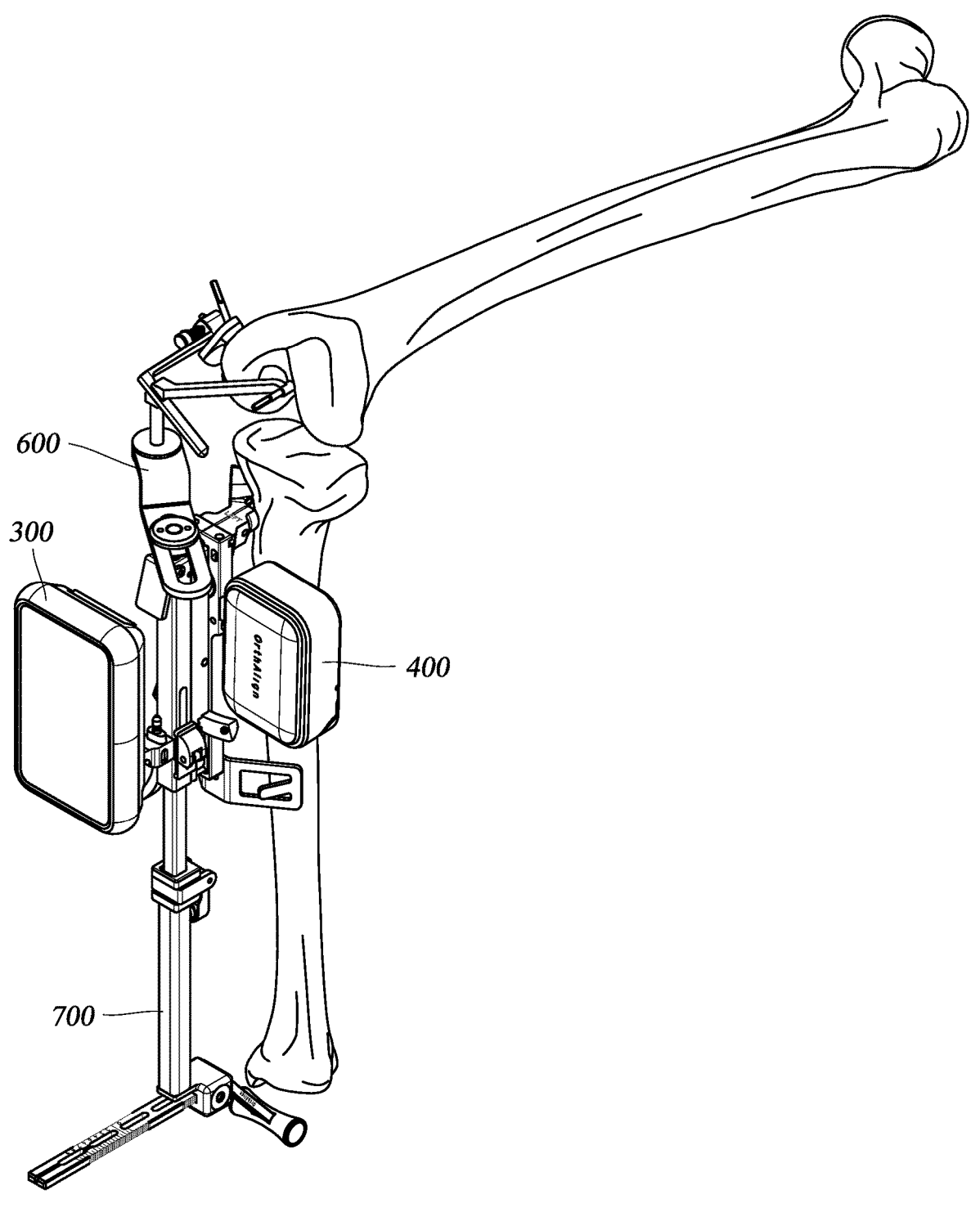
FIG. 12-18 illustrates an embodiment of a system.
Figure 13:
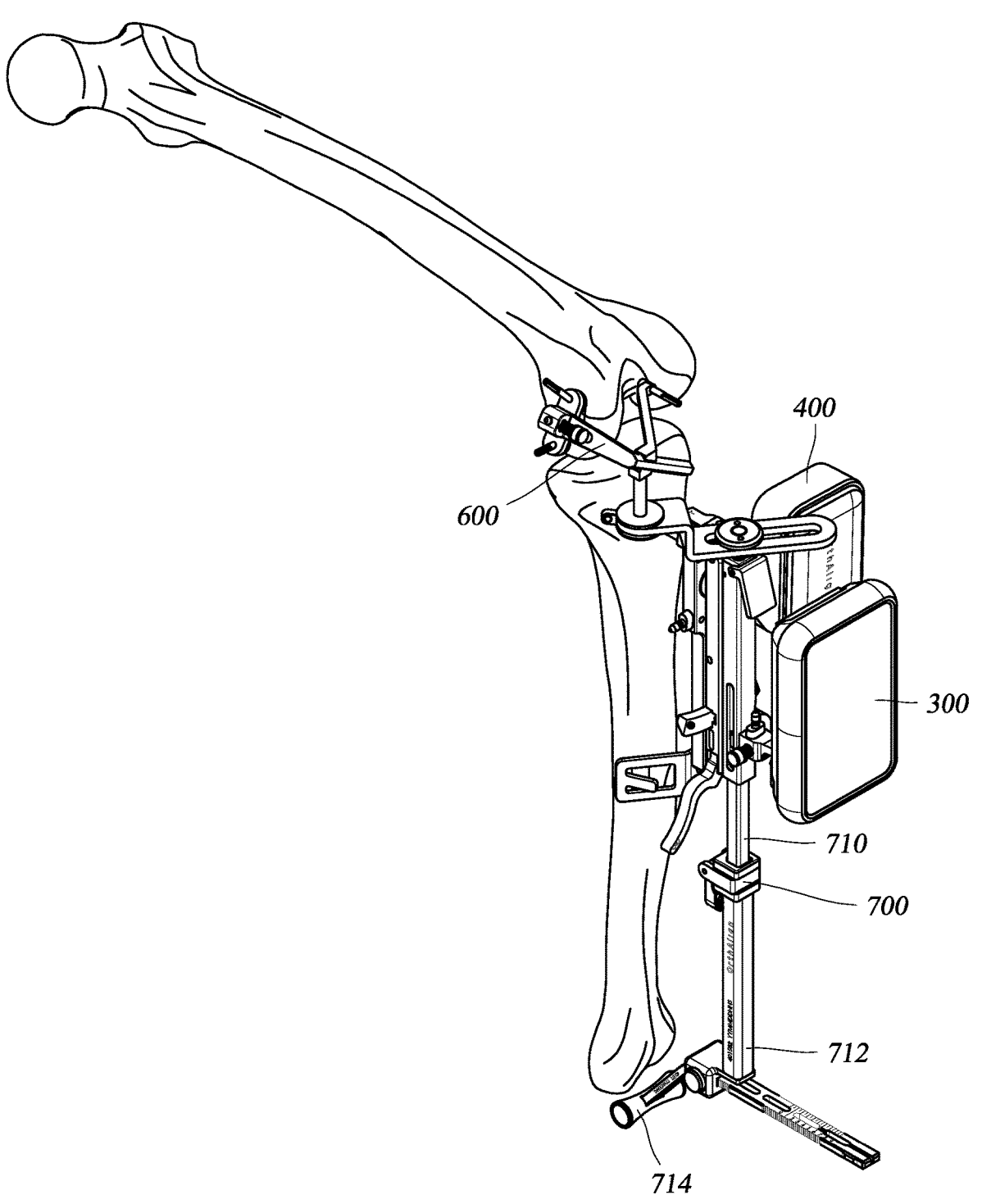
Figure 14:
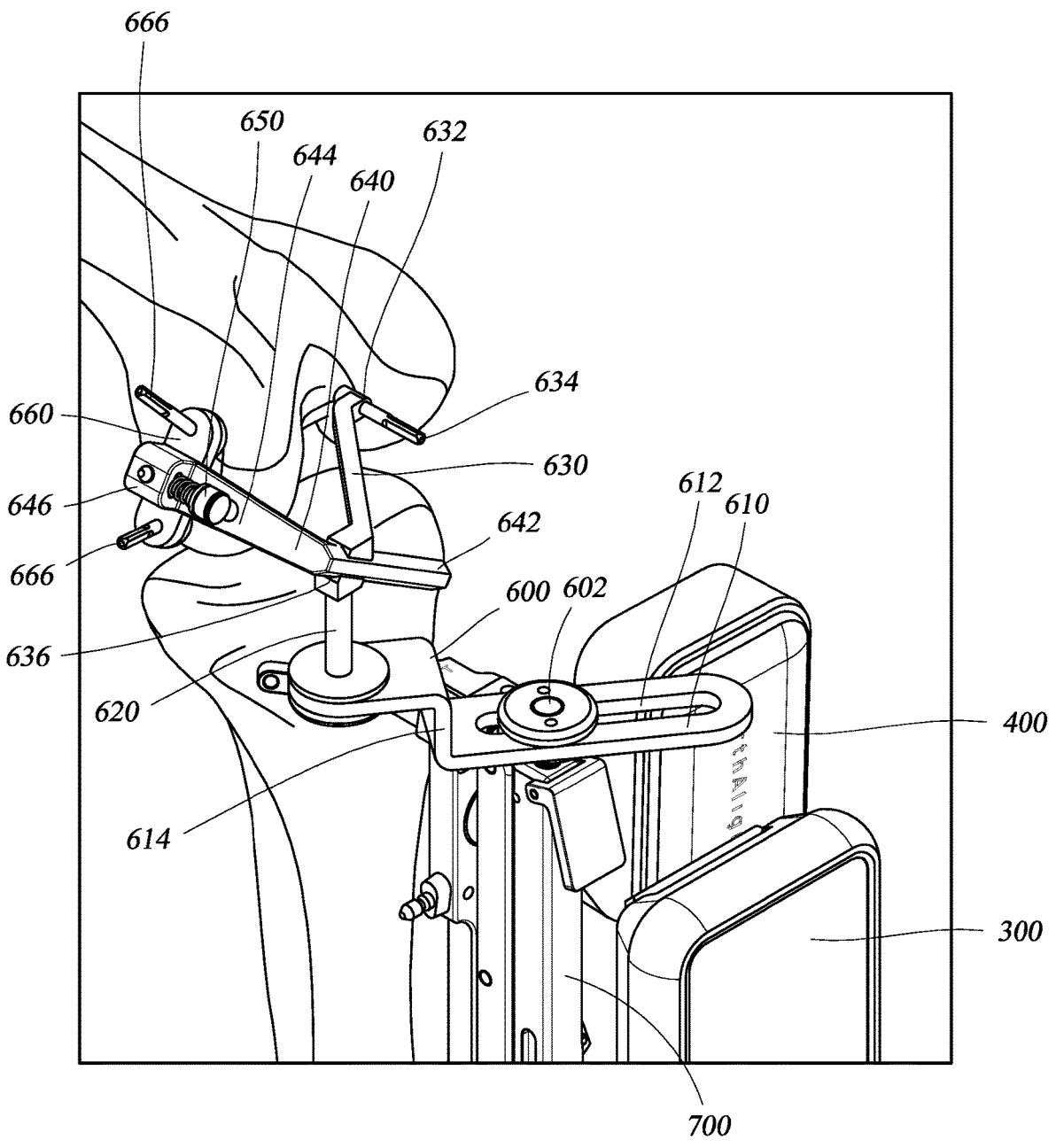
Figure 15:
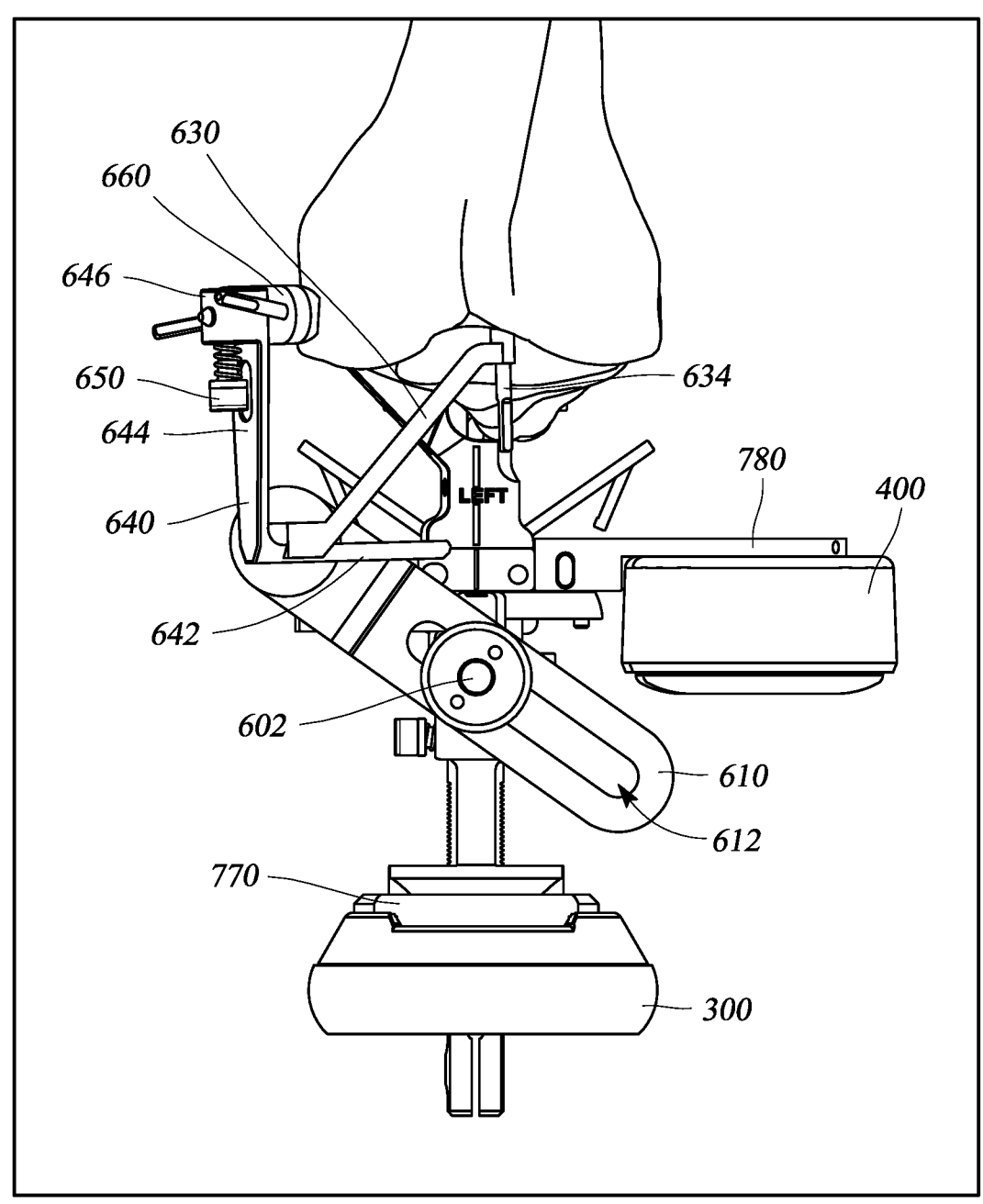
Figure 16:
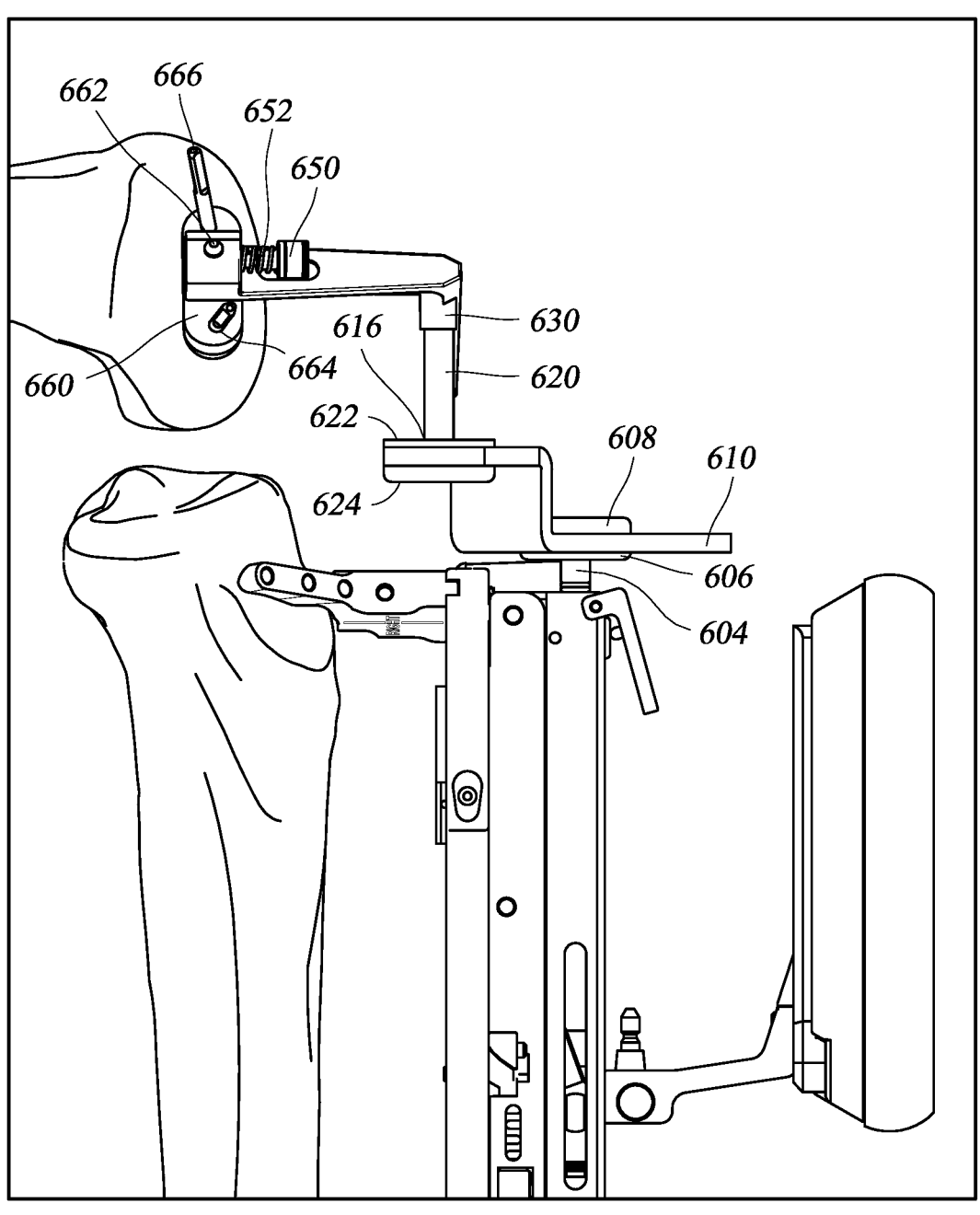
Figure 17:
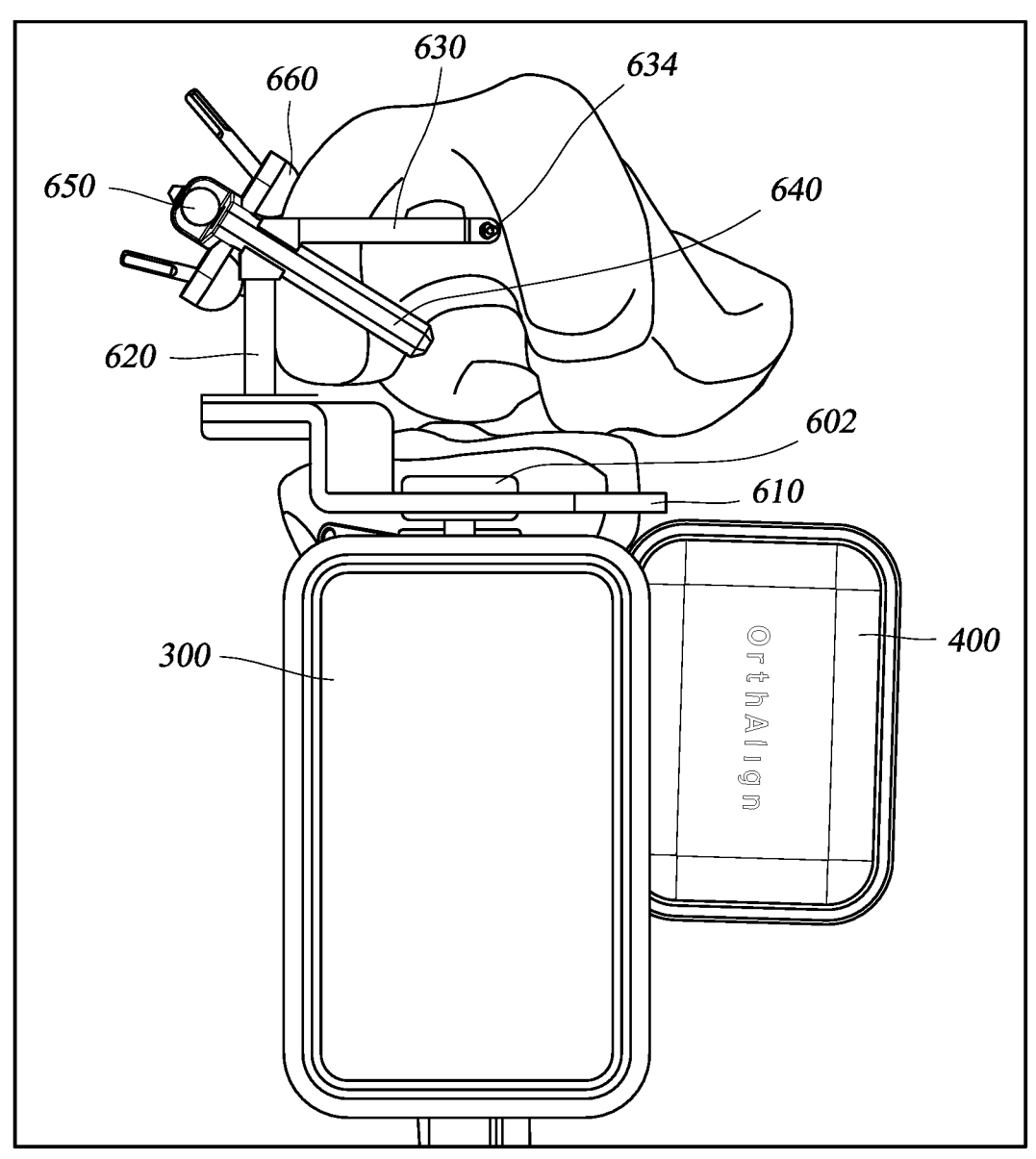
Figure 18:
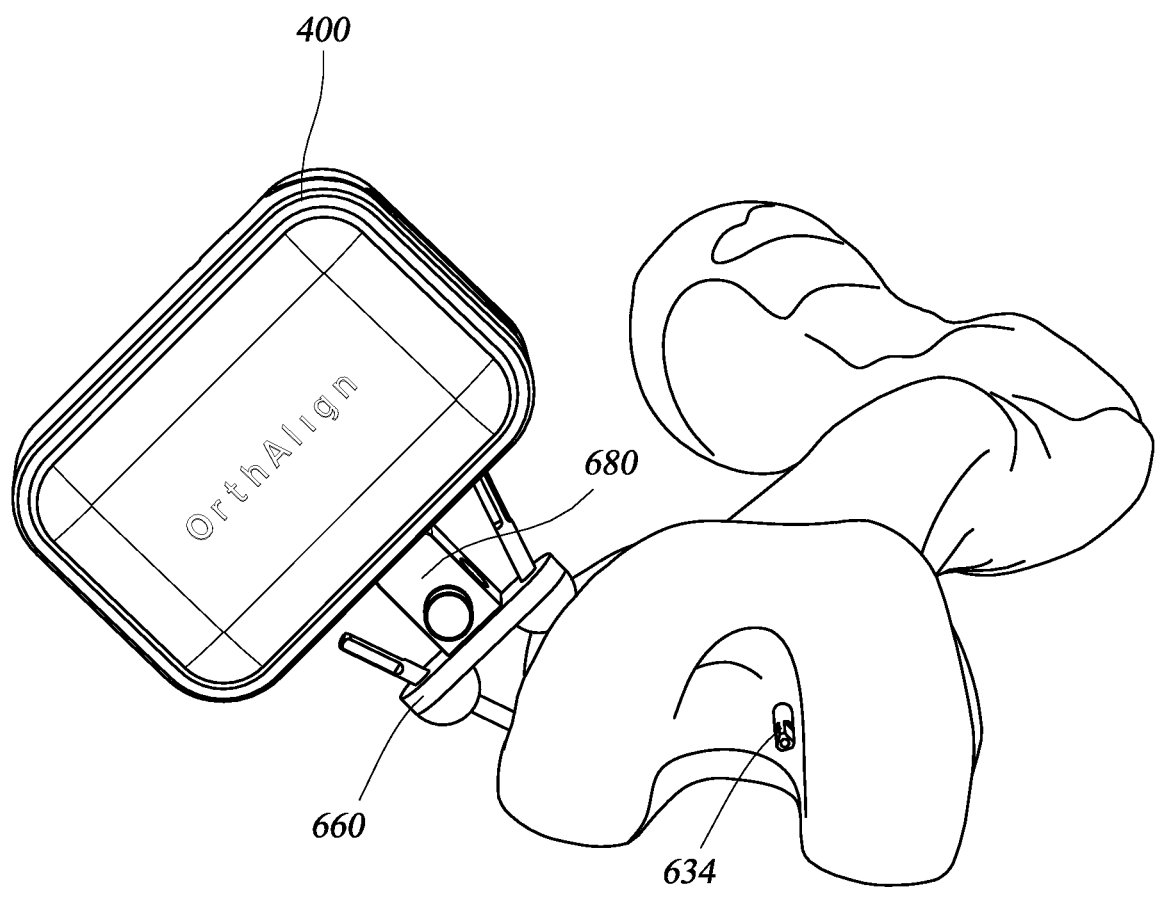

In some methods, the surgeon can perform laxity tests to assess gap balancing of ligaments. The reference sensor 400 and the module 500 can be in the same position for limb alignment and laxity testing, shown in FIG. 10B. In some embodiments, the module 300 can track the position and/or orientation of the tibia. In some embodiments, the reference sensor 400 can track the position and/or orientation of the femur. In some embodiments, the module 500 can track the position and/or orientation of the femur FIG. 11 illustrates gap balancing assessments by at least two of following: the surgical orientation device 300, the reference sensor 400, and the module 500. During gap assessment, one or more of the surgical orientation device 300, the reference sensor 400, and the module 500 is mounted on tibia. During gap assessment, one or more of the surgical orientation device 300, the reference sensor 400, and the module 500 is mounted on femur. In some methods, the surgical orientation device 300 and the reference sensor 400 perform gap balancing before limb alignment measurements. In some methods, the surgical orientation device 300 and the reference sensor 400 perform gap balancing after limb alignment measurements. In some methods, the surgical orientation device 300 and the reference sensor 400 perform gap balancing when the leg is in extension for limb alignment measurements. In FIG. 11, the surgical orientation device 300, the reference sensor 400, and the module 500 are shown as icons. In some methods, the surgical orientation device 300 is positioned on the tibia. In some methods, the reference sensor 400 is positioned on the femur. In some methods, the reference sensor 400 can be positioned on the tibia and the module 500 can be positioned on the femur, or vice versa. In some methods, the reference sensor 400 and the surgical orientation device 300 are utilized. The reference sensor 400 can be positioned on the tibia and the surgical orientation device 300 can be positioned on the femur, or vice versa. In some methods, the module 500 and the surgical orientation device 300 are utilized. The module 500 can be positioned on the femur and the surgical orientation device 300 can be positioned on the tibia, or vice versa. In some methods, the tibial mechanical axis has been calculated and the femoral mechanical axis has been calculated prior to gap balancing assessments. In some methods, resection has been performed prior to gap balancing measurement. In some methods, limb alignment measurements have been performed prior to gap balancing measurements.

During gap measurements, at least one of the surgical orientation device 300, the reference sensor 400, and the module 500 can track the position and/or orientation of the tibia. During gap measurements, at least one of the surgical orientation device 300, the reference sensor 400, and the module 500 can track the position and/or orientation of the femur. During gap measurements, the reference sensor 400 can track the position and/or orientation of the tibia, and the module 500 can track the position and/or orientation of the femur with the arrangement shown in FIG. 11. In some methods, gap balancing is performed with a trial implant or an implant. In some methods, gap balancing is performed with at least one implant positioned between the tibia and the femur. The leg can be positioned in extension. The angle between the reference sensor 400 and the module 500 can be determined with the condyles touching. This angle can be registered as 0 degrees. The tibia and the femur can be taken through a range of motion. In some embodiments, a varus force is applied to the tibia and the angle between the surgical orientation device 300, the reference sensor 400, and/or the module 500 on the tibia and the surgical orientation device 300, the reference sensor 400, and/or the module 500 on the femur can be determined. In some embodiments, a force is applied to the tibia and the angle between the surgical orientation device 300, the reference sensor 400 and/or the module 500 on the tibia and the surgical orientation device 300, the reference sensor 400, and/or the module 500 on the femur is determined. In some embodiments, a varus force is applied to the tibia and the angle between the surgical orientation device 300 on the tibia and the reference sensor 400 on the femur can be determined. The intercondylar distance can be known. The intercondylar distance can be determined from images, such as x-rays. The intercondylar distance can be measured during surgery. This distance can be an input into the surgical orientation device 300. In the illustrated example, the intercondylar distance is 55 mm. The gap due to varus force can be determined based on a geometric relationship based on the known applied varus force and the intercondylar distance.

During gap assessment, the tibia and the femur can be taken through a range of motion as a valgus force is applied. In some embodiments, a valgus force is applied to the tibia and the angle between the surgical orientation device 300, the reference sensor 400 and/or the module 500 on the tibia and the surgical orientation device 300, the reference sensor 400, and/or the module 500 on the femur can be determined. In some embodiments, a force is applied to the tibia. The angle between the surgical orientation device 300, the reference sensor 400 and/or the module 500 on the tibia and the surgical orientation device 300, the reference sensor 400, and/or the module 500 on the femur is determined when the force is applied. In some embodiments, a valgus force is applied to the tibia and the angle between the surgical orientation device 300 on the tibia and the reference sensor 400 on the femur can be determined. The intercondylar distance can be known. The gap due to valgus force can be determined based on a geometric relationship in the same manner as the gap due to varus force.

The gap can be calculated by applying a force and measuring the change in angle from the femoral mechanical axis and the tibial mechanical axis. This angle and the intercondylar distance can provide an estimate of the gap. In some methods, the user applies a varus torque. In some methods, the user applies a valgus torque. In some methods, the user applies a varus then a valgus torque. In some methods, the user applies a valgus torque then a varus torque. In some methods, the user applies varus and/or valgus force to the knee in extension. In some methods, the user applies varus and/or valgus force to the knee in flexion. In some methods, the user applies varus force in flexion and extension. In some methods, the user applies valgus force in flexion and extension.

One or more of the surgical orientation device 300, the reference sensor 400, and the module 500 can calculate the gap distance. The gap distance is a product of the measured angles between the surgical orientation device 300, the reference sensor 400 and/or the module 500 on the tibia and the surgical orientation device 300, the reference sensor 400, and/or the module 500 on the femur. The gap distance is a product of the known intercondylar distance. In some embodiments, dynamic gap heights provide insight into medial/lateral ligament tension. The gap heights can provide insight into soft tissue balancing. The gap measurements can be assessed before resections. The gap can be assessed after resections. The gap can be assessed before and after resections. The gap can be assessed with a plurality of implants or trial implants.

The surgical orientation device 300, the reference sensor 400, and/or the module 500 can be used to measure and record the location of anatomical landmarks used in a knee procedure. The surgical orientation device 300, the reference sensor 400, and/or the module 500 can be used to determine the location of a proximal or distal point of the mechanical axis of the tibia. The surgical orientation device 300, the reference sensor 400, and/or the module 500 can be used to determine the location of a proximal or distal point of the mechanical axis of the femur. The surgical orientation device 300, the reference sensor 400, and/or the module 500 can be used to perform limb balancing measurements. The surgical orientation device 300, the reference sensor 400, and/or the module 500 can be used to perform gap balancing measurements. These measurements can improve patient outcomes by quantifying limb alignment, improving implant selection, and/or improving implant placement.

The surgical orientation device 300, the reference sensor 400, and/or the module 500 can include one or more inertial sensors. The inertial sensors can track orientation and/or position of the tibia and the femur during limb alignment and gap measurements. The sensors in the surgical orientation device 300 and the reference sensor 400 can determine a mechanical axis of the femur and a mechanical axis of the tibia. These mechanical axes can guide cutting blocks for the desired resections. These mechanical axes can also be utilized for limb balancing measurements. These mechanical axes can also be utilized for gap measurements.

The surgical orientation device 300, the reference sensor 400, and/or the module 500 can comprise at least one inertial sensor, such as an accelerometer, a gyroscope, or a combination of these sensors and other sensors. The surgical orientation device 300, the reference sensor 400, and/or the module 500 can utilize sensors other than optical trackers. The surgical orientation device 300, the reference sensor 400, and/or the module 500 can measure acceleration. The surgical orientation device 300, the reference sensor 400, and/or the module 500 can measure velocity. The surgical orientation device 300, the reference sensor 400, and/or the module 500 can measure physical properties of the bones to which they are attached. In some embodiments, the surgical orientation device 300, the reference sensor 400, and the module 500 can include a three axis accelerometer to detect orientation relative to gravity and a plurality of gyroscopes to detect rotation. Other sensors could be used in various modifications.

The surgical orientation device 300, the reference sensor 400, and/or the module 500 can include one or more sensors that together form an inertial measurement unit (IMU). In some embodiments, the IMU can include a first sensor for determining acceleration and a second sensor for determining gyroscopic positioning. As discussed herein, the first sensor can be an accelerometer and the second sensor can be a gyroscopic sensor. In some embodiments, the sensors can comprise a three-axis gyroscopic sensor and a three-axis accelerometer sensor.

The sensors in the surgical orientation device 300, the reference sensor 400, and/or the module 500 preferably transfer data among themselves and in some cases with external devices such as computers, tablets, and/or smartphones, and external displays. The surgical orientation device 300, the reference sensor 400, and the module 500 can be located within the surgical field. The external device can be location within the surgical field or outside the surgical field. The surgical orientation device 300, the reference sensor 400, and the module 500 can transfer data wirelessly, using Bluetooth, Wifi® or other standard wireless telemetry protocol.

The surgical orientation device 300, the reference sensor 400, and/or the module 500 can include a transmitter for sending data and/or receiving data. In some embodiments, the surgical orientation device 300 can receive data from the reference sensor 400 and the module 500. The surgical orientation device 300, the reference sensor 400, and the module 500 can include a transmitter for sending data or receiving data from an external output device. In some embodiments, the surgical orientation device 300 can send data to the reference sensor 400 and the module 500. In some embodiments, the reference sensor 400 and the module 500 can send data therebetween.

The information from the reference sensor 400 and the module 500 can correspond, for example, to the position and/or orientation of tibia and femur during the limb alignment and/or gap measurements. The information from the reference sensor 400 and the module 500 can correspond, for example, to the position and/or orientation of tibia and femur during gap measurements. The information from the reference sensor 400 can correspond, for example, to the position and/or orientation of tibial mechanical axis during a range of motion. The information from the reference sensor 400 can correspond, for example, to the position and/or orientation of tibial mechanical axis during an applied force. The information from the module 500 can correspond, for example, to the position and/or orientation of femoral mechanical axis during a range of motion. The information from the module 500 can correspond, for example, to the position and/or orientation of femoral mechanical axis during an applied force.

The surgical orientation device 300, the reference sensor 400, and/or the module 500 can include an indicator. The indicator can be located on the front surface of the respective device. The indicator can be located on the lateral surfaces of the respective device. The indicator can be a light or LED indicating that the respective device is turned on. The indicator can be a light or LED indicating that the respective device is sensing movement. The indicator can be a separate component from the outer housing of the respective device or can be integrated on or within the outer housing of the respective device.

The surgical orientation device 300, the reference sensor 400, and/or the module 500 can include a display. In some embodiments, the surgical orientation device 300 includes a display. The display can be sized such that a user can readily read numbers, lettering, and/or symbols on the display while performing a medical procedure. The display can be sized such that a user can receive instructions. The display can be sized such that a user can view measurement data.

The surgical orientation device 300, the reference sensor 400, and/or the module 500 can include a user input device. The user input device can be located on the front surface of the respective device. The user input device can be located on the lateral surfaces of the respective device. The user input device can comprise a touchscreen. The user input device can comprise one or more buttons. The user input device can comprise one or more switches. The user input device can comprise one or more scroll wheels. The user input device can be activated, for example, by a finger, hand, and/or instrument to select a mode or modes of operation of the respective device. The user input device can be a separate component from the outer housing of the respective device or can be integrated on or within the outer housing of the respective device. In some embodiments, the user input device is a separate component from the housing. For example, the user input device can comprise a remote input device coupled to the respective device via a wired or wireless connection. The respective device can include a means to receive an input by the user.

The surgical orientation device 300, the reference sensor 400, and/or the module 500 can include one or more functional components configured to sense position, orientation, or movement. The surgical orientation device 300, the reference sensor 400, and the module 500 can comprise an electronic control unit that communicates with one or more inertial sensors. The surgical orientation device 300, the reference sensor 400, and the module 500 can comprise a power supply. The surgical orientation device 300, the reference sensor 400, and the module 500 can comprise internal memory.

The surgical orientation device 300, the reference sensor 400, and/or the module 500 can communicate with an external memory. The surgical orientation device 300, the reference sensor 400, and the module 500 can communicate with the external output device described herein. In some embodiments, the external output device can include the external memory. The external memory can be a separate component from the external output device or can be integrated on or within the external output device. The external output device can allow a surgeon, medical personnel, and/or other user to operate the surgical orientation device 300, the reference sensor 400, and the module 500 with ease, efficiency, and accuracy.

In some embodiments, the electronic control unit of the surgical orientation device 300, the reference sensor 400, and/or the module 500 receives input from the one or more sensors of the surgical orientation device 300, the reference sensor 400, and/or the module 500. The electronic control unit can control and/or transmit output to the external memory. The electronic control unit can control and/or transmit output to the external output device. The electronic control unit can be configured to receive and send electronic data. The electronic control unit can be configured to perform calculations based on received electronic data. The electronic control unit can include a transmitter. The electronic control unit can transfer data wirelessly, using Bluetooth™, Bluetooth Low Energy™, Wifi® or other standard wireless telemetry protocol. The electronic control unit can include a BlueTooth™ radio. The electronic control unit can include Bluetooth Low Energy™ radio. In some embodiments, the surgical orientation device 300, the reference sensor 400, and/or the module 500 can include a wireless module. In some embodiments, the surgical orientation device 300, the reference sensor 400, and/or the module 500 comprises at least one accelerometer, at least one gyroscope, and an wireless module.

In certain embodiments, the electronic control unit of the surgical orientation device 300, the reference sensor 400, and/or the module 500 can be configured to convert the electronic data from a machine-readable format to a human readable format for presentation on the external output device or a display of the surgical orientation device 300, the reference sensor 400, and/or the module 500.

The electronic control unit of the surgical orientation device 300, the reference sensor 400, and/or the module 500 can communicate with internal memory to retrieve and/or store data. The electronic control unit of the surgical orientation device 300, the reference sensor 400, and/or the module 500 can communicate with external memory to retrieve and/or store data. The electronic control unit can communicate with internal memory and/or external memory to retrieve program instructions for software and/or hardware. The internal memory and the external memory can include random access memory ("RAM"), such as static RAM, for temporary storage of information and/or read only memory ("ROM"), such as flash memory, for more permanent storage of information. The external memory can be integrated into a cloud database. The external output device can retrieve data from a cloud database. The surgical orientation device 300, the reference sensor 400, and/or the module 500 can interact with the external memory via cloud integration. The external memory can be a server.

The electronic control unit of the surgical orientation device 300, the reference sensor 400, and/or the module 500 can be configured to receive the real-time data from the one or more sensors. The electronic control unit can be configured to use the sensor data to determine, estimate, and/or calculate a mechanical axis of the tibia. The electronic control unit can be configured to use the sensor data to determine, estimate, and/or calculate a mechanical axis of the femur. The electronic control unit can be configured to use the sensor data to determine, estimate, and/or calculate the alignment between the tibial and femoral mechanical axes. The electronic control unit 20 can be configured to use the sensor data to determine, estimate, and/or calculate limb alignment. The electronic control unit 20 can be configured to use the sensor data to determine, estimate, and/or calculate the gap distance under varus/valgus force.

In some embodiments, the one or more sensors of the surgical orientation device 300, the reference sensor 400, and/or the module 500 can comprise at least one orientation sensor configured to provide real-time data to the electronic control unit related to the motion, orientation, and/or position of the corresponding anatomy of the patient. In some embodiments, the one or more sensors can comprise at least one gyroscopic sensor, accelerometer sensor, tilt sensor, magnetometer and/or other similar device or devices. The one or more sensors can be configured to measure the alignment of the mechanical axes of the leg. In some embodiments, the one or more sensors can be configured to provide measurements relative to a reference point(s), line(s), plane(s), and/or gravitational zero. Gravitational zero, as referred to herein, refers generally to an orientation in which an axis of the sensor is perpendicular to the force of gravity, and thereby experiences no angular offset, for example tilt, pitch, roll, or yaw, relative to a gravitational force vector. In some embodiments, the one or more sensors can be configured to provide measurements for use in dead reckoning or inertial navigation systems.

In some embodiments, the surgical orientation device 300, the reference sensor 400, and/or the module 500 can collect data relative to a coordinate system. The surgical orientation device 300, the reference sensor 400, and/or the module 500 can register to a global coordinate system. The surgical orientation device 300, the reference sensor 400, and/or the module 500 can synchronize with the global coordinate system. The surgical orientation device 300, the reference sensor 400, and/or the module 500 can register to a coordinate system including the mechanical axis of the tibia. The surgical orientation device 300, the reference sensor 400, and/or the module 500 can register to a coordinate system including the mechanical axis of the femur. The surgical orientation device 300, the reference sensor 400, and/or the module 500 can register to a coordinate system including an origin point. The surgical orientation device 300, the reference sensor 400, and/or the module 500 can register to a coordinate system related to a standing lateral film or x-ray. The surgical orientation device 300, the reference sensor 400, and/or the module 500 can register to a coordinate system related to an anterior/posterior x-ray. The surgical orientation device 300, the reference sensor 400, and/or the module 500 can register to a coordinate system determined during calibration or registration.

In some methods, the surgical orientation device 300 and/or the reference sensor 400 can determine the orientation of the tibia during limb alignment measurements. In some methods, the module 500 can determine the orientation of the femur during limb alignment measurements. The surgical orientation device 300, the reference sensor 400, and/or the module 500 can determine the orientation of the femur relative to the tibia. In some methods, the surgical orientation device 300 and/or the reference sensor 400 can determine the orientation of the tibial mechanical axis. In some methods, the surgical orientation device 300 and/or the reference sensor 400 can determine the orientation of the femoral mechanical axis. The surgical orientation device 300, the reference sensor 400, and/or the module 500 can track these mechanical axes through a range of motions. The systems can methods can determine various measurements related to limb alignment, including alignment of the femur and the tibia. The systems can methods can determine various measurements related to the gap including gap measurements under an applied force.

The systems and methods can determine an overall varus/valgus limb alignment angle. The systems and methods can determine an overall varus/valgus limb alignment angle while leg is in flexion. The systems and methods can determine an overall varus/valgus limb alignment angle while the leg is in extension. The systems and methods can determine an overall varus/valgus limb alignment angle through a range of motion. Varus/valgus relates to the angulation within the shaft of a bone or at a joint. Valgus relates to the distal part of the joint being more lateral and varus relates to the distal part of the joint being more medial.

In normal knee alignment, the mechanical axis of the tibia and the femur are roughly aligned. In cases with misalignment, an angulation occurs between the mechanical axes of the tibia and the femur. In varus, there is a greater compressive force across the medial condyle than across the lateral condyle. In valgus, there is a greater compressive force across the lateral condyle than across the medial condyle.

The surgical orientation device 300, the reference sensor 400, and/or the module 500 can determine the overall varus/valgus limb alignment angle by determining the relationship between the tibial and femoral mechanical axes. In some methods, this is a static determination when the knee is in flexion. In some methods, this is a static determination when the knee is in extension. In some methods, this is a dynamic determination when the knee is taken through a range of motion, for instance from flexion to extension or extension to flexion.

The surgical orientation device 300, the reference sensor 400, and/or the module 500 can determine the overall varus/valgus limb alignment angle. In some methods, this angle can be determined before any resections. The surgical orientation device 300, the reference sensor 400, and/or the module 500 can determine the overall varus/valgus limb alignment angle post-operatively. The surgical orientation device 300, the reference sensor 400, and/or the module 500 can determine the overall varus/valgus limb alignment angle during trial reduction. One or more trial implants can be positioned between the tibia and the femur. The knee can be positioned or taken through a range of motion. The surgical orientation device 300, the reference sensor 400, and/or the module 500 can determine the overall varus/valgus limb alignment angle for each of the trial implants. The trial implant that achieves the target varus/valgus limb alignment can be selected. An implant corresponding to the trial implant can be implanted.

The systems and methods can measure range of motion by measuring overall change from maximum extension to maximum flexion. The systems and methods can determine an overall anterior/posterior (flexion/extension) limb alignment angle. The systems and methods can determine an overall knee flexion angle while leg is in flexion. The systems and methods can determine an overall knee extension angle while the leg is in extension. The systems and methods can determine an overall anterior/posterior (flexion/extension) limb alignment angle through a range of motion. Knee flexion is the bending of the knee joint to bring the foot toward the posterior thigh. Knee extension is the straightening of the knee joint. Flexion and extension relate to the joint movement of the knee. Normal range of motion of the knee is approximately 0° extension and approximately 140° flexion. Certain patients can have reduced flexion/extension.

The surgical orientation device 300, the reference sensor 400, and/or the module 500 can determine limb alignment statically in flexion. The surgical orientation device 300, the reference sensor 400, and/or the module 500 can determine limb alignment statically in extension. The surgical orientation device 300, the reference sensor 400, and/or the module 500 can determine limb alignment dynamically when the knee is taken through a range of motion. The surgical orientation device 300, the reference sensor 400, and/or the module 500 can determine the knee extension angle and the knee flexion angle by determining the relationship between the tibial and femoral mechanical axes.

The surgical orientation device 300, the reference sensor 400, and/or the module 500 can determine the overall knee extension angle and the knee flexion angle before any resections. The surgical orientation device 300, the reference sensor 400, and/or the module 500 can determine the knee extension angle and the knee flexion angle after any resections. The surgical orientation device 300, the reference sensor 400, and/or the module 500 can determine the overall knee extension angle and the knee flexion angle during trial reduction. One or more trial implants can be positioned between the tibia and the femur. The knee can be positioned or taken through a range of motion. The surgical orientation device 300, the reference sensor 400, and/or the module 500 can determine the overall knee extension angle and the knee flexion angle for each of the trial implants. The trial implant that achieves the target knee extension angle and the knee flexion angle can be selected. For instance, the trial implant can improve the range of motion of the patient toward a normal range of motion. For instance, the trial implant can allow for full extension. For instance, the trial implant can allow for full flexion. An implant corresponding to the trial implant can be implanted.

The systems and methods can calculate the gap space. The systems and methods can calculate the gap space while leg is in flexion. The systems and methods can calculate the gap space while the leg is in extension. The systems and methods can calculate the gap space through a range of motion. Gap space relates to the distance between the medial and lateral femoral condyles and the tibial plateau. In some methods, the gap space can be calculated as the gap opening from a single femoral condyle to the tibial plateau assuming contact between the tibial plateau and femoral condyle of the other compartment. If an implant or trial implant is positioned in the gap space, the gap distance can related to the distance between medial and lateral femoral condyles and the implant or trial implant.

In healthy knees, there is a layer of cartilage separating the ends of the tibia and femur. Due to variations of wear between the medial and lateral femoral condyles against the tibial condyles in arthritic knees, the gap between the plateaus of the tibia and the femur can narrow symmetrically or asymmetrically.

The surgical orientation device 300, the reference sensor 400, and/or the module 500 can calculate the gap space by determining the relationship between the tibia and femur. In some methods, the gap space is calculated, at least in part, by a distance measurement. In some methods, the gap space is calculated, at least in part, by an inertial measurement. In some methods, this is a static determination when the knee is in flexion. In some methods, this is a static determination when the knee is in extension. In some methods, this is a dynamic determination when the knee is taken through a range of motion, for instance from flexion to extension or extension to flexion.

The surgical orientation device 300, the reference sensor 400, and/or the module 500 can determine the gap space before any resections. The surgical orientation device 300, the reference sensor 400, and/or the module 500 can determine the gap space after any resections. The surgical orientation device 300, the reference sensor 400, and/or the module 500 can determine the gap space during trial reduction. One or more trial implants can be positioned between the tibia and the femur. The knee can be positioned or taken through a range of motion. The surgical orientation device 300, the reference sensor 400, and/or the module 500 can determine the gap space each of the trial implants. The trial implant that achieves the target gap space can be selected. An implant corresponding to the trial implant can be implanted.

The systems and methods can estimate a limb alignment angle based on the navigated tibia resection angle. The systems and methods can estimate a limb alignment angle based on the cut tibia resection angle. The systems and methods can estimate the limb alignment angle while leg is in flexion. The systems and methods can estimate the limb alignment angle while the leg is in extension. The systems and methods can estimate the limb alignment angle through a range of motion. In some embodiments, the estimated limb alignment angle is varus/valgus. In some embodiments, the estimated limb alignment angle is flexion/extension.

The navigated tibia resection angle can be a target angle determined pre-operatively. The navigated tibia resection angle can be a target angle determined based on pre-operative imaging. The navigated tibia resection angle can be a target angle that is navigated by adjusting the tibial preparation system 200. The cut tibia resection angle can be based on the anatomy of the tibia after resection. The cut tibia resection angle can be determined intraoperatively. The cut tibia resection angle can be determined after the resection occurs for cut verification. In some embodiments, the navigated tibia resection angle and the cut tibia resection angle are the same angle.

The navigated femoral resection angle can be a target angle determined pre-operatively. The navigated femoral resection angle can be a target angle determined based on pre-operative imaging. The navigated femoral resection angle can be a target angle that is navigated by adjusting the femoral preparation system 100. The cut femoral resection angle can be based on the anatomy of the femoral after resection. The cut femoral resection angle can be determined intraoperatively. The cut femoral resection angle can be determined after the resection occurs for cut verification. In some embodiments, the navigated femoral resection angle and the cut femoral resection angle are the same angle.

The surgical orientation device 300, the reference sensor 400, and/or the module 500 can determine the limb alignment angle based on the navigated tibia resection angle by determining the relationship between the tibial and femoral mechanical axes. In some methods, this is a static determination when the knee is in flexion. In some methods, this is a static determination when the knee is in extension. In some methods, this is a dynamic determination when the knee is taken through a range of motion, for instance from flexion to extension or extension to flexion.

The surgical orientation device 300, the reference sensor 400, and/or the module 500 can estimate the limb alignment angle pre-operatively. The surgical orientation device 300, the reference sensor 400, and/or the module 500 can estimate the limb alignment angle post-operatively. The surgical orientation device 300, the reference sensor 400, and/or the module 500 can estimate the limb alignment angle during trial reduction. One or more trial implants can be positioned between the tibia and the femur. The knee can be positioned or taken through a range of motion. The surgical orientation device 300, the reference sensor 400, and/or the module 500 can estimate the limb alignment angle for each of the trial implants. The trial implant that achieves the target limb alignment can be selected. An implant corresponding to the trial implant can be implanted.

The systems and methods can perform a range of motion calculation. The systems and methods can calculate a range of motion while leg is in flexion. The systems and methods can calculate a range of motion while the leg is in extension. The systems and methods can calculate a range of motion through a range of leg motion. In some embodiments, the calculated range of motion is varus/valgus motion. In some embodiments, the calculated range of motion is flexion/extension motion. In some embodiments, the calculated range of motion is axial rotation.

The surgical orientation device 300, the reference sensor 400, and/or the module 500 can calculate the range of motion by determining the relationship between the tibial and femoral mechanical axes. In some methods, this is a static determination when the knee is in flexion. In some methods, this is a static determination when the knee is in extension. In some methods, this is a dynamic determination when the knee is taken through a range of motion, for instance from flexion to extension or extension to flexion.

The surgical orientation device 300, the reference sensor 400, and/or the module 500 can determine range of motion pre-operatively. The surgical orientation device 300, the reference sensor 400, and/or the module 500 can determine range of motion post-operatively. The surgical orientation device 300, the reference sensor 400, and/or the module 500 can determine range of motion during trial reduction. One or more trial implants can be positioned between the tibia and the femur. The knee can be positioned or taken through a range of motion. The surgical orientation device 300, the reference sensor 400, and/or the module 500 can determine range of motion for each of the trial implants. The trial implant that achieves the target range of motion can be selected. An implant corresponding to the trial implant can be implanted.

The surgical orientation device 300, the reference sensor 400, and/or the module 500 can be utilized to determine static limb alignment angles. The surgical orientation device 300, the reference sensor 400, and/or the module 500 can be utilized to determine dynamic limb alignment angles. Static measurements include measurements of the leg while leg is in a static position. Dynamic measurements include measurement while the femur is moving, the tibia is moving, or both the tibia and the femur are moving.

The surgical orientation device 300, the reference sensor 400, and/or the module 500 can be utilized for unicompartmental knee arthroplasty. The surgical orientation device 300, the reference sensor 400, and/or the module 500 can be utilized for total knee arthroplasty.

The surgical orientation device 300, the reference sensor 400, and/or the module 500 can be utilized for intraoperative measurements. The surgical orientation device 300, the reference sensor 400, and/or the module 500 can be utilized for pre-operative measurements. The surgical orientation device 300, the reference sensor 400, and/or the module 500 can be utilized for post-operative measurements.

One or more of the surgical orientation device 300, the reference sensor 400, and/or the module 500 can provide a visual representation to the user. In some embodiments, the surgical orientation device 500 can include a display. The visual representation can include angles, distances, or any other measurement. The visual representation can include limb alignment angles including varus/valgus, medial/lateral, anterior/posterior, and/or flexion/extension. The visual representation can include a graphical representation of tibia, femur, and/or leg.

One or more of the surgical orientation device 300, the reference sensor 400, and/or the module 500 can be reusable. One or more of the surgical orientation device 300, the reference sensor 400, and/or the module 500 can be sterilized. In some embodiments, the surgical orientation device 300, the reference sensor 400, and the module 500 can be able to be re-sterilized. One or more of the surgical orientation device 300, the reference sensor 400, and/or the module 500 can be sterilized in an autoclave. One or more of the surgical orientation device 300, the reference sensor 400, and/or the module 500 can be disposable. In some embodiments, the surgical orientation device 300, the reference sensor 400, and the module 500 can be single use.

One or more of the surgical orientation device 300, the reference sensor 400, and/or the module 500 can include one or more inertial sensors. One or more of the surgical orientation device 300, the reference sensor 400, and/or the module 500 can include an accelerometer. One or more of the surgical orientation device 300, the reference sensor 400, and/or the module 500 can include a gyroscope. One or more of the surgical orientation device 300, the reference sensor 400, and/or the module 500 can include a wireless module. One or more of the surgical orientation device 300, the reference sensor 400, and/or the module 500 can include at least one inertial sensor and a wireless module. In some embodiments, each of the surgical orientation device 300, the reference sensor 400, and/or the module 500 can include at least one inertial sensor and an wireless module.

One or more of the surgical orientation device 300, the reference sensor 400, and/or the module 500 can be configured to communicate with an external device. One or more of the surgical orientation device 300, the reference sensor 400, and/or the module 500 can be configured to communicate with the cloud. The surgical orientation device 300, the reference sensor 400, and/or the module 500 are configured to communicate therebetween. One or more of the surgical orientation device 300, the reference sensor 400, and/or the module 500 can receive signals related to position and/or orientation. One or more of the surgical orientation device 300, the reference sensor 400, and/or the module 500 can send signals related to position and/or orientation.

One or more of the surgical orientation device 300, the reference sensor 400, and/or the module 500 can have any features of the surgical orientation devices and reference devices described in U.S. patent application Ser. No. 13/115, 065, which is incorporated by reference herein. One or more of the surgical orientation device 300, the reference sensor 400, and/or the module 500 can include any navigation unit containing one or more of an accelerometer, gyroscope, display, touchscreen, buttons, and the wireless module.

In some embodiments, the inertial sensors communicate to central processor. In some embodiments, the reference sensor 400 communicates with a central processor of the surgical orientation device 300. In some embodiments, the reference sensor 400 communicates with a central processor of an external device, such as an external memory or cloud. In some embodiments, the module 500 communicates with a central processor of the surgical orientation device 300. In some embodiments, the module 500 communicates with a central processor of an external device, such as an external memory or cloud. In some embodiments, the surgical orientation device 300 communicates with a central processor of an external device, such as an external memory or cloud. One or more of the surgical orientation device 300, the reference sensor 400, and/or the module 500 communicates with the surgical orientation device 300. One or more of the surgical orientation device 300, the reference sensor 400, and/or the module 500 communicates with an external device such as a computer, tablet or smartphone. One or more of the surgical orientation device 300, the reference sensor 400, and/or the module 500 with any device with a wireless module.

One or more of the surgical orientation device 300, the reference sensor 400, and/or the module 500 can be coupled to one or more of the tibia and the femur. The surgical orientation device 300 and/or the reference sensor 400 can be directly attached to the tibia during tibia preparation. The surgical orientation device 300 and/or the reference sensor 400 can be directly attached to the femur during femur preparation. The surgical orientation device 300 and/or the reference sensor 400 can be directly attached to femur and/or tibia in the open wound.

The femoral preparation system 100 and/or tibial preparation system 200 can include a pinned jig configured to be coupled to the respective bone. The femoral preparation system 100 and/or tibial preparation system 200 can include reference sensor device interfaces 104, 204 by which the reference sensor 400 can be coupled to the jig assemblies 102, 202. The femoral preparation system 100 and/or tibial preparation system 200 can include surgical orientation device interfaces 106, 206 by which the reference sensor 400 can be coupled to the jig assemblies 102, 202. The surgical orientation device 300 and/or the reference sensor 400 can be attached to the assemblies 102, 202 with interfaces 104, 106, 204, 206 percutaneously.

The module 500 can be coupled to one or more of the tibia and the femur. The module 500 can be directly attached to the tibia during limb alignment and gap measurements. The module 500 can be directly attached to the femur during limb alignment and gap measurements. The module 500 can couple to the femoral jig assembly 102. The module 500 can couple to the tibial jig assembly 202. The module 500 can couple to the femoral jig assembly 102 during calibration. The module 500 can couple to the tibial jig assembly 202 during calibration. The module 500 can couple with any interface of the assemblies 102, 202. The module 500 can couple to the assemblies 102, 202 percutaneously.

One or more of the surgical orientation device 300, the reference sensor 400, and/or the module 500 can be coupled to the femur bone. One or more of the surgical orientation device 300, the reference sensor 400, and/or the module 500 can be coupled to the tibia bone. One or more of the surgical orientation device 300, the reference sensor 400, and/or the module 500 can be coupled the skin of the patient. One or more of the surgical orientation device 300, the reference sensor 400, and/or the module 500 can be coupled to the soft tissue of the patient.

One or more of the surgical orientation device 300, the reference sensor 400, and/or the module 500 can comprise an adhesive configured to adhere to the skin of the patient. One or more of the surgical orientation device 300, the reference sensor 400, and/or the module 500 can comprise a wrap or strap configured to encircle a portion of the patient's anatomy. One or more of the surgical orientation device 300, the reference sensor 400, and/or the module 500 can comprise an inertial sensor embedded in a fabric.

The selection and placement of the tibial implant follows completion of the tibial resection. The selection and placement of the femoral implant follows completion of the femoral resection. The tibial implant can be rotated in any direction on the resected tibial surface. The tibial implant can be selected from a plurality of implants that vary in gap height. The tibial implant can be selected from a plurality of implants that vary in varus angle. The tibial implant can be selected from a plurality of implants that vary in valgus angle. The tibial implant can be selected from a plurality of implants that vary in the allowed range of motion. The tibial implant can be selected from a plurality of implants that vary in flexion. The tibial implant can be selected from a plurality of implants that vary in extension.

A more precise and/or quantifiable alignment method is likely to improve implant performance and patient satisfaction. The systems and methods provide, in some embodiments, such more precise and/or quantifiable alignment methods to improve implant performance and patient satisfaction. The systems and methods provide a way to quantify the alignment of the mechanical axes of the tibia and the femur. The systems and methods provide a way to quantify the limb alignment angles. The systems and methods provide a way to quantify the gap height.

The systems and methods can provide a recommendation on the trial implant or implant. The systems and methods can provide an estimated gap distance. The systems and methods provide means to quantify a varus force as a function of an angle measurement. This angle can determine the gap, which is a function of the applied angle and the intercondylar distance. The systems and methods provide a means to quantify a valgus force as a function of an angle measurement. The systems and methods provide a means to quantify an overall knee extension angle. The systems and methods provide a means to quantify an overall knee flexion angle. The systems and methods provide a means to quantify axial rotation. The systems and methods provide a means to quantify the range of motion.

The systems and methods provide, in some embodiments, a method for selecting one or more of the tibial implant and the femoral implant by limb alignment and/or gap measurements based upon the femoral and tibial mechanical axes. For some patients, the femur contacts the tibia at two points:

one medial, and one lateral. As the knee flexes through its range of motion, the location of these contact points on the tibia can vary. There can be medial and lateral contact points throughout the range of motion. The tibial implant and the femoral implant can be selected based the contact point profile. As one example, the tibial implant and the femoral implant can be selected to change the gap. The tibial implant and the femoral implant can be selected to increase or decrease the overall flexion angle.

In some methods, one of the reference sensor 400 and the module 500 is securely attached to each of the femur and tibia. In some methods, the reference sensor 400 attached to the tibia can be aligned approximately with the tibial mechanical axis. In some methods, the module 500 attached to the femur can be aligned approximately with the femoral mechanical axis. The reference sensor 400 and the module 500 are preferably mounted in a manner which allows normal function of the patella to reproduce normal knee kinematics. In some embodiments, a medialized attachment is preferred on both the tibia and femur to better accommodate the typical surgical exposure. The surgical orientation device 300 can also be within the surgical field. In some methods, the surgical orientation device 300 is coupled to the tibial jig assembly 202.

In some methods, the orientation of the tibial and femoral mechanical axis are calculated. The mechanical axes can be calculated relative to the surgical orientation device 300, the reference sensor 400, and/or the module 500. The mechanical axes can be calculated relative to a reference frame including gravity. The mechanical axes can be calculated relative to a global coordinate system. The mechanical axes can be calculated relative to an external reference coordinate system. The mechanical axes can be calculated with an offset based on the configuration of one or more of the tibial jig assembly 202 or the femoral jig assembly 102. The offset can be applied to the calculated mechanical axis to improve accuracy.

In order to establish the characteristics of the knee joint, the surgeon can bring the knee into full extension. The surgeon can bring the knee into full flexion. The surgeon can move the leg through a short arc of motion. The surgeon can pivot about the femoral head in all directions. The surgeon can rotate about the long axis of the leg. The surgeon can apply varus torque to the knee. The surgeon can apply valgus torque to the knee. The surgeon can do one or more of these motions in series. The surgeon can do one or more of these motions in simultaneously. These motions can be performed before resection to establish the characteristics of the knee joint. These motions can be performed after resection to establish the characteristics of the knee joint with a trial implant or implant. These motions can be performed postoperatively to establish the characteristics of the knee joint.

In some methods, the reference sensor 400 and the module 500 can be stationary relative to each other during calibration. The reference sensor 400 and the module 500 can be mounted on the tibial jig assembly 202. The reference sensor 400 and the module 500 can be in a fixed relationship to each other. While stationary, the reference sensor 400 and the module 500 can perform a transfer alignment to calculate the relative misalignment between the reference sensor 400 and the module 500. In some embodiments, the orientation of the module 500 can be established in the frame of reference of the reference sensor 400. In some embodiments, the orientation of the reference sensor 400 and the module 500 can be established in the frame of reference of the surgical orientation device 300.

During limb alignment and/or gap balancing, the knee is then taken through a range of motion. Relative rotations between the tibia and femur are measured by comparing the angular changes recorded by their respective reference sensor 400 and module 500 throughout the range of motion. The inertial measurements can be transmitted to the surgical orientation device 300. These rotations can be resolved into three directions corresponding to the flexion/extension, axial rotation, and varus/valgus directions. The processor of the surgical orientation device 300 can provide a user-readable output related to one or more of these rotations. The user-readable output can be the flexion angle. The user-readable output can be the extension angle. The user-readable output can be the varus angle. The user-readable output can be the valgus angle. The user-readable output can be the axial rotation of the tibial relative to the femur. The user-readable output can an axial rotation measurement. The user-readable output can be a graphical display. The user-readable output can be a graph. The user-readable output can be the varus/valgus angle at different degrees of flexion. The surgical orientation device 300 can display numerical values. The surgical orientation device 300 can display numerical values for the varus/valgus angle at various flexion angles such as 90 degrees or 120 degrees. The surgical orientation device 300 can display numerical values for the rotation angle at various flexion angles such as 90 degrees or 120 degrees.

During trial reduction, the surgeon repeats the transfer alignment. In some methods, the surgeon places the surgical orientation device 300 on the tibia and the reference sensor 400 on the femur. The leg is taken through a range of motion. The surgical orientation device 300 then displays the limb alignment and/or gap balancing measurements related to the trial implant. In some embodiments, the surgical orientation device 300 can compare the inertial sensor output to targets. These targets can be based on published averages for healthy knees. These targets can be based on kinematic measurements taken from the patient prior to resection. These targets can be based on kinematic measurements taken from the contralateral knee.

In some embodiments, the surgical orientation device 300 can provide a recommendation related to the trial implant. In some embodiments, the surgical orientation device 300 can provide a recommendation to change the varus/valgus angle of the trial implant. In some embodiments, the surgical orientation device 300 can provide a recommendation to change the gap height. In some embodiments, the surgical orientation device 300 can provide a recommendation to rotate the trial implant. In some embodiments, the surgical orientation device 300 can provide a recommendation based on the inertial sensor measurements of the reference sensor 400 and the module 500.

In some methods, the surgeon applies alternating varus and valgus torque to the knee in order to gauge the opening allowed in each compartment. This varus or valgus angle can be displayed on the surgical orientation device 300. This measurement can supplement the traditional visual estimation of knee laxity in the varus/valgus direction. This angle provides a means to quantitatively compare the medial and lateral laxity. In some embodiments, the surgeon can utilize inertial data from the reference sensor 400 and/or the module 500 to balance the medial/lateral laxity. In some embodiments, the surgeon can utilize inertial data from the reference sensor 400 and/or the module 500 to release soft tissue around the knee. In some embodiments, the surgeon can utilize inertial data from the reference sensor 400 and/or the module 500 to quantify the laxity of the knee joint. In some embodiments, the surgeon can utilize inertial data from the reference sensor 400 and/or the module 500 to quantify varus/valgus angle at a specific flexion angle. In some embodiments, the surgeon can utilize inertial data from the reference sensor 400 and/or the module 500 to quantify varus/valgus angle through a range of motion.

The surgeon can adjust or replace the trial implant. The process can be repeated until the trial implant is satisfactory. The surgeon can positon the implant based on the trial implant. In some embodiments, the range of motion of the trial implant or implant is stored by the surgical orientation device 300. In some embodiments, the range of motion of the trial implant or implant is transmitted by the surgical orientation device 300 for post-operative comparisons.

FIGS. 12-18 illustrate a femoral preparation system 600 and a tibial preparation system 700. The femoral preparation system 600 can include any component of the femoral preparation system 100 described herein. The tibial preparation system 700 can include any component of the tibial preparation system 200 described herein. The femoral preparation system 600 and the tibial preparation system 700 can include jigs that allow for the placement of the femoral preparation system 600 relative to the tibial preparation system 700.

The femoral preparation system 600 can be used to position the reference sensor 400 relative to the femur. The reference sensor 400 can be positioned laterally relative to the distal end of the femur. The reference sensor 400 can be positioned so that the leg can be placed in extension. The reference sensor 400 can be positioned a known distance from an anatomical landmark. The reference sensor 400 can be positioned at a known angle from an anatomical landmark. The reference sensor 400 can communicate inertial sensor data related to position and orientation to the surgical orientation device 300.

The femoral preparation system 600 is configured to be securely mounted upon the lateral portion of the femur. The femoral preparation system 600 can also include one or more cutting guides to modify a natural femur with a distal femoral resection, enabling a prosthetic component to be securely mounted upon the distal end of the femur as described herein.

The femoral preparation system 600 can include a cutting guide rod 602. The cutting guide rod 602 can couple to the tibial preparation system 700. The cutting guide rod 602 can include a threaded post 604. The threaded post 604 can engage a threaded bore of the tibial preparation system 700. The threaded bore can engage a midline reference probe assembly, as described herein, before the femoral preparation system 600 is mounted thereon. The cutting guide rod 602 can be removable. The cutting guide rod 602 can be rotated to uncouple the femoral preparation system 600 and the tibial preparation system 700. The cutting guide rod 602 can be rotated to couple the femoral preparation system 600 and the tibial preparation system 700. The cutting guide rod 602 can include a flange 606. The cutting guide rod 602 can include a cap 608.

The femoral preparation system 600 can include a cutting guide bracket 610. The cutting guide bracket 610 can include a slot 612. The slot 612 can allow adjustment of the cutting guide bracket 610 relative to the tibial preparation system 700. The slot 612 can allow adjustment of the cutting guide bracket 610 relative to the anatomy of the patient. The cutting guide bracket 610 can slide relative to the cutting guide rod 602. The cutting guide rod 602 can be positioned within the slot 612. The flange 606 can be below the cutting guide bracket 610. The cap 608 can be above the cutting guide bracket 610. The cutting guide bracket 610 can slide relative to the cutting guide rod 602. The cutting guide bracket 610 can rotate relative to the cutting guide rod 602. The cutting guide bracket 610 can be position the femoral preparation system 600 toward the left of the tibial preparation system 700, as shown. The cutting guide bracket 610 can position the femoral preparation system 600 toward the right of the tibial preparation system 700. The cutting guide bracket 610 can be a universal bracket allowing positioning on the left or right of the tibial preparation system 700. The cutting guide bracket 602 can include a step 614. The step 614 can position the cutting guide bracket 602 proximal to the tibial preparation system 700. The step 614 can prevent interference between the cutting guide bracket 610 and another component of the system. The cutting guide bracket 602 can include an opening 616.

The femoral preparation system 600 can include a swivel post 620. The swivel post 620 can include a flange 622. The swivel post 620 can include a cap 624. The opening can allow rotation of the swivel post 620 relative to the cutting guide bracket 602. The opening 616 can allow rotation of the swivel post 620 relative to the anatomy of the patient. The swivel post 620 can rotate relative to the cutting guide bracket 610. The swivel post 620 can be positioned within the opening 616 of the cutting guide bracket 602. The flange 622 can be above the cutting guide bracket 602. The cap 624 can be below the cutting guide bracket 602.

The femoral preparation system 600 can include an extension 630. The extension 630 can be coupled to the swivel post 620. The extension 630 and the swivel post 620 can be separately formed. The extension 630 and the swivel post 620 can be integrally formed. The extension can include an opening 632. The opening 632 can slide to engage a threaded pin 634. The opening 632 can receive the threaded pin 634. The threaded pin 634 can be an intramedullary pin. The length of the extension 630 can be an input into the surgical orientation device 300. The length of the extension 630 can be selected based on the anatomy of the patient. The extension 630 can have a fixed length regardless of the anatomy of the patient. The extension 630 can include a groove 636. The groove 636 can be a keyed groove. The groove 636 can be a dovetail groove. The extension 630 can be angled toward the patient.

The femoral preparation system 600 can include a mounting bracket 640. In some embodiments, the mounting bracket 640 can be an L shaped bracket. The mounting bracket 640 can include a first portion 642. The first portion 642 can be a tapered projection. The first portion 642 can slide relative to the groove 636 of the extension 630. The first portion 642 and the groove 636 can interlock. The first portion 642 and the groove 636 can have one degree of freedom. The first portion 642 can include a scale. The first portion 642 can include markings to indicate the length relative to the extension 630. The first portion 642 can include markings to indicate length relative to the pin 634. Indicia of distance on first portion 642 can be recorded as an input into the surgical orientation device 300. The mounting bracket 640 can include a second portion 644. The first portion 642 and the second portion 644 can be perpendicular. The second portion 644 can include a hub 646.

The femoral preparation system 600 can include a push button 650. The push button 650 can slide relative to the hub 646 of the mounting bracket 640. The femoral preparation system 600 can include a spring 652. The spring 652 can bias the push button 650.

The femoral preparation system 600 can include a connector 660. The connector 660 can include a coupler 662. The connector 660 can include one or more openings 664.

The connector 660 can include two openings 664. The opening 664 can receive a threaded pin 666. The femoral preparation system 600 can include one or more threaded pins 666. The femoral preparation system 600 can include two threaded pins 666. The two openings 664 can define the trajectories of the threaded pins 666. The coupler 662 can engage the reference sensor interface 680 shown in FIG. 18. The reference sensor interface 680 can be mounted directly to the connector 662 after a portion of the femoral preparation system 600 is removed.

The push button 650 can engage the coupler 662. The push button 650 can be biased to engage the coupler 662. The push button 650 can be pushed to uncouple a portion of the femoral preparation system 600. The push button 650 can be pushed to allow the mounting bracket 640 to disengage from the connector 660. The push button 650 can be released to disengage the coupler 662. The push button 650 can be released to allow the reference sensor interface 680 to be mounted to the connector 662.

The tibial preparation system 700 can include an orthopedic assembly for use in preparing a tibia for a prosthetic component. The tibial preparation system 700 can include a component for adjusting a posterior/anterior slope of the surgical orientation device 300. The tibial preparation system 700 can include a component for adjusting a posterior/anterior slope of a cutting block. The tibial preparation system 700 can include an also comprise a component for adjusting the varus/valgus slope of the surgical orientation device 300. The tibial preparation system 700 can include an also comprise a component for adjusting the varus/valgus slope of slope a cutting block.

The tibial preparation system 700 can include a landmark acquisition assembly 710. The landmark acquisition assembly 710 can comprise a structure that is configured to contact and/or obtain information about anatomical landmarks on the human body. The landmark acquisition assembly 710 can include an elongate member 712. The landmark acquisition assembly 710 can include a probe member 714 that is located on at least one end of the elongate member 712. The probe member 714 can be configured to contact an anatomical landmark, such as for example a malleolus on a patient's ankle. The elongate member 712 can further comprise a series of markings, indicating distance and/or length. The markings can be used to measure, for example, an AP offset of the probe member 714.

The tibial preparation system 700 can include a midline reference probe assembly. The tibial preparation system 700 can include a threaded bore. The threaded bore can engage the midline reference probe assembly, before the femoral preparation system 600 is mounted thereon. The midline reference probe assembly can be positioned at an appropriate anatomical location at the proximal tibia. The midline reference probe assembly can be at a point just posterior to the insertion of the anterior cruciate ligament (ACL), or at another suitable anatomical landmark. For example, a tip of the midline reference probe assembly can be resting over the insertion point of the anterior cruciate ligament in the knee, and/or a soft point on the top of the tibia commonly referred to as the A/P point of the mechanical axis. This point is generally located along a tibial spine on top of the tibia, and marks the location of a point along the mechanical axis of the leg. Indicia of distance on an upper surface of the midline reference probe assembly can be noted and a corresponding A/P offset position can be an input into the surgical orientation device 300. The A/P point can correspond to a point on the mechanical axis. The surgical orientation device 300 can calculate a second point on the mechanical axis. The surgical orientation device 300 can determine a mechanical axis vector.

The tibial preparation system 700 can include the reference sensor interface 780. The tibial preparation system 700 can include the surgical orientation device interface 770. The reference sensor 400 can couple to the reference sensor interface 780. The surgical orientation device 300 can couple to the surgical orientation device interface 770. During tibia registration, the tibial preparation system 700 is assembled with the reference sensor 400 coupled to the reference sensor interface 780 and the surgical orientation device 300 coupled to the surgical orientation device interface 770. The surgical orientation device 300 can be mounted to a movable portion of the tibial preparation system 700. The reference sensor 400 can be mounted to a fixed portion of the tibial preparation system 700. The reference sensor 400 can track the positon of the tibia during the landmark acquisition.

The method of tibia registration can include acquiring landmarks to determine the location of the mechanical axis passing through the tibia. For example, landmarks can be acquired by engaging the probe member 714 of landmark acquisition assembly 710 first with a medial malleolus, and then with the lateral malleolus (or vice versa). Acquisition of the other malleolus can similarly be accomplished by swinging a portion or portions of the landmark acquisition assembly 710 such that the probe member 714 contacts the other side of the leg. Thereafter, the surgical orientation device 300 can determine the location of the mechanical axis, e.g., by locating sagittal and coronal planes extending through the mechanical axis. In some embodiments, the surgical orientation device 300 can calculate the location of the mechanical axis by assuming that the mechanical axis extends from the point of contact of the midline reference probe assembly with the proximal tibia through a point that is halfway between the two malleolus points contacted by the probe member of the landmark acquisition assembly 710 on either side of the leg, or any other appropriate point.

In some embodiments, the user can activate the surgical orientation device 300, such as by pressing one of the user inputs on the surgical orientation device 300, during each landmark acquisition. Once activated, the, surgical orientation device 300 can register (e.g. record) the orientation of the surgical orientation device 300 as a reference position (e.g. a first reference position). For example, the surgical orientation device 300 can register and/or calculate the current orientation of the surgical orientation device 300 based on data collected from the sensor(s) inside the surgical orientation device 300. The orientation of the surgical orientation device 300 in a first reference position can be used to identify and register the orientation of a coronal plane which contains the mechanical axis of the leg, as well as to determine a first reference point for identifying the location and/or orientation of a sagittal plane containing this same mechanical axis.

The user can then swing the probe member of landmark acquisition assembly 710 over to the other (e.g. medial) side of the leg, such that the reference probe 714 is located adjacent the other malleolus. During each landmark acquisition, the user can palpate the ankle. Once the location of the other (e.g. medial) malleolus is identified, the user can press one of the user inputs on the surgical orientation device 300 to cause the surgical orientation device 300 to determine the orientation of the surgical orientation device 300 in a second reference position. For example, the surgical orientation device 300 can register and/or calculate the current orientation of the surgical orientation device 300 based on data collected from the sensor(s) inside the surgical orientation device 300.

The orientation of the surgical orientation device 300 in the second reference position can again be used to identify the orientation of a coronal plane extending through the tibia that contains the mechanical axis of the leg, and/or can be used to locate a second reference point for identifying the location and/or orientation of a sagittal plane containing the same mechanical axis.

When using the surgical orientation device 300 to determine the first and second reference positions, output of the sensor(s) in the surgical orientation device 300 can be monitored in a manner that minimizes error in the reading. For example, a transient phase can be eliminated in the output of the sensors to arrive at an accurate estimation of the given anatomical landmark.

Once information about both the first and second reference positions has been acquired and registered in the surgical orientation device 300, the surgical orientation device 300 can determine (e.g. calculate) the location of a desired plane between the lateral malleolus and the medial malleolus. The desired plane can correspond to the sagittal plane containing the mechanical axis. The desired plane can vary, depending on factors such as the patient's specific anatomy and the surgeon's training and experience. For example, the desired plane can be located midway between the lateral malleolus and medial malleolus, or 55% toward the medial malleolus from the lateral malleolus, or at some other predetermined location.

The user can use one or more user inputs to direct the surgical orientation device 300 to calculate the location of and/or orientation of the sagittal plane. Once the surgical orientation device 300 has calculated where the sagittal plane is, the surgical orientation device 300 can provide location feedback to the user, for example in the form of a visual signal or signals on the display, indicating that the location of the sagittal plane has been calculated.

The method of femoral registration can include acquiring landmarks to determine the location of the mechanical axis passing through the femur. The femoral preparation system 600 can comprise an orthopedic assembly for femoral preparation. The femoral preparation system 600 is configured to be securely mounted upon the lateral portion of the femur. In some embodiments, the femoral preparation system 600 can include the cutting guide rod 602, the cutting guide bracket 610, the swivel post 620, the extension 630, the mounting bracket 640, the push button 650, and the connector 660.

The femoral preparation system 600 can be mounted on the tibial preparation system 700. The cutting guide rod 602 can engage the tibial preparation system 700. The femoral preparation system 600 can be adjustable. The femoral preparation system 600 can be inserted into the tibial preparation system 700 and secured thereto. The cutting guide bracket 610 can slide relative to the cutting guide rod 602. The swivel post 620 can swivel relative to the cutting guide bracket 610. The extension 630 can be positioned relative to the anatomy.

The femoral preparation system 600 can be aligned with the anatomy of the patient. In preparation for the distal femoral resection, the method can include locating a distal point that is intersected by the mechanical axis of the femur. The method can comprise positioning the threaded pin 634. The threaded pin 634 can be positioned relative to a distal point of the femoral mechanical axis. The threaded pin 634 can be a midline pin. The threaded pin 634 can be in the approximate center of the intercondylar notch. The threaded pin 634 places the femoral preparation system 600 in an approximate center position of the distal end portion of the femur. The method can comprise positioning the extension 630. The extension 630 can swivel via the swivel post 620. The extension 630 can include the opening 632. In some methods, the threaded pin 634 is inserted first and the extension 630 is positioned relative to the threaded pin 634. In other methods, the opening 632 can serve as a drill guide for inserting the threaded pin 634. In some methods, the mounting bracket 640 is uncoupled from the extension 630 during positioning of the extension 630.

In some methods, the mounting bracket 640 is coupled to the connector 660. The push button 650 can be biased. The push button 650 can couple the mounting bracket 640 and the connector 660 forming a unitary structure. In some methods, the mounting bracket 640, the push button 650, and the connector 660 can be pre-assembled.

In some methods, the mounting bracket 640 can positioned relative to the extension 630. The mounting bracket 640 and the extension 630 can form a tongue and groove connection. The method can include sliding the assembled mounting bracket 640 and the connector 660 relative to the extension 630. The method can include reducing the mounting bracket 640 and the connector 660 down until the connector 660 is coincident to the bone. During this movement of the mounting bracket 630 and the connector 660, the extension 630 remains fixed to the femur via the threaded pin 634. The location of the mounting bracket 640 relative to the extension 330 can be an input into the system. The distance that the mounting bracket 640 slides relative to the extension 330 can be an input into the system.

The connector 660 can include one or more openings 664. In some methods, the one or more openings 664 can serve as a drill guide for inserting the threaded pin 666. The threaded pin 666 is inserted through the opening 664 of the connector 660. The openings 664 can be angled. The openings 644 can be offset. The openings 664 can be angled and offset drill guide holes. The connector 660 can be fixed to the femur via the one or more pins 666.

The mounting bracket 640 can be detached from the connector 660. The push button 650 can be pushed toward the connector 660. The push button 650 can disengage the connector 660. The mounting bracket 640 can slide relative to the connector 660 to disengage from the connector 660. The mounting bracket 640 can slide relative to the extension 630 to disengage from the extension 630. The extension 630 can be removed.

The cutting guide rod 602, the cutting guide bracket 610, the swivel post 620, and the extension 630 can be removed. The connector 660 remains fixed to the femur. The connector 660 can couple to the reference sensor 400. The connector 660 can couple to the reference sensor interface 680. The reference sensor 400 can couple to the reference sensor interface 680. In some methods, a cutting block is mounted to the threaded pin 634 for resection. In some methods, the threaded pin 634 can be removed.

The reference sensor device 400 and/or orientation device 300 can be used to determine the relative coordinates of a center pivot point on the femur. By determining the coordinates of the pivot point of the femoral head, the reference sensor device 400 and/or surgical orientation device 300 can calculate the location and/or orientation of the mechanical axis that extends through the femur.

In order to determine the coordinates of the pivot point of the femoral head (i.e. the pivot point of the mechanical axis), the leg can be moved (e.g. swung). For example, the leg can be moved in several different directions and/or planes, with the reference sensor device 400 attached. Readings such as angular rate and acceleration of the femur can be obtained by the reference sensor device 400 until the location and/or orientation of the mechanical axis of the leg and the femur ("femoral mechanical axis") is found. In one embodiment, where one or more multi-axis (e.g., two-axis) accelerometers and gyroscopes are used, reference sensor data for each movement of the femur can be numerically integrated over time to obtain a trajectory of position and velocity points (one point for each IMU data). The IMU data can be integrated without imposing any plane trajectory constraints on movements of the femur.

The acceleration and angular rate sensed by the reference sensor device 400 during the leg movement can be processed while the leg is moved about its pivot point. The reference sensor device 400 can provide an output vector representing the center of the rotation with respect to the inertial sensor axes of the reference sensor device 400.

In some embodiments, prior to determining the location and/or orientation of the center of rotation of the mechanical axis, an error correction technique can be used to remove biases in the surgical orientation device 300 and reference sensor 400. For example, an error correction technique can include assessing 1) static bias; 2) gyroscopic bias; and 3) accelerometer bias in the surgical reference sensor 400 and surgical orientation device 300.

During registration, the surgical orientation device 300 and the reference sensor 400 determine the mechanical axis of the tibia and femur in flexion. The surgical orientation device 300 stores the mechanical axis. In some methods, the leg is transitioned to extension after both mechanical axes are acquired. The surgical orientation device 300 and the reference sensor 400 are configured to sense changes in orientation. The changes in orientation when the leg is in flexion and when the leg is in extension can determine the angulation of the mechanical axes. The changes of the mechanical axes can determine a varus/valgus angle. The changes of the mechanical axes can determine a flexion/extension angle. The changes of the mechanical axes can be measured in the coronal plane. The changes of the mechanical axes in the sagittal plane. In some methods, leg alignment measurements are taken prior to resection. The leg is brought into extension. The changes in the tibia mechanical axis relative to the femoral mechanical axis are calculated. The limb alignment through the hip, knee, and ankle are calculated. The relative positioning of the mechanical axes can be stored by the surgical orientation device before resection.

The surgical orientation device 300 and/or reference sensor 400 can provide guidance to the surgeon as to how to position a cutting block on the bone in order to achieve a cutting plane that is perpendicular to the load bearing axis of the bone. The surgical orientation device 300 and/or reference sensor 400 can provide guidance to the surgeon as to how to position a cutting block on the bone in order to achieve a cutting plane some number of degrees off of that perpendicular plane if desired. The surgical orientation device 300 and/or reference sensor 400 can provide guidance regarding a varus/vulgas angle for a cutting plane. The surgical orientation device 300 and/or reference sensor 400 can provide guidance regarding a flexion/extension angle for a cutting plane.

In some methods, the cutting guide can be fixed to the bone to be cut and the reference sensor 400 and/or surgical orientation device 300 can be coupled to the cutting guide. The tibial preparation system 700 can include the cutting guide. In some methods, one device is attached to a fixed portion of the tibial preparation system 700 to act as a reference to the bone's orientation and the other device is attached to an articulating arm of the tibial preparation system 700 to provide the surgeon a means to find and set the desired cutting plane. The articulating arm of the tibial preparation system 700 can be constrained to only be moved in two dimensions, e.g., pitch and yaw (not rotation). These two axes form a plane that can be adjusted to guide the placement of the cutting block which guides the saw to cut the bone on that plane.

Once the mechanical axis has been identified, the tibial cutting block can be utilized. The cutting block can be positioned such that the cutting block is spaced away from anterior surface of the tibia. The surgical orientation device 300 and the tibial preparation system 700 can used to adjust the cutting block in order to obtain a desired orientation for resection of the top of the tibia. For example, a posterior slope assembly and a varus/valgus assembly of the tibial preparation system 700 can each be independently adjusted to change the angle of the cutting block, and subsequently, the angle of the intended resection. During this adjustment, the surgical orientation device 300 can provide a reading or readings on the display indicating whether the surgical orientation device 300 and the cutting block are aligned with the sagittal plane and/or coronal plane containing the tibia mechanical axis.

Once the mechanical axis has been identified, the femoral cutting block can be utilized. The cutting block can be positioned such that the cutting block is spaced away from distal surface of the femur. The reference sensor 400 and the femoral preparation system 600 can used to adjust the cutting block in order to obtain a desired orientation for resection of the femur. Once the reference sensor device 400 and/or surgical orientation device 300 has calculated the pivot point of the mechanical axis as described above and located the mechanical axis, the user can begin adjusting and orienting the femoral cutting block relative to the location of the mechanical axis. For example, the surgical orientation device 300 can display the varus/valgus and flexion/extension angle adjustments needed for the cutting block to reach neutral alignment with the mechanical axis that passes through the femoral head.

Once the cutting blocks are in position, the cutting blocks can be mounted to a surface by a plurality of pins. After the cutting block has been mounted to the tibia, a proximal portion of the tibia can be resected. After the cutting block has been mounted to the femur, a distal portion of the femur can be resected.

Advantageously, the mechanical axes can be verified after resection. In some methods, the leg is brought to extension after resection. The implant can be positioned within the knee joint. The limb alignment can verify the placement of the implant. The limb alignment can verify the varus/valgus angle in extension. The alignment can verify the flexion/extension angle in extension. In some methods, changes in the tibia mechanical axis is determined after resection In some methods, changes in the femoral mechanical axis is determined after resection. In some embodiments, the location of the reference sensor device 400 on the femur allows leg to be moved to extension. In extension, the relative positioning of the mechanical axes is determined.

In some embodiments, the reference sensor device 400 can enable the procedure to proceed without fixation of the leg being operated upon because the reference sensor device 400 can track the relative positions of the femur. For example, at least one of the reference sensor device 400 and the surgical orientation device 300 can communicate with the other, such that any relative movement of one of the devices can be tracked by the other, and the resulting overall orientation of the reference sensor device 400 and/or surgical orientation device 300 can be displayed on display of the surgical orientation device 300. In some embodiments, the reference sensor device 400 can track movement of the femur. In some embodiments, the surgical orientation device 300 can track movement of the tibia.

The surgical orientation device 300 and the reference sensor 400 can record any points or axes. The surgical orientation device 300 and the reference sensor 400 can store these points and axes during the procedure. The surgical orientation device 300 can reference these stored mechanical axes after resection. The surgical orientation device 300 and the reference sensor 400 can be used to measure and record the location of anatomical landmarks. The mechanical axis of a leg, as defined herein, generally refers to a line extending from the center of rotation of a proximal head of a femur (e.g. the center of the femoral head) through, ideally, the approximate center of the knee, to a center, or mid-point, of the ankle. The mechanical axis of the femur is the same axial line extending from the center of rotation of the proximal head of the femur through the center of the distal end of the femur (the center of distal end of the femur is commonly described as the center of the intercondylar notch). Generally, an ideal mechanical axis in a patient allows load to pass from the center of the hip, through the center of the knee, and to the center of the ankle.

The surgical orientation device 300, in conjunction with the reference sensor 400, can be used to locate the spatial orientation of the mechanical axes. In some methods, the surgical orientation device 300 and the reference sensor 400 can be used to locate one, two, or more planes intersecting the mechanical axis. In some methods, the surgical orientation device 300 and the reference sensor 400 can be used to locate the coronal plane. In some methods, the surgical orientation device 300 and the reference sensor 400 can be used to locate the sagittal plane. The surgical orientation device 300 and the reference sensor 400 can also be used for verifying an alignment of an orthopedic fixture or fixtures, or a cutting plane or planes, before resection. The surgical orientation device 300 and the reference sensor 400 can also be used for verifying an alignment of an orthopedic fixture or fixtures, or a cutting plane or planes, after resection. The surgical orientation device 300 and the reference sensor 400 can be used to determine alignment of the mechanical axes before resection. The surgical orientation device 300 and the reference sensor 400 can be used to determine alignment of the mechanical axes after resection. The surgical orientation device 300 and the reference sensor 400 can be used to determine gap measurements after resection.

The surgical orientation device 300 can be mounted on the tibial preparation system 700 during tibial registration. The surgical orientation device 300 can remain mounted on the tibial preparation system 700 during femoral registration. The surgical orientation device 300 can remain mounted on the tibial preparation system 700 as the leg is brought into extension for limb alignment and/or gap measurements. The surgical orientation device 300 can remain mounted on the tibial preparation system 700 to determine one or more angles between the mechanical axes. The surgical orientation device 300 can remain mounted on the tibial preparation system 700 during and after resection. The surgical orientation device 300 can remain mounted on the tibial preparation system 700 during limb alignment measurements after resection.

In some methods, the reference sensor 400 can be mounted on the tibial preparation system 700 during tibial registration. The reference sensor 400 can be moved femoral preparation system 600 during femoral registration. The reference sensor 400 can remain mounted on the femoral preparation system 600 during limb alignment and/or gap balancing measurements. The reference sensor 400 can remain mounted on the femoral preparation system 600 as the leg is brought into extension. The reference sensor 400 can remain mounted on the femoral preparation system 600 to determine one or more angles between the mechanical axes. The reference sensor 400 can remain mounted on the femoral preparation system 600 during and after resection. In some methods, the reference sensor 400 can be moved back to the tibial preparation system 700 during and after resection. In some methods, the reference sensor 400 can be moved back to the tibial preparation system 700 for calibration. The reference sensor 400 can be moved back to the femoral preparation system 600 during limb alignment measurements after resection.

The limb alignment measurements can include angulations in the tibia mechanical axis and the femoral mechanical axis when the leg is in extension. The limb alignment measurements can be useful for partial knee replacement. The limb alignment measurements can be useful for total knee replacement. The limb alignment measurements can improve longevity for any implant. The limb alignment measurements can determine the mechanical axis extending through the hip, knee, and ankle of the patient. The limb alignment measurements can determine the varus/valgus angle between the mechanical axis of the tibia and femur. The limb alignment measurements can determine an angle in the coronal plane. The limb alignment measurements can determine the flexion/extension angle between the mechanical axis of the tibia and femur. The limb alignment measurements can determine an angle in the sagittal plane.

The limb alignment measurement can provide cut verification. The surgeon can perform a resection. The resection can be a neutral cut. The resection can be some angle relative to the coronal plane. The resection can be some angle relative to the sagittal plane. In total knee replacement, the resection can include a proximal distal cut. In total knee replacement, the resection can include the medal and lateral compartment cut. In partial knee replacement, the resection does not include a proximal distal cut. In partial knee replacement, the resection can include one compartment. The implant can change the overall alignment of the mechanical axis of the leg. The implant can change the varus/valgus angle. The implant can change the flexion/extension angle. The implant can change the gap. The limb alignment measurement can determine the relative orientation of the mechanical axes after placement of the implant. The limb alignment measurement can determine if the implant provides a correction in the coronal plane. The limb alignment measurement can determine if the implant provides a correction in the sagittal plane. The limb alignment measurement can determine if the measured angles correlates with pre-operative angles determined from imaging techniques. The measurements can provide information on whether soft tissue release is needed. The measurements can determine lift off relative to the implant.

The limb alignment measurement can determine how the mechanical axis of the tibia rotates about the mechanical axis of the femur. The limb alignment measurement can be performed after the mechanical axes are acquired. The limb alignment measurement can be performed after the mechanical axes are stored. The limb alignment measurement can be performed after the surgical orientation device 300 and the reference sensor 400 are calibrated. The limb alignment measurement can be performed before resection. The limb alignment measurement can be performed after resection. The limb alignment measurement can be performed when the leg is in extension. The limb alignment measurement can be performed after the implant is positioned. The limb alignment measurement can be performed anytime during the surgical procedure.

In some methods, a force is applied to the knee. The surgical orientation device 300, in conjunction with the reference sensor 400 can perform gap balancing assessments. During gap assessment, the reference sensor 400 is mounted on femur. During gap assessment, the surgical orientation device 300 is mounted on tibia. In some methods, the surgical orientation device 300 and the reference sensor 400 perform gap balancing before limb alignment measurements. In some methods, the surgical orientation device 300 and the reference sensor 400 perform gap balancing after limb alignment measurements. In some methods, the surgical orientation device 300 and the reference sensor 400 perform gap balancing when the leg is in extension. In some methods, gap balancing is performed with at least one implant positioned between the tibia and the femur. The angle between the surgical orientation device 300 and the reference sensor 400 can be determined with the condyles touching. This angle can be registered as 0 degrees. The tibia and the femur can be taken through a range of motion. In some embodiments, a varus force is applied to the tibia. In some embodiments, a valgus force is applied to the tibia. The angle between the surgical orientation device 300 on the tibia and the reference sensor 400 on the femur can be determined. In some methods, the user applies a varus torque. In some methods, the user applies a valgus torque.

The intercondylar distance can be known. The intercondylar distance can be determined from images, such as x-rays. The intercondylar distance can be measured during surgery. This distance can be an input into the surgical orientation device 300. In the illustrated example, the intercondylar distance is 55 mm. The gap due to varus force can be determined based on a geometric relationship based on the known applied varus force and the intercondylar distance. The gap due to valgus force can be determined based on a geometric relationship in the same manner as the gap due to varus force. The gap can be calculated by applying a force and measuring the change in angle from the femoral mechanical axis and the tibial mechanical axis. This angle and the intercondylar distance can provide an estimate of the gap.

One or more of the surgical orientation device 300 and the reference sensor 400 can calculate the gap distance. The gap distance is a product of the measured angles between the tibia and the femur. The gap distance is a product of the known intercondylar distance. In some embodiments, dynamic gap heights provide insight into medial/lateral ligament tension. The gap heights can provide insight into soft tissue balancing. The gap measurements can determine if further soft tissue release is needed. The gap measurements can be determined before resection. The gap measurements can be determined after resection. The gap can be assessed before and after resections. The gap can be assessed with a plurality of implants or trial implants.

The surgical orientation device 300 can comprise a display. The surgical orientation device 300 is located within the surgical field during limb alignment measurements. The surgical orientation device 300 is located within the surgical field during gap measurements. The display can be sized such that a user can readily read numbers, lettering, and/or symbols displayed on the display screen while performing the procedure. The display can facilitate positioning of the cutting guide during resection. The display can provide information to verify the position of the mechanical axis after resection. The display can provide information on limb alignment. The display can provide information on gap balancing.

The surgical orientation device 300 can store data that is measured or calculated. The surgical orientation device 300 can store data that is inputted by the user. The surgical orientation device 300 can store a distance measurement corresponding to the mounting bracket 640 relative to the extension 630. The surgical orientation device 300 can store the length and/or angle of the extension 630. The surgical orientation device 300 can store an orientation of the femoral preparation system 600. The surgical orientation device 300 can further comprise at least one user input device. The at least one user input device can comprise a plurality of buttons located adjacent the display. The buttons can be activated, for example, by a finger, hand, and/or instrument to input data. The data can include distance measurements related to anatomical landmarks. The surgical orientation device 300 includes a user interface with which a clinician can interact during a procedure.

The surgical orientation device 300 and the reference sensor 400 can acquire and store data related to position and orientation. The surgical orientation device 300 includes an electrical system. The electrical system can include one or more features including: one or more sensors, an electronic control unit that communicates with one or more sensors, one or more visible alignment indicators, a power supply, the display, memory, one or more user input devices, one or more processors, program logic, other substrate configurations representing data and instructions, controller circuitry, processor circuitry, processors, general purpose single-chip or multi-chip microprocessors, digital signal processors, embedded microprocessors, microcontrollers, other output devices and/or one or more input/output ("I/O") ports. In certain embodiments, the electronic control unit can be configured to convert the electronic data from a machine-readable format to a human readable format for presentation on the display of the surgical orientation device 300. The electronic control unit can communicate with internal memory and/or the external memory to retrieve and/or store data and/or program instructions for software and/or hardware. The internal memory and the external memory can include random access memory ("RAM"), such as static RAM, for temporary storage of information and/or read only memory ("ROM"), such as flash memory, for more permanent storage of information. In general, the sensor(s) can be configured to provide continuous real-time data to one or more processors. The electronic control unit can be configured to receive the real-time data from the sensor(s) and to use the sensor data to determine, estimate, and/or calculate an orientation or position of the surgical orientation device 300 and/or the orientation or position of the reference sensor 400.

In some embodiments, in addition or alternatively to the surgical orientation device 300, the system can include an external display. The electronic equipment can include one or more handheld devices such as a computer, desktop computer, laptop computer, or tablet computer such as an iPad®. In some embodiments, the display is located within the surgical field. In some embodiments, the display is located outside the surgical field. In some embodiments, the reference sensor device 400 can include a display. In some embodiments, in addition or alternatively to the surgical orientation device 300, electronic equipment can include at least one user input device. The user input device can be activated, for example, by a finger, hand, and/or instrument. The electronic equipment can include software and/or hardware for the systems described herein. The electronic equipment can include external memory for the systems described herein. The surgical orientation device 300 and/or the reference sensor device 400 can connect to the internet. The surgical orientation device 300 and/or the reference sensor device 400 can transmit or receive information from the internet. The surgical orientation device 300 and/or the reference sensor device 400 can connect to the cloud. The surgical orientation device 300 and/or the reference sensor device 40 can transmit or receive information from the cloud.

In some arrangements, the one or more sensors of the surgical orientation device 300 and/or the reference sensor device 400 can comprise at least one orientation sensor configured to provide real-time data to the electronic control unit related to the motion, orientation, and/or position of the surgical orientation device 300 and/or the reference sensor device 400. For example, the sensor module can comprise at least one gyroscopic sensor, accelerometer sensor, tilt sensor, magnetometer and/or other similar device or devices configured to measure, and/or facilitate determination of, an orientation of the surgical orientation device 300 and/or the reference sensor device 400. In some embodiments, the sensors can be configured to provide measurements relative to a reference point(s), line(s), plane(s), and/or gravitational zero. Gravitational zero, as referred to herein, refers generally to an orientation in which an axis of the sensor is perpendicular to the force of gravity, and thereby experiences no angular offset, for example tilt, pitch, roll, or yaw, relative to a gravitational force vector. In other embodiments, the sensor(s) can be configured to provide measurements for use in dead reckoning or inertial navigation systems.

In various embodiments, the sensor(s) comprise one or more accelerometers that measure the static acceleration of the surgical orientation device 300 and/or the reference sensor device 400 due to gravity. For example, the accelerometers can be used as tilt sensors to detect rotation of the surgical orientation device 300 and/or the reference sensor device 400 about one or more of its axes. The one or more accelerometers can comprise a dual axis accelerometer (which can measure rotation about two axes of rotation) or a three-axis accelerometer (which can measure rotation about three axes of rotation). The changes in orientation about the axes of the accelerometers can be determined relative to gravitational zero and/or to a reference plane registered during a tibial or femoral preparation procedure as described herein.

In certain embodiments, a multi-axis accelerometer (such as the ADXL203CE MEMS accelerometer available from Analog Devices, Inc. or the LIS331DLH accelerometer available from ST Microelectronics.) detects changes in orientation about two axes of rotation. For example, the multi-axis accelerometer can detect changes in angular position from a horizontal plane (e.g., anterior/posterior rotation) surgical orientation device 300 and/or the reference sensor device 400 and changes in angular position from a vertical plane (e.g., roll rotation) of the surgical orientation device 300 and/or the reference sensor device 400. The changes in angular position from the horizontal and vertical planes of the surgical orientation device 300 and/or the reference sensor device 400 (as measured by the sensor can also be used to determine changes in a medial-lateral orientation (e.g., varus/valgus rotation) of the surgical orientation device 300 and/or the reference sensor device 400

In some arrangements, the sensors comprise at least one single- or multi-axis gyroscope sensor and at least one single- or multi-axis accelerometer sensor. For example, the sensor can comprise a three-axis gyroscope sensor (or three gyroscope sensors) and a three-axis accelerometer (or three accelerometer sensors) to provide position and orientation measurements for all six degrees of freedom of the surgical orientation device 300 and/or the reference sensor device 400. In some embodiments, the sensors provide an inertial navigation or dead reckoning system to continuously calculate the position, orientation, and velocity of the surgical orientation device 300 and/or the reference sensor device 400 without the need for external references The reference sensor 400 can include any of the features of the surgical orientation device 300. The surgical orientation device 300 and/or the reference sensor 400 includes in one embodiment one or more sensors that together can form an inertial measurement unit (IMU). In particular, the IMU includes a first sensor for determining acceleration and a second sensor for determining gyroscopic positioning. As discussed herein, the first sensor can be an accelerometer and the second sensor can be a gyroscopic sensor. The reference sensor 400 also includes a transmitter for sending data from the sensors to the electrical system of the surgical orientation device 300. The information received from the reference sensor 400 can be fed to an input port, or alternatively, the electronic control unit of the surgical orientation device 300 can itself receive the information wirelessly. The information from the reference sensor 400 can correspond, for example, to the position and/or orientation of the reference sensor 400, and can be used by the surgical orientation device 300 to determine an aggregate, relative, or overall position and/or orientation of the surgical orientation device 300 and/or the reference sensor device 400.

The surgical orientation device 300 and/or the reference sensor device 400 can be used to measure and record the location of anatomical landmarks, such as the location of the mechanical axis of a leg, tibia, and femur. Additional details of systems, devices, sensors, and methods are set forth in U.S. application Ser. No. 10/864,085 filed Jun. 9, 2004, U.S. application Ser. No. 11/182,528 filed Jul. 15, 2009, U.S. application Ser. No. 12/557,051 filed Sep. 10, 2009, U.S. application Ser. No. 12/509,388 filed Jul. 24, 2009, U.S. application Ser. No. 13/011,815 filed Jan. 21, 2011, U.S. application Ser. No. 13/115,065, filed May 24, 2011; U.S. application Ser. No. 14/399,046 filed Nov. 5, 2014, U.S. application Ser. No. 14/401,274 filed Nov. 14, 2014, U.S. application Ser. No. 13/800,620 filed Mar. 13, 2013, U.S. application Ser. No. 14/643,864 filed Mar. 10, 2015, U.S. application Ser. No. 15/550,564 filed Aug. 11, 2017, U.S. application Ser. No. 15/920,216 filed Mar. 13, 2018, U.S. application Ser. No. 15/920,202 filed Mar. 13, 2018, and PCT/US2020/063785 filed Dec. 8, 2020, which are all incorporated by reference herein in their entireties for all purposes.

Although these inventions have been disclosed in the context of certain preferred embodiments and examples, it will be understood by those skilled in the art that this application extends beyond the specifically disclosed embodiments to other alternative embodiments and/or uses of the invention and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or sub-combinations of the specific features and aspects of the embodiments may be made and still fall within the scope of the application. For example, the application contemplates the connection hub alone or in combination with any of the other modules could comprise a separate aspect. Or, any one or a combination of the modules could be directly connected to an umbrella hub or overhead support to form another separate aspect. Accordingly, it should be understood that various features and aspects of the disclosed embodiments can be combined with or substituted for one another in order to form varying modes of the disclosed embodiments. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A system for limb alignment, comprising:
a first orientation device configured to be coupled with a tibia before resection, the first orientation device comprising at least one inertial sensor to assess characteristics of a knee joint before resection;
a second orientation device configured to be coupled with a femur before resection, the second orientation device comprising at least one inertial sensor to assess characteristics of the knee joint before resection; and
a femoral preparation system comprising a bone engagement portion configured to be driven into the femur and a coupler portion, wherein the second orientation device comprises an interface configured to be lowered onto the coupler portion to mount the second orientation device directly to the coupler portion, wherein the femoral preparation system is configured to be mounted to the femur, outside of the space between the tibia and the femur to allow the knee to articulate along natural articular surfaces of the tibia and the femur and be placed in flexion and extension before resection,
wherein the first orientation device or the second orientation device comprise a processor configured to receive inertial sensor data, wherein the processor is configured to determine a femoral mechanical axis and a tibial mechanical axis in flexion, wherein the system for limb alignment is configured to store a relative positioning of the femoral mechanical axis and the tibial mechanical axis before resection, wherein the processor is configured to calculate an angle between the femoral mechanical axis and the tibial mechanical axis when the first orientation device is coupled with the tibia before resection and the second orientation device is coupled with the femur before resection.

2. The system of claim 1, further comprising a tibial preparation system comprising a first device interface configured to couple to the first orientation device and a second device interface configured to couple to the second orientation device.

3. The system of claim 2, wherein the femoral preparation system is configured to be mounted on the tibial preparation system.

4. The system of claim 1, wherein the femoral preparation system comprises a cutting guide bracket configured to slide relative to a tibial preparation system.

5. The system of claim 1, wherein the femoral preparation system comprises a swivel post configured to swivel relative to a tibial preparation system.

6. The system of claim 1, wherein the femoral preparation system comprises an extension configured to be positioned relative to a threaded pin coupled to a portion of the distal femur.

7. The system of claim 1, wherein the processor is configured to determine the femoral mechanical axis and the tibial mechanical axis based at least in part on the location of anatomical landmarks.

8. The system of claim 1, wherein the processor is configured to determine the femoral mechanical axis and the tibial mechanical axis based at least in part on movement of the femur.

9. The system of claim 1, wherein the processor is configured to determine varus/valgus angle of the femoral mechanical axis and the tibial mechanical axis.

10. The system of claim 1, wherein the processor is configured to determine flexion/extension angle of the femoral mechanical axis and the tibial mechanical axis.

11. The system of claim 1, wherein the processor is configured to determine a gap measurement.

12. The system of claim 1, further comprising a tibial preparation system comprising a probe member.

13. The system of claim 1, further comprising a tibial preparation system comprising a midline reference probe assembly.

14. The system of claim 1, wherein the first orientation device and the second orientation device are configured to determine alignment of the femoral mechanical axis and the tibial mechanical axis before and after resection.

15. The system of claim 1, wherein the first orientation device and second orientation device are configured to sense changes in orientation, wherein changes in orientation when the leg is in flexion and when the leg is in extension determine the angulation of the femoral mechanical axis and the tibial mechanical axis.

16. The system of claim 1, wherein the first orientation device and second orientation device are configured to verify the femoral mechanical axis and the tibial mechanical axis after resection.

17. The system of claim 1, wherein the first orientation device and the second orientation device are configured to calculate a rotation of the tibial mechanical axis about the femoral mechanical axis when the first orientation device is coupled with the tibia before resection and the second orientation device is coupled with the femur before resection.

18. The system of claim 1, wherein changes of the femoral mechanical axis and the tibial mechanical axis are measured in the coronal plane.

19. The system of claim 1, wherein changes of the femoral mechanical axis and the tibial mechanical axis are measured in the sagittal plane.

* * * * *